(12) United States Patent
Manchester et al.

(10) Patent No.: US 10,544,411 B2
(45) Date of Patent: Jan. 28, 2020

(54) METHODS FOR GENERATING A GLUCOSE PERMEASE LIBRARY AND USES THEREOF

(71) Applicant: Zymergen Inc., Emeryville, CA (US)

(72) Inventors: Shawn Manchester, Oakland, CA (US); Jeffrey Mellin, Oakland, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 16/313,613

(22) PCT Filed: Jun. 29, 2017

(86) PCT No.: PCT/US2017/039997
§ 371 (c)(1),
(2) Date: Dec. 27, 2018

(87) PCT Pub. No.: WO2018/005793
PCT Pub. Date: Jan. 4, 2018

(65) Prior Publication Data
US 2019/0194647 A1 Jun. 27, 2019

Related U.S. Application Data

(60) Provisional application No. 62/356,924, filed on Jun. 30, 2016.

(51) Int. Cl.
*C12N 9/12* (2006.01)
*C12P 1/04* (2006.01)
*C12N 15/10* (2006.01)

(52) U.S. Cl.
CPC ....... *C12N 15/1037* (2013.01); *C12N 9/1205* (2013.01); *C12P 1/04* (2013.01);
(Continued)

(58) Field of Classification Search
CPC ............. C12N 15/1037; C12N 9/1205; C12N 2800/22; C12N 15/77; C12N 1/20;
(Continued)

(56) References Cited

U.S. PATENT DOCUMENTS 4,435,504 A   3/1984   Zuk et al.
4,489,160 A   12/1984  Katsumata et al.
(Continued)

FOREIGN PATENT DOCUMENTS

DE   19548222 A1   6/1997
DE   19831609 A1   4/1999
(Continued)

OTHER PUBLICATIONS

"Designing a Million Genomes: Machine Learning, Automation and Biotech.", Strata + Hadoop World, Make Data Work conference, London, UK, May 5, 2015; https://www.youtube.com/watch?v=658kvYgrJBE&feature=youtu.be, Published on Oct. 7, 2015, Business-focused talk at Strata UK 2015 by Aaron Kimball, CTO of Zymergen Inc.
(Continued)

*Primary Examiner* — Jeremy C Flinders
(74) *Attorney, Agent, or Firm* — Cooley LLP

(57) ABSTRACT

The present disclosure describes methods for generating microbial strains expressing a heterologous bacterial glucose permease gene that produce biomolecules of interest. In aspects, the disclosure provides novel bacterial strains, which express a heterologous bacterial glucose permease gene whose expression is controlled by a native *Corynebacterium glutamicum* promoter or a mutant promoter derived therefrom. Also provided herein are methods for producing a library of bacterial glucose permease genes using a pro-
(Continued)

moter ladder comprising a plurality of promoters derived from *Corynebacterium glutamicum*.

20 Claims, 4 Drawing Sheets

Specification includes a Sequence Listing.

(52) U.S. Cl.
CPC .................. *C12Y 207/01001* (2013.01); *C12Y 207/01069* (2013.01)

(58) Field of Classification Search
CPC .... C12Y 207/01069; C12Y 207/01001; C12Y 7/01002; C12P 1/04; C12P 21/02; C12P 19/02; C12P 19/30; C07K 1/047
See application file for complete search history.

(56) References Cited

U.S. PATENT DOCUMENTS

| | | |
|---|---|---|
| 4,601,893 A | 7/1986 | Cardinal |
| 4,855,240 A | 8/1989 | Rosenstein et al. |
| 4,980,298 A | 12/1990 | Blake et al. |
| 5,158,891 A | 10/1992 | Takeda et al. |
| 5,275,940 A | 1/1994 | Kino et al. |
| 5,487,993 A | 1/1996 | Herrnstadt et al. |
| 5,516,670 A | 5/1996 | Kuehnle et al. |
| 5,591,645 A | 1/1997 | Rosenstein |
| 5,602,030 A | 2/1997 | Ingrahm et al. |
| 5,605,793 A | 2/1997 | Stemmer |
| 5,753,477 A | 5/1998 | Chan |
| 5,756,345 A | 5/1998 | Camakaris et al. |
| 5,770,409 A | 6/1998 | Pfefferle et al. |
| 5,811,238 A | 9/1998 | Stemmer et al. |
| 5,827,698 A | 10/1998 | Kikuchi et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 5,990,350 A | 11/1999 | Stevens et al. |
| 6,040,439 A | 3/2000 | Hayakawa et al. |
| 6,060,296 A | 5/2000 | Hoekstra |
| 6,090,592 A | 7/2000 | Adams et al. |
| 6,117,679 A | 9/2000 | Stemmer et al. |
| 6,136,565 A | 10/2000 | Best et al. |
| 6,174,673 B1 | 1/2001 | Short et al. |
| 6,251,674 B1 | 6/2001 | Tobin et al. |
| 6,287,862 B1 | 9/2001 | delCardayre et al. |
| 6,300,070 B1 | 10/2001 | Boles et al. |
| 6,326,204 B1 | 12/2001 | delCardayre et al. |
| 6,335,160 B1 | 1/2002 | Paatten et al. |
| 6,335,198 B1 | 1/2002 | delCardayre et al. |
| 6,352,859 B1 | 3/2002 | delCardayre et al. |
| 6,358,709 B1 | 3/2002 | Short et al. |
| 6,379,964 B1 | 4/2002 | del Cardayre et al. |
| 6,479,258 B1 | 11/2002 | Short |
| 6,528,311 B1 | 3/2003 | delCardayre et al. |
| 6,586,214 B1 | 7/2003 | Dunican et al. |
| 6,605,449 B1 | 8/2003 | Short |
| 6,713,279 B1 | 3/2004 | Short |
| 6,716,631 B1 | 4/2004 | delCardayre et al. |
| 6,759,195 B1 | 7/2004 | Bentley et al. |
| 6,759,218 B2 | 7/2004 | Mockel et al. |
| 6,962,989 B1 | 11/2005 | Pompejus et al. |
| 7,033,781 B1 | 4/2006 | Short |
| 7,115,400 B1 | 10/2006 | Adessi et al. |
| 7,118,904 B2 | 10/2006 | Mockel et al. |
| 7,127,379 B2 | 10/2006 | Palsson et al. |
| 7,138,266 B2 | 11/2006 | Debabov et al. |
| 7,148,054 B2 | 12/2006 | delCardayre et al. |
| 7,507,574 B2 | 3/2009 | Bill et al. |
| 7,510,854 B2 | 3/2009 | Pompejus et al. |
| 7,629,170 B2 | 12/2009 | delCardayre et al. |
| 7,711,490 B2 | 5/2010 | Maranas et al. |
| 7,826,975 B2 | 11/2010 | Maranas et al. |
| 7,842,485 B2 | 11/2010 | Gill et al. |
| 7,846,688 B2 | 12/2010 | Gill et al. |
| 7,987,056 B2 | 7/2011 | Gill et al. |
| 8,076,138 B2 | 12/2011 | delCardayre et al. |
| 8,108,152 B2 | 1/2012 | Maranas et al. |
| 8,110,360 B2 | 2/2012 | Serber et al. |
| 8,221,982 B2 | 7/2012 | Serber et al. |
| 8,332,160 B1 | 12/2012 | Platt et al. |
| 8,349,587 B2 | 1/2013 | Fischer et al. |
| 8,377,681 B2 | 2/2013 | delCardayre et al. |
| 8,467,975 B2 | 6/2013 | Gill et al. |
| 8,476,041 B2 | 7/2013 | Cervin et al. |
| 8,530,203 B2 | 9/2013 | Ikeda et al. |
| 8,546,136 B2 | 10/2013 | Serber et al. |
| 8,685,737 B2 | 4/2014 | Serber et al. |
| 8,697,359 B1 | 4/2014 | Zhang |
| 8,741,603 B2 | 6/2014 | Han et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,883,464 B2 | 11/2014 | Lynch et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,388,419 B2 | 7/2016 | Lynch et al. |
| 9,428,778 B2 | 8/2016 | Lynch et al. |
| 9,506,087 B2 | 11/2016 | Vroom et al. |
| 9,506,167 B2 | 11/2016 | Shetty et al. |
| 9,580,719 B2 | 2/2017 | Retallack et al. |
| 9,637,739 B2 | 5/2017 | Siksnys et al. |
| 9,677,090 B2 | 6/2017 | Donohue et al. |
| 9,688,972 B2 | 6/2017 | May et al. |
| 9,701,971 B2 | 7/2017 | Serber et al. |
| 9,738,687 B2 | 8/2017 | Guay et al. |
| 9,745,562 B2 | 8/2017 | Donohue et al. |
| 9,752,176 B2 | 9/2017 | Kung et al. |
| 9,771,795 B2 | 9/2017 | Knight et al. |
| 9,790,490 B2 | 10/2017 | Zhang et al. |
| 9,816,081 B1 | 11/2017 | Donohue et al. |
| 9,822,372 B2 | 11/2017 | Zhang et al. |
| 9,840,713 B2 | 12/2017 | Zhang |
| 9,902,980 B2 | 2/2018 | Fischer et al. |
| 9,988,624 B2 | 6/2018 | Serber et al. |
| 10,047,358 B1 | 8/2018 | Serber et al. |
| 2002/0169562 A1 | 11/2002 | Stephanopoulos et al. |
| 2002/0197605 A1 | 12/2002 | Nakagawa et al. |
| 2003/0027175 A1 | 2/2003 | Stephanopoulos et al. |
| 2004/0077090 A1 | 4/2004 | Short |
| 2004/0101963 A1 | 5/2004 | Bibb et al. |
| 2005/0054106 A1 | 3/2005 | Ow et al. |
| 2005/0124010 A1 | 6/2005 | Short et al. |
| 2006/0019301 A1 | 1/2006 | Hansen et al. |
| 2006/0084098 A1 | 4/2006 | Gill et al. |
| 2006/0269975 A1 | 11/2006 | Pompejus et al. |
| 2006/0286574 A1 | 12/2006 | Romesberg et al. |
| 2007/0166792 A1 | 1/2007 | Olson et al. |
| 2007/0042474 A1 | 2/2007 | Pompejus et al. |
| 2007/0059768 A1 | 3/2007 | Gill et al. |
| 2007/0118916 A1 | 5/2007 | Puzio et al. |
| 2007/0122890 A1 | 5/2007 | Park et al. |
| 2007/0218533 A1 | 9/2007 | Gill et al. |
| 2007/0274972 A1 | 11/2007 | Muller et al. |
| 2007/0292918 A1 | 12/2007 | Stelman et al. |
| 2008/0103060 A1 | 5/2008 | Gill et al. |
| 2008/0243397 A1 | 10/2008 | Peccoud et al. |
| 2009/0221442 A1 | 9/2009 | Dower et al. |
| 2009/0253174 A1 | 10/2009 | Serber et al. |
| 2009/0280529 A1 | 11/2009 | Berg et al. |
| 2009/0325248 A1 | 12/2009 | Marx et al. |
| 2010/0048938 A1 | 2/2010 | Berg et al. |
| 2010/0105865 A1 | 4/2010 | Telford et al. |
| 2010/0124768 A1 | 5/2010 | Serber et al. |

(56) References Cited

U.S. PATENT DOCUMENTS

| | | |
|---|---|---|
| 2010/0136633 A1 | 6/2010 | Serber et al. |
| 2010/0137143 A1 | 6/2010 | Rothberg et al. |
| 2010/0210017 A1 | 8/2010 | Gill et al. |
| 2010/0216648 A1 | 8/2010 | Stahler et al. |
| 2010/0304982 A1 | 12/2010 | Hinz et al. |
| 2010/0317115 A1 | 12/2010 | Gill et al. |
| 2011/0054654 A1 | 3/2011 | Phillips et al. |
| 2011/0136688 A1 | 6/2011 | Scholl et al. |
| 2011/0172127 A1 | 7/2011 | Jacobsen et al. |
| 2011/0223638 A1 | 9/2011 | Wiedenheft et al. |
| 2011/0223671 A1 | 9/2011 | Yoder et al. |
| 2011/0244575 A1 | 10/2011 | Lipscomb et al. |
| 2011/0277179 A1 | 11/2011 | Puzio et al. |
| 2012/0070870 A1 | 3/2012 | Way et al. |
| 2012/0077681 A1 | 3/2012 | Gill et al. |
| 2012/0245056 A1 | 9/2012 | Serber et al. |
| 2012/0252681 A1 | 10/2012 | Del Cardayre et al. |
| 2012/0264902 A1 | 10/2012 | Lipscomb et al. |
| 2012/0277120 A1 | 11/2012 | Del Cardayre et al. |
| 2013/0071893 A1 | 3/2013 | Lynch et al. |
| 2013/0078709 A1 | 3/2013 | Franklin et al. |
| 2013/0122541 A1 | 5/2013 | Lynch et al. |
| 2013/0149742 A1 | 6/2013 | Bower et al. |
| 2013/0217132 A1 | 8/2013 | Gill et al. |
| 2013/0252240 A1 | 9/2013 | Cutler et al. |
| 2014/0045231 A1 | 2/2014 | Lynch et al. |
| 2014/0068797 A1 | 3/2014 | Doudna et al. |
| 2014/0172318 A1 | 6/2014 | Fisher et al. |
| 2014/0180660 A1 | 6/2014 | Clancy et al. |
| 2014/0186942 A1 | 7/2014 | Serber et al. |
| 2014/0295457 A1 | 10/2014 | Broenstrup et al. |
| 2014/0356921 A1 | 12/2014 | Deng et al. |
| 2015/0031100 A1 | 1/2015 | Gill et al. |
| 2015/0056651 A1 | 2/2015 | Lynch et al. |
| 2015/0056684 A1 | 2/2015 | Lipscomb et al. |
| 2015/0132263 A1 | 5/2015 | Liu et al. |
| 2015/0140626 A1 | 5/2015 | Song et al. |
| 2015/0211013 A1 | 7/2015 | Emalfarb et al. |
| 2015/0275224 A1 | 10/2015 | Basra et al. |
| 2015/0284810 A1 | 10/2015 | Knight et al. |
| 2015/0284811 A1 | 10/2015 | Knight et al. |
| 2015/0299742 A1 | 10/2015 | Gill et al. |
| 2015/0315599 A1 | 11/2015 | Shetty et al. |
| 2015/0344916 A1 | 12/2015 | Lynch et al. |
| 2015/0368639 A1 | 12/2015 | Gill et al. |
| 2015/0376628 A1 | 12/2015 | Schoenherr et al. |
| 2016/0046961 A1 | 2/2016 | Jinek et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0283651 A1 | 9/2016 | Knight et al. |
| 2016/0290132 A1 | 10/2016 | Knight et al. |
| 2016/0304905 A1 | 10/2016 | Hansen et al. |
| 2017/0009283 A1 | 1/2017 | Gill et al. |
| 2017/0051310 A1 | 2/2017 | Doudna et al. |
| 2017/0051312 A1 | 2/2017 | Jinek et al. |
| 2017/0067046 A1 | 3/2017 | Gill et al. |
| 2017/0073695 A1 | 3/2017 | Verruto et al. |
| 2017/0074889 A1 | 3/2017 | Shetty et al. |
| 2017/0114377 A1 | 4/2017 | Lynch et al. |
| 2017/0139078 A1 | 5/2017 | Knight et al. |
| 2017/0147742 A1 | 5/2017 | Jayaram et al. |
| 2017/0159045 A1 | 6/2017 | Serber et al. |
| 2017/0173086 A1 | 6/2017 | Boyle et al. |
| 2017/0240886 A1 | 8/2017 | Oleinikov |
| 2017/0240922 A1 | 8/2017 | Gill et al. |
| 2017/0240923 A1 | 8/2017 | Serber et al. |
| 2017/0316353 A1 | 11/2017 | Frewen et al. |
| 2017/0321198 A1 | 11/2017 | Severinov et al. |
| 2017/0321226 A1 | 11/2017 | Gill et al. |
| 2017/0342132 A1 | 11/2017 | Fraser et al. |
| 2017/0369870 A1 | 12/2017 | Gill et al. |
| 2017/0370213 A1 | 12/2017 | Knight et al. |
| 2018/0023120 A1 | 1/2018 | Kung et al. |
| 2018/0216099 A1 | 8/2018 | Serber et al. |
| 2018/0216100 A1 | 8/2018 | Serber et al. |
| 2018/0216101 A1 | 8/2018 | Serber et al. |
| 2018/0362991 A1 | 12/2018 | Serber et al. |

FOREIGN PATENT DOCUMENTS

| | | |
|---|---|---|
| DE | 19947791 A1 | 4/2001 |
| DE | 19950409 A1 | 4/2001 |
| DE | 19959327 A1 | 6/2001 |
| DE | 19959328 A1 | 6/2001 |
| EP | 0131171 A1 | 1/1985 |
| EP | 0238023 A2 | 9/1987 |
| EP | 0197335 B1 | 2/1991 |
| EP | 0472869 A2 | 3/1992 |
| EP | 0356739 B1 | 12/1995 |
| EP | 0743016 A | 11/1996 |
| EP | 0635574 B1 | 4/2003 |
| EP | 0972081 B1 | 6/2007 |
| EP | 1546312 B1 | 7/2014 |
| JP | 01-225487 A | 9/1989 |
| KR | 1020080042823 A | 5/2008 |
| WO | WO 1991/006628 A1 | 5/1991 |
| WO | WO 1995/022625 A1 | 8/1995 |
| WO | WO 1996/015246 A1 | 5/1996 |
| WO | WO 1996/033207 A1 | 10/1996 |
| WO | WO 1998/031837 A1 | 7/1998 |
| WO | WO 2000/020555 A2 | 4/2000 |
| WO | WO 2001/012791 A1 | 2/2001 |
| WO | WO 2002/029032 A2 | 4/2002 |
| WO | WO 2002/051231 A1 | 7/2002 |
| WO | WO 2003/014330 A2 | 2/2003 |
| WO | WO 2003/040373 A2 | 5/2003 |
| WO | WO 2004/054381 A1 | 7/2004 |
| WO | WO 2004/069996 A2 | 8/2004 |
| WO | WO 2005/006875 A2 | 1/2005 |
| WO | WO 2005/021772 A1 | 3/2005 |
| WO | WO 2006/069711 A1 | 7/2006 |
| WO | WO 2007/012078 A1 | 1/2007 |
| WO | WO 2007/015178 A2 | 2/2007 |
| WO | WO 2007/141580 A2 | 12/2007 |
| WO | WO 2009/043803 A2 | 4/2009 |
| WO | WO 2009/126623 A2 | 10/2009 |
| WO | WO 2010/059763 A2 | 5/2010 |
| WO | WO 2010/075424 A2 | 7/2010 |
| WO | WO 2011/154147 A1 | 12/2011 |
| WO | WO 2012/082720 A2 | 6/2012 |
| WO | WO 2012/142591 A2 | 10/2012 |
| WO | WO 2012/149470 A1 | 11/2012 |
| WO | WO 2012/164565 A1 | 12/2012 |
| WO | WO 2013/066848 A1 | 5/2013 |
| WO | WO 2013/142578 A1 | 9/2013 |
| WO | WO 2014/011800 A1 | 1/2014 |
| WO | WO 2014/019527 A1 | 2/2014 |
| WO | WO 2014/089436 A1 | 6/2014 |
| WO | WO 2014/102782 A1 | 7/2014 |
| WO | WO 2015/070193 A1 | 5/2015 |
| WO | WO 2015/123339 A1 | 8/2015 |
| WO | WO 2015/148680 A1 | 10/2015 |
| WO | WO 2015/175793 A1 | 11/2015 |
| WO | WO 2006/028063 A1 | 3/2016 |
| WO | WO 2016/073690 A1 | 5/2016 |
| WO | WO 2016/196319 A1 | 12/2016 |
| WO | WO 2017/037304 A2 | 3/2017 |
| WO | WO 2017/100376 A2 | 6/2017 |
| WO | WO 2017/100377 A1 | 6/2017 |
| WO | WO 2017/189784 A1 | 11/2017 |
| WO | WO 2017/215790 A1 | 12/2017 |
| WO | WO 2017/223538 A1 | 12/2017 |
| WO | WO 2018/005655 A2 | 1/2018 |
| WO | WO 2018/005793 A1 | 1/2018 |
| WO | WO 2018/009372 A1 | 1/2018 |
| WO | WO 2018/013990 A1 | 1/2018 |
| WO | WO 2018/022972 A1 | 2/2018 |

(56) References Cited

FOREIGN PATENT DOCUMENTS

| WO | WO 2018/071672 A1 | 4/2018 |
|---|---|---|
| WO | WO 2018/226964 A2 | 12/2018 |

OTHER PUBLICATIONS

"The Data-Driven future of biotechnology." https://www.youtube.com/watch?v=IYmgJUHcG9g&feature=youtu.be&t=915, Strata + Hadoop World, NY Sep. 28-Oct. 1, 2015, Published on Nov. 15, 2015, Technical talk at Strata NY 2015 by Aaron Kimball, CTO of Zymergen Inc. about Zymergen's technology.
Adrio, Jose-Luis et al., "Recombinant organisms for production of industrial products", Bioengineered Bugs, 2010, pp. 116-131, vol. 1, No. 2.
Almeida, Elionor R.P., et al. "Transgenic expression of two marker genes under the control of an *Arabidopsis* rbcS promoter: Sequences encoding the Rubisco transit peptide increase expression levels." Molecular and General Genetics MGG (1989); 218.1: 78-86.
Alper et al., "Construction of lycopene-overproducing *E. coli* strains by combining systematic and combinatorial gene knockout targets." Nature Biotechnology (2005); 23 (5): 612-616.
Anonymous: "ABI 3900 High Throughput DNA Synthesizer", Mar. 1, 2001 (Mar. 1, 2001), URL:https://assets.thermofisher.com/TFS-Assets/LSG/manuals/cms_095580.pdf [retrieved on Jan. 2, 2018], 144 pages.
Askenazi, M., et al., "Integrating transcriptional and metabolite profiles to direct the engineering of lovastatin-producing fungal strains." Nat. Biotechnol. (2003); 21: 150-156.
Aslanidis, Charalampos, et al. "Ligation-independent cloning of PCR products (LIC-PCR)." Nucleic Acids Research (1990); 18.20: 6069-6074.
Azhayev, Alex V., et al. "Amide group assisted 3'-dephosphorylation of oligonucleotides synthesized on universal A-supports." Tetrahedron (2001); 57.23: 4977-4986.
Barcellos, Fernando Gomes, et al. "Genetic analysis of Aspergillus nidulans unstable transformants obtained by the biolistic process." Canadian Journal of Microbiology (1998); 44.12: 1137-1141.
Bartley, Bryan, et al. "Synthetic biology open language (SBOL) version 2.0. 0." Journal of Integrative Bioinformatics (JIB) (2015); 12(2): 902-991.
Beal, et al., "An End-to-End Workflow for Engineering of Biological Networks from High-Level Specifications." ACS Synth. Biol. (2012); 1 (8): 317-331. Publication Date (Web): Jul. 10, 2012.
Becker, Daniel M., and Guarente, Leonard. "[12] High-efficiency transformation of yeast by electroporation." Methods in Enzymology (1991); 194: 182-187.
Bentley, David R., et al. "Accurate whole human genome sequencing using reversible terminator chemistry." Nature (2008); 456. 7218: 53-59.
Bernard, Philippe, et al. "The F plasmid CcdB protein induces efficient ATP-dependent DNA cleavage by gyrase." Journal of Molecular Biology (1993); 234.3: 534-541.
Bilitchenko, Al., "Eugene-a domain specific language for specifying and constraining synthetic biological parts, devices, and systems." PLOS ONE (2011); 6.4: e18882 (and Supplemental Data).
Boyd, J., et al. "Analysis of the diphtheria tox promoter by site-directed mutagenesis." Journal of Bacteriology (1988);170.12: 5949-5952.
Buchholz et al., "Platform Engineering of Corynebacterium glutamicum with Reduced Pyruvate Dehydrogenase Complex Activity for Improved Production of L-Lysine, L-Valine, and 2-Ketoisovalerate." Applied and Environmental Microbiology (2013); 79(18): 5566-5575.
Chakraborty, B. N., and Kapoor, M., "Transformation of filamentous fungi by electroporation." Nucleic Acids Research (1990); 18.22: 6737.
Chandran, et al., "TinkerCell: modular CAD tool for synthetic biology." Journal of Biological Engineering (2009); 3: 19, 17 pages.
Chen et al., "DeviceEditor visual biological CAD canvas." Journal of Biological Engineering (2012); 6:1, pp. 1-12.
Choi, J.H. et al., "Enhanced production of insulin-like growth factor I fusion protein in *Escherichia coli* by coexpression of the downregulated genes identified by transcriptome profiling." Appl. Environ. Microbiol. (2003); 69(8): 4737-4742.
Christiansen, Solveig K., et al. "Biolistic transformation of the obligate plant pathogenic fungus, *Erysiphe graminis* f. sp. hordei." Current Genetics (1995); 29.1: 100-102.
Christie, Peter J., and Gordon, Jay E. "The Agrobacterium Ti plasmids." Microbiology Spectrum (2014); 2.6.
Costanzo, Michael, et al. "The genetic landscape of a cell." Science (2010); 327 (5964): 425-431.
Cramer, Paula, et al. "Functional association between promoter structure and transcript alternative splicing." Proceedings of the National Academy of Sciences (1997); 94.21: 11456-11460.
Crameri, Andreas, et al. "Improved green fluorescent protein by molecular evolution using." Nat. Biotechnol (1996); 14.3: 315-319.
Crameri, Andreas, et al. "Construction and evolution of antibody-phage libraries by DMA shuffling." Nature Medicine (1996); 2.1: 100-102.
Crameri, Andreas, et al. "DNA shuffling of a family of genes from diverse species accelerates directed evolution." Nature (1998); 391.6664: 288-291.
Crameri, Andreas, et al. "Molecular evolution of an arsenate detoxification pathway by DNA shuffling." Nature Biotechnology (1997); 15.5: 436-438.
Czar, Michael J., et al. "Gene synthesis demystified." Trends in Biotechnology (2009); 27.2: 63-72.
Dahl, et al., "Multi-task Neural Networks for QSAR Predictions" Dept. of Computer Science, Univ. of Toronto, Jun. 2014, 21 pages (arXiv:1406.1231 [stat.ML]).
Dalphin, Mark E., et al. "TransTerm: A database of translational signals." Nucleic Acids Research (1996); 24.1: 216-218.
Damha, Masad J., et al. "An improved procedure for derivatization of controlled-pore glass beads for solid-phase oligonucleotide synthesis." Nucleic Acids Research (1990); 18.13 : 3813-3821.
Database EMBL [Online], "DNA fragment having promoter function." XP002767746, retrieved from EBI accession No. EM PAT:DD324094, Sep. 20, 2006.
Database Geneseq [Online] "Corynebacterium glutamicum DNA gyrase subunit B DNA, SEQ ID: 123." XP002767747, retrieved from EBI accession No. GSN: AEM36105. Mar. 8, 2007.
Database Geneseq [Online] "Corynebacterium glutamicum DNA gyrase subunit B DNA, SEQ ID: 123." XP002770467, retrieved from EBI accession No. GSN:AEM36105, Mar. 8, 2007.
Dauner, M., et al., "Intracellular carbon fluxes in riboflavin-producing Bacillus subtilis during growth on two-carbon substrate mixtures." Appl. Environ. Microbiol. (2002); 68(4): 1760-1771.
Drmanac, Radoje, et al. "Human genome sequencing using unchained base reads on self-assembling DNA nanoarrays." Science (2010); 327.5961: 78-81.
Duarte, N.C., et al., "Reconstruction and validation of *Saccharomyces scerevisiae* iND750, a fully compartmentalized genome-scale metabolic model." Genome Res. (2004); 14: 1298-1309.
Dunican, L.K. and Shivnan, E. "High frequency transformation of whole cells of amino acid producing coryneform bacteria using high voltage electroporation." Nature Biotechnology (1989); 7.10: 1067-1070.
Durand, Roger, et al. "Transient expression of the β-glucuronidase gene after biolistic transformation of the anaerobic fungus Neocallimastix frontalis." Current Genetics (1997); 31.2: 158-161.
Edwards, J.S. and Palsson, B.O., "Systems properties of the Haemophilus influenzae Rd metabolic genotype." J. Biol. Chem. (1999); 274(25): 17410-17416.
Edwards, J.S. and Palsson, B.O., "The *Escherichia coli* MG1655 in silico metabolic genotype: its definition, characteristics, and capabilities." Proc. Natl. Acad. Sci. U. S. A. (2000); 97(10): 5528-5533.
Eid, John, et al. "Real-time DNA sequencing from single polymerase molecules." Science (2009); 323.5910: 133-138.
Eikmanns, Bernhard J. "Identification, sequence analysis, and expression of a Corynebacterium glutamicum gene cluster encoding the three glycolytic enzymes glyceraldehyde-3-phosphate dehydrogenase, 3-phosphoglycerate kinase, and triosephosphate isomerase." Journal of Bacteriology (1992); 174.19: 6076-6086.

(56) References Cited

OTHER PUBLICATIONS

Eikmanns, Bernhard J., et al. "A family of Corynebacterium glutamicum/ Escherichia coli shuttle vectors for cloning, controlled gene expression, and promoter probing." Gene (1991); 102.1: 93-98.
Engler, Carola, et al. "A one pot, one step, precision cloning method with high throughput capability." PLOS ONE (2008); 3.11: e3647.
Fischer, S., et al., "The art of CHO cell engineering: A comprehensive retrospect and future perspectives." Biotechnology Advances (2015); 33: 1878-1896.
Fitzpatrick, R., et al. "Construction and characterization of recA mutant strains of Corynebacterium glutamicum and Brevibacterium lactofermentum." Applied Microbiology and Biotechnology (1994); 42.4: 575-580.
Förster, J., et al., "Genome-scale reconstruction of the Saccharomyces cerevisiae metabolic network." Genome Res. (2003); 13: 244-253.
Fox, Richard J., et al. "Improving catalytic function by ProSAR-driven enzyme evolution." Nature Biotechnology (2007); 25.3: 338-344.
Frewen, B., et al., "A Detailed, flexible model for sharing DNA concepts." IWBDA 2015, 7th International Workshop On Bio-Design Automation, University Of Washington, pp. 66-67, Aug. 19-21, 2015 (Presentation and Poster), 86 pages.
Gardner et al., "Production of Citric Acid by Mutants of Aspergillus niger." J. Gen. Microbial (1956); 14: 228-237.
Gietz, et al., "Improved method for high efficiency transformation of intact yeast cells." Nucleic Acids Res. (Mar. 1992); 20(6): 1425.
GenBank Accession No. CP010451.1 (Jan. 20, 2015), Corynebacterium glutamicum strain B253 DNA, complete genome, downloaded Jan. 12, 2018, 10 pages, https://www.ncbi.nlm.nih.gov/nuccore/748809780?sat=21&satkey=31610401.
GenBank CP001663.1, "*Mycobacterium smegmatis* str. MC2 155, complete genome." Jan. 31, 2014 (Jan. 31, 2014) [retrieved on Oct. 30, 2017, https://www.ncbi.nlm.nih.gov/nuccore/CP001663.1] genomic sequence nucleotide 4269453-4267996, 2 pages.
Gibson, Daniel G., et al. "Enzymatic assembly of DNA molecules up to several hundred kilobases." Nature Methods (2009); 6.5: 343-345.
Goosen, Theo, et al. "Transformation of Aspergillus niger using the homologous orotidine-5'-phosphate-decarboxylase gene." Current Genetics (1987); 11.6: 499-503.
GPU-Based Deep Learning Inference: A Performance and Power Analysis, NVidia Whitepaper, Nov. 2015, 12 pages.
Greger, Ingo H., et al. "Balancing transcriptional interference and initiation on the GAL7 promoter of *Saccharomyces cerevisiae*." Proceedings of the National Academy of Sciences (2000); 97.15: 8415-8420.
Guerrero, Carmen, et al. "Directed mutagenesis of a regulatory palindromic sequence upstream from the Brevibacterium lactofermentum tryptophan operon." Gene (1994); 138.1: 35-41.
Han, M.J. et al., "Engineering *Escherichia coli* for increased production of serine-rich proteins based on proteome profiling." Appl. Environ. Microbiol. (2003); 69(10): 5772-5781.
Han, M.J. et al., "Proteome analysis of metabolically engineered *Escherichia coli* cells producing poly(3-hydroxybutyrate)." J. Bacteriol. (2001); 183(1): 301-308.
Haynes, Jill A., and Britz, Margaret L. "The effect of growth conditions of Corynebacterium glutamicum on the transformation frequency obtained by electroporation." Microbiology (1990); 136. 2: 255-263.
Hermann, Thomas, et al. "Proteome analysis of Corynebacterium glutamicum." Electrophoresis (2001); 22.9: 1712-1723.
Hillson, N.J., "j5 DNA Assembly Design Automation Software." ACS Synthetic Biology (2011); 1: 14-21.
Hirao, et al., "L-Lysine production in continuous culture of an L-lysine hyperproducing mutant of Corynebacterium glutamicum." Applied Microbiology and Biotechnology (1989); 32 (3): 269-273.
Hong, Jiong, et al. "Cloning and functional expression of thermostable β-glucosidase gene from Thermoascus aurantiacus." Applied Microbiology and Biotechnology (2007); 73.6: 1331-1339.

Hong, S.H., et al., "The genome sequence of the capnophilic rumen bacterium Mannheimia succiniciproducens." Nat. Biotechnol. (2004); 22: 1275-1281.
Hui, A., et al. "Mutagenesis of the three bases preceding the start codon of the beta-galactosidase mRNA and its effect on translation in *Escherichia coli*." The EMBO Journal (1984); 3.3: 623-629.
Ikeda et al., "A genome-based approach to create a minimally mutated Corynebacterium glutamicum strain for efficient L-lysine production." J. Ind. Microbial. Biotechnol. (2006); 33(7): 610-615.
International Application No. PCT/US2016/065464, International Preliminary Report on Patentability, dated Jun. 12, 2018, 7 pages.
International Application No. PCT/US2016/065464, International Search Report and Written Opinion, dated Jun. 26, 2017, 14 pages.
International Application No. PCT/US2017/039997, International Preliminary Report on Patentability, dated Jan. 1, 2019, 8 pages.
International Application No. PCT/US2017/039997, International Search Report and Written Opinion, dated Nov. 9, 2017, 13 pages.
International Application No. PCT/US2017/039997, Invitation to Pay Additional Fees, dated Sep. 21, 2017, 3 pages.
Isojärvi, J., et al., "Draft Genome Sequence of Calothrix Strain 336/3, a Novel H2-Producing Cyanobacterium Isolated from a Finnish Lake." Genome Announcements (2015); 3 (1): 1-2, e01474-14.
Ito, Hisao, et al. "Transformation of intact yeast cells treated with alkali cations." Journal of Bacteriology (1983); 153.1: 163-168.
J5 DeviceEditor manual excerpt from https://j5.jbei.org/index.php/Main_Page_downloadedcontent available Apr. 19, 2016, 45 pages.
Jäger, W., et al. "Expression of the Bacillus subtilis sacB gene leads to sucrose sensitivity in the gram-positive bacterium Corynebacterium glutamicum but not in *Streptomyces lividans*." Journal of Bacteriology (1992); 174.16: 5462-5465.
Jensen, Peter Ruhdal and Hammer, Karin. "Artificial promoters for metabolic optimization." Biotechnology and Bioengineering (1998); 58.2-3: 191-195.
Jones, Jonathan DG, et al. "High level expression of introduced chimaeric genes in regenerated transformed plants." The EMBO Journal (1985); 4.10: 2411.
Jungwirth, Britta, et al. "Triple transcriptional control of the resuscitation promoting factor 2 (rpf2) gene of Corynebacterium glutamicum by the regulators of acetate metabolism RamA and RamB and the cAMP-dependent regulator GlxR." FEMS Microbiology Letters (2008); 281.2: 190-197.
Kabir, M.M. and Shimizu, K., "Fermentation characteristics and protein expression patterns in a recombinant *Escherichia coli* mutant lacking phosphoglucose isomerase for poly(3-hydroxybutyrate) production." Appl. Microbiol. Biotechnol. (2003); 62: 244-255.
Kadonaga, James T. "Regulation of RNA polymerase II transcription by sequence-specific DNA binding factors." Cell (2004); 116.2: 247-257.
Kashyap, Hirak, et al. "Big data analytics in bioinformatics: A machine learning perspective." Journal of Latex Class Files (2014); 13(9): 20 pages.
Khanna, N.C., et al. "Identification of the template binding polypeptide in the pea chloroplast transcriptional complex." Nucleic Acids Research (1992); 20.1: 69-74.
Khudyakov, Yu E., et al. "Effect of structure of the initiator codon on translation in *E. coli*." FEBS Letters (1998); 232.2: 369-371.
Kikuchi, Yoshimi, et al. "Functional analysis of the twin-arginine translocation pathway in Corynebacterium glutamicum ATCC 13869." Applied and environmental microbiology (2006); 72.11: 7183-7192.
Kim, Jae Bum, et al. "Polony multiplex analysis of gene expression (PMAGE) in mouse hypertrophic cardiomyopathy." Science (2007); 316.5830: 1481-1484.
Kimball, A., "The Data-Driven Future of Biotechnology." Zymergen, Machine learning, automation, and biotech, Strata + Hadoop World, Make Data Work conference, Presentation, London, UK, May 5, 2015, 49 pages http://cdn.oreillystatic.com/en/assets/1/event/132/The%20data-driven%20future%20of%20biotechnology%20Presentation.pdf.
Kirchner, Oliver and Tauch, Andreas. "Tools for genetic engineering in the amino acid-producing bacterium Corynebacteriumglutamicum." Journal of Biotechnology (2003); 104.1: 287-299.

(56) References Cited

OTHER PUBLICATIONS

Kotera, Ippei, et al. "A high-throughput and single-tube recombination of crude PCR products using a DNA polymerase inhibitor and type IIS restriction enzyme." Journal of Biotechnology (2008); 137.1: 1-7.

Kozlov, Igor A., et al. "Significant improvement of quality for long oligonucleotides by using controlled pore glass with large pores." Nucleosides, Nucleotides and Nucleic Acids (2005); 24.5-7: 1037-1041.

Krämer, O., et al., "Methods in mammalian cell line engineering: from random mutagenesis to sequence-specific approaches." Appl Microbiol Biotechnol (2010); 88: 425-436.

Krömer, J.O., et al., "In-depth profiling of lysine-producing Corynebacterium glutamicum by combined analysis of the transcriptome, metabolome, and fluxome." J. Bacteriol. (2004); 186(6): 1769-1784.

Kuo, Chih-Chung, et al., "The emerging role of systems biology for engineering protein production in CHO cells." Current Opinion in Biotechnology (2018); 51: 64-69.

Labarre, Jean, et al. "Gene replacement, integration, and amplification at the gdhA locus of Corynebacterium glutamicum." Journal of Bacteriology (1993); 175.4: 1001-1007.

Lee, et al., "A Highly Characterized Yeast Toolkit for Modular, Multipart Assembly." ACS Synthetic Biology (2015); 4(9): 975-986 (Published Apr. 14, 2015).

Lee, J.H., et al., "Global analyses of transcriptomes and proteomes of a parent strain and an L-threonine-overproducing mutant strain." J. Bacteriol. (2003); 185(18): 5442-5451.

Lee, Joo-Young, et al. "Adaptive evolution of Corynebacterium glutamicum resistant to oxidative stress and its global gene expression profiling." Biotechnology Letters (2013); 35.5: 709-717.

Lee, Sang Yup, et al., "Systems biotechnology for strain improvement." TRENDS in Biotechnology (2005); 23(7): 349-358.

Leng, Xiaoyan, et al. "Classification using functional data analysis for temporal gene expression data." Bioinformatics (2006); 22.1: 68-76.

Li, et al., "C-Brick: A New Standard for Assembly of Biological Parts Using Cpf1." ACS Synth. Biol. (2016); 5 (12): 1383-1388.

Libbrecht, Maxwell W., et al. "Machine learning applications in genetics and genomics." Nature Reviews Genetics (2015); 16.6: 321-332.

Linder, et al., "Phosphotransferase System-Independent Glucose Utilization in Corynebacterium glutamicum by Inositol Permeases and Glucokinases." Appl Environ Microbiol. (Jun. 2011); 77(11): 3571-3581.

Lindroth, Peter, and Mopper, Kenneth. "High performance liquid chromatographic determination of subpicomole amounts of amino acids by precolumn fluorescence derivatization withoff-phthaldialdehyde." Anal. Chem (1979); 51.11: 1667-1674.

Liu, et al., "Developing a high-throughput screening method for threonine overproduction based on an artificial promoter." Microbial Cell Factories (2015); 14: 121, 11 pages.

Makrides, Savvas C. "Strategies for achieving high-level expression of genes in *Escherichia coli*." Microbiological Reviews (1996); 60.3: 512-538.

Malumbres, Marcos, et al. "Codon preference in corynebacteria." Gene (1993); 134.1: 15-24.

Margulies, Marcel, et al. "Genome sequencing in microfabricated high-density picolitre reactors." Nature (2005); 437.7057: 376-380.

Martin, J. F., et al. "Cloning Systems in Amino Acid-Producing Corynebacteria." Nature Biotechnology (1987); 5.2: 137-146.

Menkel et al., "Influence of increased aspartate availability on lysine formation by a recombinant strain of Corynebacterium glutamicum and utilization of fumarate." Appl. Environ. Microbiol. (1989); 55(3): 684-688.

Mockel, Bettina, et al. "Functional and structural analyses of threonine dehydratase from Corynebacterium glutamicum." Journal of Bacteriology (1992);174.24: 8065-8072.

Mockel, Bettina, et al. "Threonine dehydratases of Corynebacterium glutamicum with altered allosteric control: their generation and biochemical and structural analysis." Molecular Microbiology (1994); 13.5: 833-842.

Molenaar, et al., "Biochemical and genetic characterization of the membrane-associated malate dehydrogenase (acceptor) from Corynebacterium glutamicum." Eur J Biochem. (1998); 254(2): 395-403.

Moore, Jeffrey C., et al. "Strategies for the in vitro evolution of protein function: enzyme evolution by random recombination of improved sequences." Journal of Molecular Biology (1997); 272.3: 336-347.

Murray, Elizabeth E. et al. "Codon usage in plant genes." Nucleic Acids Research (1989); 17.2: 477-498.

Nakashima, Nobutaka, et al. "Bacterial cellular engineering by genome editing and gene silencing." International Journal of Molecular Sciences (2014); 15.2: 2773-2793.

Neumann, Susanne, and Quiñones, Ariel. "Discoordinate gene expression of gyrA and gyrB in response to DNA gyrase inhibition in *Escherichia coli*." Journal of Basic Microbiology (1997); 37.1: 53-69.

Ohnishi et al., "A novel methodology employing Corynebacterium glutamicum genome information to generate a new L-lysine-producing mutant." Appl. Microbial Biotechnol (2002); 58(2): 217-223. Published online: Dec. 8, 2001.

Ohnishi, J. et al., "Efficient 40 degrees C fermentation of L-lysine by a new Corynebacterium glutamicum mutant developed by genome breeding." Appl. Microbiol. Biotechnol. (2003); 62: 69-75.

Paek, Se-Hwan, et al. "Development of rapid one-step immunochromatographic assay." Methods (2000); 22.1: 53-60.

Parry, Neil J., et al. "Biochemical characterization and mechanism of action of a thermostable β-glucosidase purified from Thermoascus aurantiacus." Biochemical Journal (2001); 353.1: 117-127.

Pátek, Miroslav, et al. "Promoters from Corynebacterium glutamicum: cloning, molecular analysis and search for a consensus motif." Microbiology (1996); 142.5: 1297-1309.

Pedersen and Phillips, "Towards programming languages for genetic engineering of living cells." J.R. Soc. Interface (2009); 6 (Suppl 4): S437-S450. Published online Apr. 15, 2009.

Peters-Wendisch, Petra G., et al. "Pyruvate carboxylase from Corynebacterium glutamicum: characterization, expression and inactivation of the pyc gene." Microbiology (1998); 144.4: 915-927.

Pfeifer-Sancar, Katharina, et al. "Comprehensive analysis of the Corynebacterium glutamicum transcriptome using an improved RNAseq technique." BMC Genomics (2013):14.1: 888, 23 pages.

Price, N.D., et al., "Genome-scale models of microbial cells: evaluating the consequences of constraints." Nat. Rev. Microbiol. (2004); 2: 886-897.

Prompramote, Supawan, et al. "Machine learning in bioinformatics." Bioinformatics Technologies. Springer Berlin Heidelberg (2005); pp. 117-153.

Qiu, Zhihao, et al. "The *Escherichia coli* polB Locus Is Identical to dinA, the Structural Gene for DNA Polymerase II Characterization of Pol II Purified From a polB Mutant." Journal of Biological Chemistry (1997); 272.13: 8611-8617.

Rastegari, Hilda et al., "Improvement in the Production of L-Lysine by Over-expression of Aspartokinase (ASK) in C. glutamicum ATCC-21799", Tropical Journal of Pharmaceutical Research, Feb. 2013, pp. 51-56, vol. 12, No. 1.

Reddy, Prasad, et al. "Translational efficiency of the *Escherichia coli* adenylate cyclase gene: mutating the UUG initiation codon to GUG or AUG results in increased gene expression." Proceedings of the National Academy of Sciences (1985); 82.17: 5656-5660.

Reed, J.L., et al., "An expanded genome-scale model of *Escherichia coli* K-12 (iJR904 GSM/GPR)." Genome Biol. (2003); 4, R54.

Reimer, et al., "High-Throughput Screening of a Corynebacterium glutamicum Mutant Library on Genomic and Metabolic Level." PLOS ONE (2014); 9(2): e86799, 12 pages.

Reinscheid, Dieter J., et al. "Stable expression of hom-1-thrB in Corynebacterium glutamicum and its effect on the carbon flux to threonine and related amino acids." Applied and Environmental Microbiology (1994); 60.1: 126-132.

(56) References Cited

OTHER PUBLICATIONS

Rey, Daniel Alexander, et al. "The putative transcriptional repressor McbR, member of the TetR-family, is involved in the regulation of the metabolic network directing the synthesis of sulfur containing amino acids in Corynebacterium glutamicum." Journal of Biotechnology (2003); 103.1: 51-65.

Reyrat, Jean-Marc, et al. "Counterselectable markers: untapped tools for bacterial genetics and pathogenesis." Infection and Immunity (1998); 66.9: 4011-4017.

Ricciardelli, Carmela, et al. "Development and characterization of primary cultures of smooth muscle cells from the fibromuscular stroma of the guinea pig prostate." In Vitro Cellular & Developmental Biology (1989); 25.11: 1016-1024.

Rückert, C., et al., "Genome-wide analysis of the L-methionine biosynthetic pathway in Corynebacterium glutamicum by targeted gene deletion and homologous complementation." J. Biotechnol. (2003); 104: 213-228.

Rytter, et al., "Synthetic promoter libraries for Corynebacterium glutamicum." Applied Microbiology and Biotechnology (2014); 98 (6): 2617-2623.

Sahm, Hermann, et al. "d-Pantothenate Synthesis in Corynebacterium glutamicum and Use of panBC and Genes Encoding I-Valine Synthesis ford-Pantothenate Overproduction." Applied and Environmental Microbiology (1999); 65.5: 1973-1979.

Sasaki, et al. "Simultaneous utilization of D-cellobiose, D-glucose, and D-xylose by recombinant Corynebacterium glutamicum under oxygen-deprived conditions." Applied Microbiology and Biotechnology (2008); 81.4: 691-699.

Schäfer, A., et al. "Increased fertility of Corynebacterium glutamicum recipients in intergeneric matings with *Escherichia coli* after stress exposure." Applied and Environmental Microbiology (1994); 60.2: 756-759.

Schäfer, Andreas, et al. "Small mobilizable multi-purpose cloning vectors derived from the *Escherichia coli* plasmids pK18 and pK19: selection of defined deletions in the chromosome of Corynebacterium glutamicum." Gene (1994); 145.1: 69-73.

Schilling, C.H., et al., "Genome-scale metabolic model of Helicobacter pylori 26695." J. Bacteriol. (2002); 184(16): 4582-4593.

Schrumpf, Barbel, et al. "A functionally split pathway for lysine synthesis in Corynebacterium glutamicium." Journal of Bacteriology (1991); 173.14: 4510-4516.

Schwarzer, Astrid, and Pühler, Alfred. "Manipuiation of Corynebacterium glutamicum by Gene Disruption and Replacement." Nature Biotechnology (1991); 9.1: 84-87.

Serwold-Davis, Theresa M., et al. "Localization of an origin of replication in Corynebacterium diphtheriae broad host range plasmid pNG2 that also functions in *Escherichia coli*." FEMS Microbiology Letters (1990) 66.1-3: 119-123.

Shevade, Shirish Krishnaj, et al. "A simple and efficient algorithm for gene selection using sparse logistic regression." Bioinformatics (2003); 19.17: 2246-2253.

Shuman, Stewart. "Novel approach to molecular cloning and polynucleotide synthesis using vaccinia DNA topoisomerase." Journal of Biological Chemistry (1994); 269.51: 32678-32684.

Sierzchala, Agnieszka B., et al. "Solid-phase oligodeoxynucleotide synthesis: a two-step cycle using peroxy anion deprotection." Journal of the American Chemical Society (2003); 125.44: 13427-13441.

Simon, R., et al. "A broad host range mobilization system for in vivo genetic engineering: transposon mutagenesis in gram negative bacteria." Nature Biotechnology (1983); 1.9: 784-791.

Snitkin and Segre, "Epistatic Interaction Maps Relative to Multiple Metabolic Phenotypes." PLoS Genet (2011); 7(2): e1001294.

Sonnen, Hans, et al. "Characterization of pGA1, a new plasmid from Corynebacterium glutamicum LP-6." Gene (1991); 107.1: 69-74.

Spackman, Darrel H., et al. "Automatic recording apparatus for use in the chromatography of amino acids." Analytical Chemistry (1958); 30: 1190-1206.

Spratt, Brian G., et al. "Kanamycin-resistant vectors that are analogues of plasmids pUC8, pUC9, pEMBL8 and pEMBL9." Gene (1986); 41.2: 337-342.

Stansen, Corinna, et al. "Characterization of a Corynebacterium glutamicum lactate utilization operon induced during temperature-triggered glutamate production." Applied and environmental microbiology (2005); 71.10: 5920-5928.

Stemmer, Willem P. "DNA shuffling by random fragmentation and reassembly: In vitro recombination for molecular evolution." Proceedings of the National Academy of Sciences (1994); 91.22: 10747-10751.

Stemmer, Willem P.C. "Rapid evolution of a protein in vitro by DNA shuffling." Nature (1994); 370.6488: 389-391.

Stemmer, Willem P.C. "The evolution of molecular computation." Science (1995); 270.5241: 1510-1511.

Stemmer, Willem P.C., "Searching Sequence Space" Nature Biotechnology (1995); 13: 549-553.

Stemmer, Willem P.C., et al. "Single-step assembly of a gene and entire plasmid from large numbers of oligodeoxyribonucleotides." Gene (1995); 164.1: 49-53.

Stenström, C. Magnus, et al. "Cooperative effects by the initiation codon and its flanking regions on translation initiation." Gene (2001); 273.2: 259-265.

Stephanopoulos, G., "Exploiting biological complexity for strain improvement through systems biology." Nat. Biotechnol. (2004); 22: 1261-1267.

Student. "The probable error of a mean." Biometrika (1908); 6(1): 1-25.

Su, Shin-San, et al. "*Escherichia coli* mutS-encoded protein binds to mismatched DNA base pairs." Proceedings of the National Academy of Sciences (1986); 83.14: 5057-5061.

Suda, Masako, et al. "Transcriptional regulation of Corynebacterium glutamicum methionine biosynthesis genes in response to methionine supplementation under oxygen deprivation." Applied Microbiology and Biotechnology (2008); 81.3: 505-513.

Sugimoto, Masakazu, et al. "Sequence analysis of functional regions of homoserine dehydrogenase genes from L-lysine and L-threonine-producing mutants of Brevibacterium lactofermentum." Bioscience, Biotechnology, and Biochemistry (1997); 61.10: 1760-1762.

Tauch, Andreas, et al. "Corynebacterium glutamicum DNA is subjected to methylation-restriction in *Escherichia coli*." FEMS Microbiology Letters (1994); 123.3: 343-347.

Tauch, Andreas, et al. "Plasmids in Corynebacterium glutamicum and their molecular classification by comparative genomics." Journal of Biotechnology (2003); 104.1: 27-40.

Tear, Crystal Jing Ying, et al. "Excision of Unstable Artificial Gene-Specific Inverted Repeats Mediates Scar-Free Gene Deletions in *Escherichia coli*." Applied Biochemistry and Biotechnology (2014); 175.4: 1858-1867.

Thierbach, Georg, et al. "Transformation of spheroplasts and protoplasts of Corynebacterium glutamicum." Applied Microbiology and Biotechnology (1998); 29.4: 356-362.

Third Party Observation filed in connection with International Application No. PCT/US2016/065465, dated Apr. 6, 2018, 12 pages.

Third-Party Submission filed with the U.S. Patent and Trademark Office on Dec. 7, 2017, in connection with U.S. Patent Application No. 15/396,230, 14 pages.

Third-Party Submission filed with the U.S. Patent and Trademark Office on May 1, 2018, in connection with U.S. Patent Application No. 15/140,296, 63 pages.

Tian, Jingdong, et al. "Advancing high-throughput gene synthesis technology." Molecular BioSystems (2009); 5.7: 714-722.

Trikka et al., "Iterative carotenogenic screens identify combinations of yeast gene deletions that enhance sclareol production." Microbial Cell Factories (2015); 14:60 (Published on line Apr. 24, 2015), 1:19, 19 pages.

Tsuchiya, Makoto, and Morinaga, Yasushi. "Genetic control systems of *Escherichia coli* can confer inducible expression of cloned genes in coryneform bacteria." Nature Biotechnology (1998); 6.4: 428-430.

(56) References Cited

OTHER PUBLICATIONS

Tummala, S.B. et al., "Transcriptional analysis of product concentration driven changes in cellular programs of recombinant Clostridium acetobutylicum strains." Biotechnol. Bioeng. (2003); 84, 842-854.
Vašicová, Pavla, et al. "Analysis of the Corynebacterium glutamicum dapA promoter." Journal of Bacteriology (1999);181.19: 6188-6191.
Voskuil, Martin I., et al. "The -16 region of Bacillus subtilis and other gram-positive bacterial promoters." Nucleic Acids Research (1998); 26.15: 3584-3590.
Wagner, Robert, et al. "Mutation detection using immobilized mismatch binding protein (MutS)." Nucleic Acids Research (1995); 23.19: 3944-3948.
Wang et al., "Programming cells by multiplex genome engineering and accelerated evolution." Nature (2009); 460: 894-898.
Wang, Junping, et al. "An improved recombineering approach by adding RecA to λ red recombination." Molecular Biotechnology (2006); 32.1: 43-53.
Weber, Ernst, et al. "Assembly of designer TAL effectors by Golden Gate cloning." PLOS ONE (2011); 6.5: e19722.
West, Steven and Proudfoot, Nicholas J. "Transcriptional termination enhances protein expression in human cells." Molecular Cell (2009); 33.3: 354-364.
West, Steven, et al. "Molecular dissection of mammalian RNA polymerase II transcriptional termination." Molecular Cell (2008); 29.5: 600-610.
Wilson, Erin H., et al., "Genotype specification language." ACS Synthetic Biology (2016); 5 (6): 471-478.
WIPO Communication dated Apr. 10, 2018 to Applicant, Zymergen Inc. in connection with International Application No. PCT/US2016/065465, advising of third party observation filed Apr. 6, 2018, 1 page.
Wittmann, C. and Heinzle, E., "Modeling and experimental design for metabolic flux analysis of lysine-producing Corynebacteria by mass spectrometry." Metab. Eng. (2001); 3: 173-191.
Yelton, M. Melanie, et al. "Transformation of Aspergillus nidulans by using a trpC plasmid." Proceedings of the National Academy of Sciences (1984); 81 (5): 1470-1474.
Yoon, S.H., et al., "Combined transcriptome and proteome analysis of *Escherichia coli* during high Cell density culture." Biotechnol. Bioeng. (2003); 81: 753-767.
Zetsche, et al., "Cpf1 Is a Single RNA-Guided Endonuclease of a Class 2 CRISPR-Cas System." Cell (2015); 163 (2): 759-771.
Zhang, Ji-Hu, et al. "Directed evolution of a fucosidase from a galactosidase by DNA shuffling and screening." Proceedings of the National Academy of Sciences (1997); 94 (9): 4504-4509.
Database Geneseq [Online] Sep. 26, 2001 (Sep. 26, 2001), "C glutamicum coding sequence fragment SEQ ID No. 1823.", retrieved from EBI accession No. GSN:AAH66788 Database accession No. AAH66788, 2 pages.
European Patent Application No. EP 17821246.0, Supplementary European Search Report, dated Jul. 1, 2019, 7 pages.
Frunzke, et al., "Co-ordinated regulation of gluconate catabolism and glucose uptake in Corynebacterium glutamicum by two functionally equivalent transcriptional regulators, GntR1 and GntR2". Molecular Microbiology (Jan. 2008); 67(2): 305-322. Epub Nov. 28, 2007.
Pérez-Redondo, et al., "The enigmatic lack of glucose utilization in Streptomyces clavuligerus is due to inefficient expression of the glucose permease gene". Microbiology (May 2010); 156(Pt 5): 1527-1537. Epub Jan. 28, 2010.

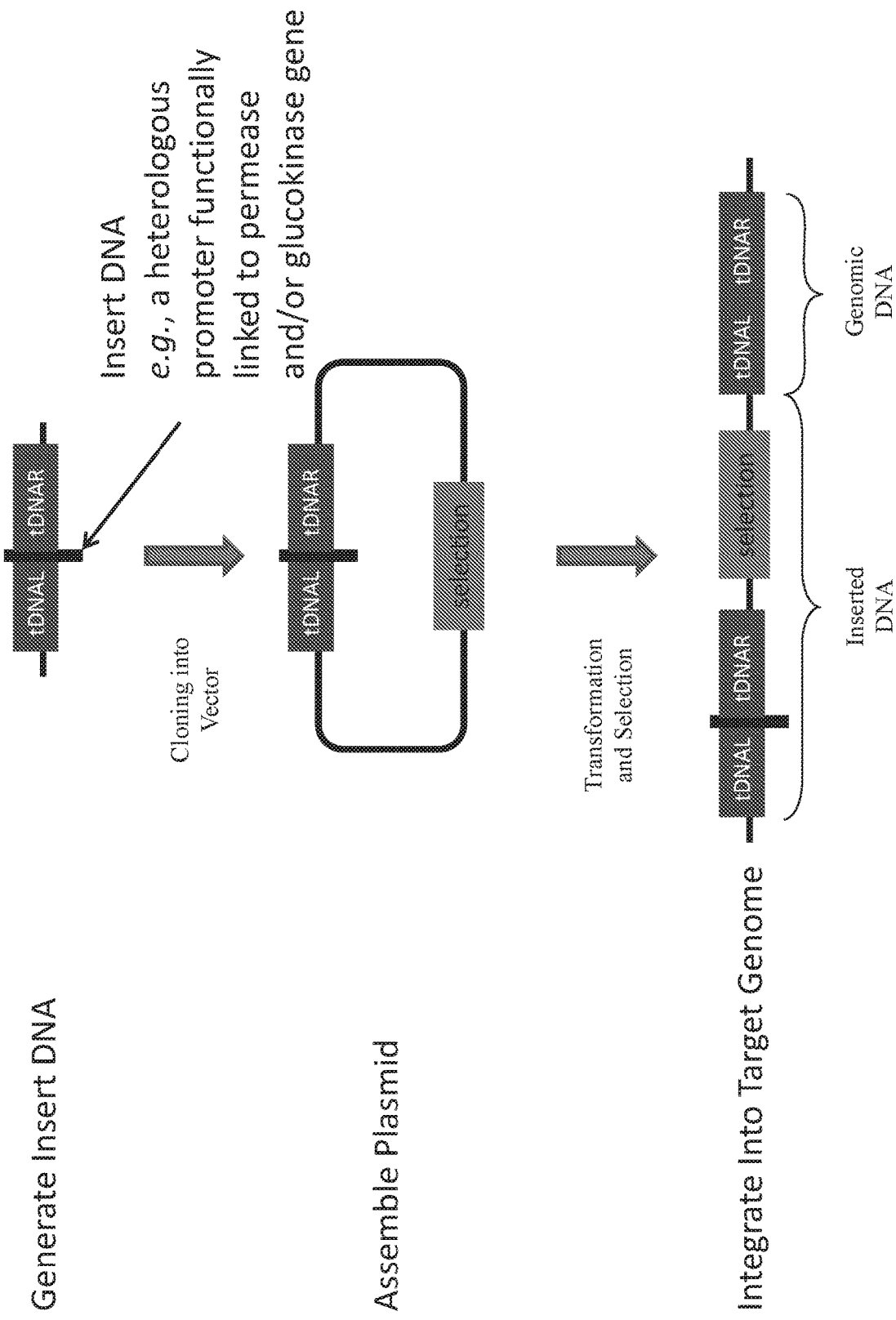

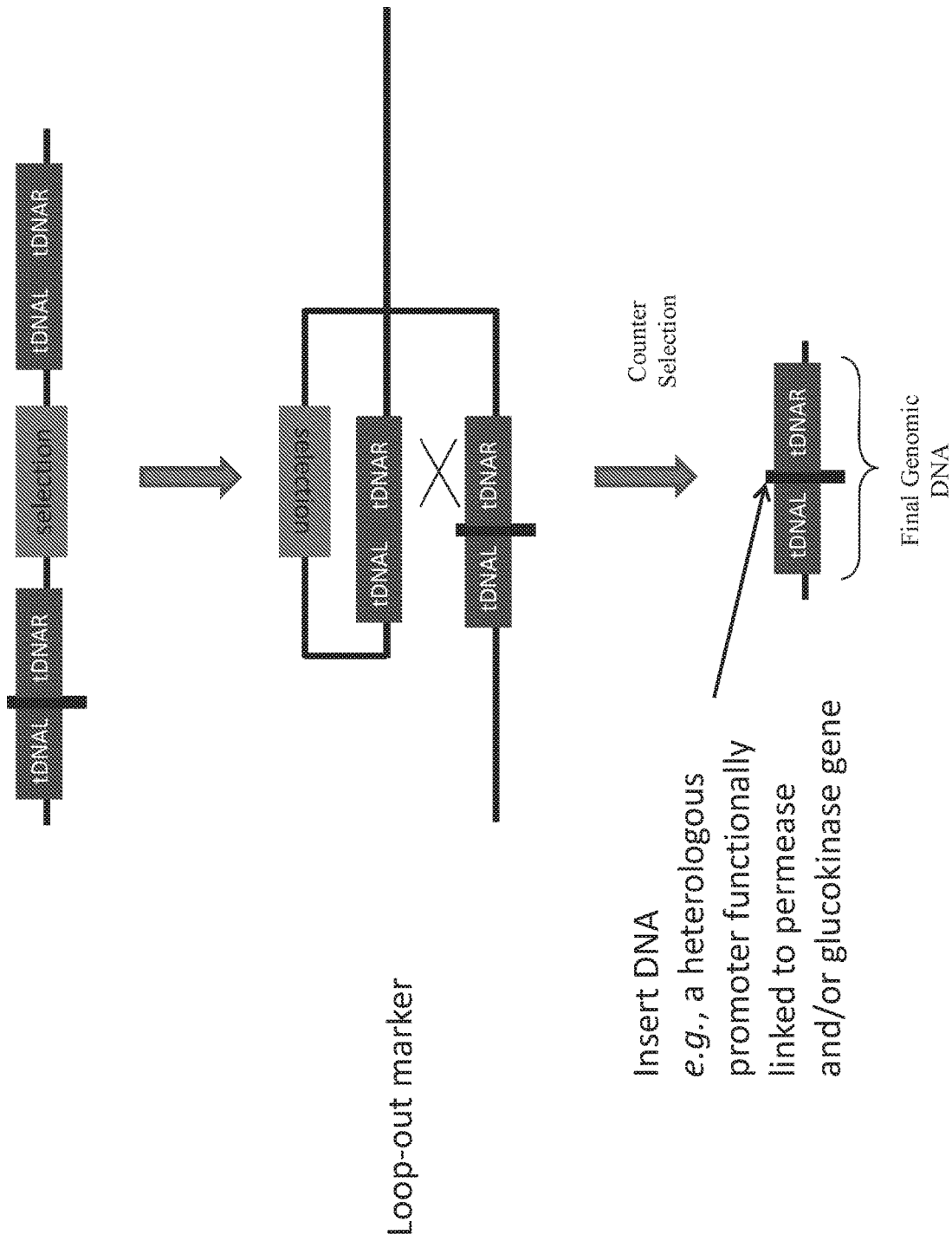

METHODS FOR GENERATING A GLUCOSE PERMEASE LIBRARY AND USES THEREOF

CROSS REFERENCE TO RELATED APPLICATONS

This application is a national phase of International Application No. PCT/US2017/039997, filed Jun. 29, 2017, which claims the benefit of priority from U.S. Provisional Application Ser. No. 62/356,924, filed Jun. 30, 2016, each of which is hereby incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ZYMR_005_01WO_SeqList_ST25.txt. The text file is 49 KB, was created on Jun. 28, 2017, and is being submitted electronically via EFS-Web.

FIELD

The present disclosure is directed to microbial genomic engineering. The disclosed genomic engineering method entails the generation of a library of glucose permease genes and/or glucokinase genes and introducing said library into microbial hosts in order to produce strains with a desired phenotype (e.g. microbial production of commercial products).

BACKGROUND

Glucose transport in some microorganisms such as, for example, *Corynebacterium glutamicum* is natively accomplished using the phosphotransferase transport system (PTS). In this system, phosphorylation of glucose is carried out simultaneously to transport. The phospho donor is phosphoenolpyruvate (PEP), therefore linking transport directly to glycolytic flux. In addition, the PTS system is natively regulated by a number of transcriptional processes in ways that are not always ideal for the production of commercial products.

Microbial processes for the production of various commercial products from glucose strive to maximize the efficiency with which the carbon skeleton of glucose is converted into the desired product. Control of glucose flux is critical for the production of products in ways that are dependent on the fermentation process, strain of microbial host being used (e.g., *C. glutamicum*), and small molecule being produced. If there is too much flux through glycolysis under high concentrations of glucose, glycolytic by-products (usually organic acids) are produced which decrease yield of product. If there is too little transport of glucose into the cell, then it is difficult to produce product at high rates. The genotypes of strains which are engineered in various ways to produce specific products interact with process conditions to lead to situations in which more or less glucose transport occurs than would be ideal to maximize yield or productivity.

Microbial strain improvement has been attempted by the expression of different glucose permeases and glucokinases which may alter glucose transport in such a way as to increase yield or productivity of commercial products. This has been demonstrated in a number of cases. For example, deletion of the native PTS system for glucose transport and overexpression of a native *C. glutamicum* permease along with a native *C. glutamicum* kinase led to the increased yield of lysine production from glucose (see Linder et al. Appl. Environ. Microbiol. June 2011 vol. 77, no. 11 pp 3571-3581, the contents of which are hereby incorporated by reference in their entirety). In another example, overexpression of the glucose permease and glucokinase from *Z. mobilis* in *C. glutamicum* was used for the production of small molecules (see U.S. Pat. No. 5,602,030, the contents of which are hereby incorporated by reference in its entirety).

However, the selection of a particular glucose permease to create the ideal level of glucose transport for a given metabolic process to produce a specific commercial product relies on a good understanding of a number of interacting factors, including the interaction of the genotype of a strain with the process environment in which fermentation takes place. Further, the correct expression, affinity, and transport rate, in combination with glucose and other carbon source concentrations may be required to deliver a balanced flux of glucose into the cell to match the flux through the pathway of interest. Understanding these parameters a priori and then choosing a single permease which embodies them can be difficult or impossible.

Thus, there is a great need in the art for new methods of engineering industrial microbes for producing specific commercial products, which do not suffer from the aforementioned drawbacks inherent with traditional strain improvement programs.

SUMMARY OF THE DISCLOSURE

In one aspect, provided herein is a host cell comprising a heterologous glucose permease gene functionally linked to a first promoter polynucleotide, wherein the first promoter polynucleotide comprises a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some cases, the glucose permease gene is a bacterial glucose permease gene. In some cases, the bacterial glucose permease gene is a gene that encodes a polypeptide sequence selected from SEQ ID NO: 13, SEQ ID NO: 10, SEQ ID NO: 11, SEQ ID NO: 12, SEQ ID NO: 9 and SEQ ID NO: 14. In some cases, the bacterial glucose permease gene is a gene with a nucleotide sequence selected from SEQ ID NO: 23, SEQ ID NO: 20, SEQ ID NO: 21, SEQ ID NO: 22, SEQ ID NO: 19 and SEQ ID NO: 24. In some cases, the host cell further comprises a hexokinase gene functionally linked to a second promoter polynucleotide, wherein the second promoter polynucleotide comprises a nucleotide sequence selected from SEQ ID NO: 2, SEQ ID NO: 1, SEQ ID NO: 3, SEQ ID NO: 4, SEQ ID NO: 5, SEQ ID NO: 6, SEQ ID NO: 7, and SEQ ID NO: 8. In some cases, the hexokinase gene is a glucokinase gene. In some cases, the glucokinase gene is a bacterial glucokinase gene. In some cases, the bacterial glucokinase gene is a gene that encodes a polypeptide with an amino acid sequence selected from SEQ ID NO: 15 and SEQ ID NO: 16. In some cases, the bacterial glucokinase gene is a gene with a nucleotide sequence selected from SEQ ID NO: 25 and SEQ ID NO: 26. In some cases, the first promoter polynucleotide and the second promoter polynucleotide are different. In some cases, the first promoter polynucleotide and the second promoter polynucleotide are identical. In some cases, the host cell belongs to the genus *Corynebacterium*. In some cases, the host cell is *Corynebacterium glutamicum*. In some cases, the host cell is used in a method of producing a biomolecule from glucose comprising culturing the host cell under conditions suitable for producing the biomolecule. In some cases, the biomolecule is a small molecule, a nucleotide, an amino acid, an organic acid, or an alcohol. In some cases, the amino acid is tyrosine, phenylalanine, tryptophan, aspartic acid, asparagine, threonine, isoleucine, methionine, or lysine. In some cases, the organic acid is succinate, lactate or pyruvate. In some cases, the alcohol is ethanol or isobutanol.

In another aspect, provided herein is a method for generating a microorganism capable of increased production of a biomolecule from glucose, the method comprising: a) genetically modifying a host microorganism, wherein the modifying comprises introducing a glucose permease gene from a library of glucose permease genes into the genome of the host microorganism, wherein each glucose permease gene from the library of glucose permease genes is functionally linked to a promoter comprising a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 and wherein the modification generates a strain of the host microorganism expressing the glucose permease gene; b) repeating step a) for a plurality of rounds until a plurality of strains of the host microorganism are generated, wherein each strain of the plurality of strains of the host microorganism expresses a separate glucose permease gene from the library of glucose permease genes; c) contacting each strain of the plurality of strains of the host microorganism with a carbon source comprising glucose under fermentative conditions; and d) selecting each strain of the host microorganism that produces an increased amount of a biomolecule from glucose as compared to the amount of the biomolecule produce from glucose from a control microorganism, wherein the control microorganism does not express a glucose permease gene from the library of glucose permease genes. In some cases, each of the glucose permease genes in the library of glucose permease genes is a bacterial glucose permease gene. In some cases, the library of bacterial glucose permease genes comprises genes that encode polypeptide sequences of SEQ ID NO: 13, SEQ ID NO: 10, SEQ ID NO: 11, SEQ ID NO: 12, SEQ ID NO: 9, SEQ ID NO: 14 or a combination thereof. In some cases, the library of bacterial glucose permease genes comprises genes with a nucleotide sequence of SEQ ID NO: 23, SEQ ID NO: 20, SEQ ID NO: 21, SEQ ID NO: 22, SEQ ID NO: 19, SEQ ID NO: 24 or a combination thereof. In some cases, the method further comprises introducing a hexokinase gene from a library of hexokinase genes, wherein each hexokinase gene from the library of hexokinase genes is functionally linked to a promoter polynucleotide, wherein the promoter polynucleotide comprises a sequence selected from SEQ ID NO: 2, SEQ ID NO: 1, SEQ ID NO: 3, SEQ ID NO: 4, SEQ ID NO: 5, SEQ ID NO: 6, SEQ ID NO: 7, and SEQ ID NO: 8. In some cases, the introduction of each hexokinase gene from the library of hexokinase genes is concurrent with the introduction of each glucose permease gene from the library of glucose permease genes. In some cases, each hexokinase gene from the library of hexokinase genes is present in a chimeric construct comprising a glucose permease gene from the library of glucose permease genes. In some cases, the hexokinase gene is a glucokinase gene. In some cases, the glucokinase gene is a bacterial glucokinase gene. In some cases, the library of bacterial glucokinase genes comprises genes that encode polypeptide sequences of SEQ ID NO: 15 and/or SEQ ID NO: 16. In some cases, the library of bacterial glucokinase genes comprises genes with nucleotide sequences of SEQ ID NO: 25 and/or SEQ ID NO: 26. In some cases, the promoter polynucleotide functionally linked to the glucose permease gene and the promoter polynucleotide functionally linked to the hexokinase gene are different. In some cases, the promoter polynucleotide functionally linked to the glucose permease gene and the promoter polynucleotide functionally linked to the hexokinase gene are identical. In some cases, the host microorganism belongs to the genus *Corynebacterium*. In some cases, the host microorganism is *Corynebacterium glutamicum*. In some cases, the introducing is performed by transformation, transduction or electroporation. In some cases, the biomolecule is a small molecule, an amino acid, a nucleotide, an organic acid, or an alcohol. In some cases, the amino acid is tyrosine, phenylalanine, tryptophan, aspartic acid, asparagine, threonine, isoleucine, methionine, or lysine. In some cases, the organic acid is succinate, lactate or pyruvate. In some cases, the alcohol is ethanol or isobutanol.

In yet another aspect, provided herein is a library of glucose permease genes, wherein each glucose permease gene in the library of glucose permease genes is functionally linked to a promoter comprising a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some cases, each glucose permease gene is a bacterial glucose permease gene. In some cases, the library of bacterial glucose permease genes comprises genes that encode polypeptide sequences of SEQ ID NO: 13, SEQ ID NO: 10, SEQ ID NO: 11, SEQ ID NO: 12, SEQ ID NO: 9, SEQ ID NO: 14 or a combination thereof. In some cases, the library of bacterial glucose permease genes comprises genes with nucleotide sequences of SEQ ID NO: 23, SEQ ID NO: 20, SEQ ID NO: 21, SEQ ID NO: 22, SEQ ID NO: 19, SEQ ID NO: 24 or a combination thereof. In some cases, each glucose permease gene in the library of glucose permease genes is a first portion of a chimeric construct, wherein the chimeric construct comprises a second portion, wherein the second portion is a hexokinase gene. In some cases, the hexokinase gene is functionally linked to a promoter polynucleotide, wherein the promoter polynucleotide comprises a sequence selected from SEQ ID NO: 2, SEQ ID NO: 1, SEQ ID NO: 3, SEQ ID NO: 4, SEQ ID NO: 5, SEQ ID NO: 6, SEQ ID NO: 7, and SEQ ID NO: 8. In some cases, the hexokinase gene is a glucokinase gene. In some cases, the glucokinase gene is a bacterial glucokinase gene. In some cases, the library of bacterial glucokinase genes comprises genes that encode polypeptide sequences of SEQ ID NO: 15 and/or SEQ ID NO: 16. In some cases, the library of bacterial glucokinase genes comprises genes with nucleotides sequences of SEQ ID NO: 25 and/or SEQ ID NO: 26. In some cases, the promoter polynucleotide functionally linked to the glucose permease gene and the promoter polynucleotide functionally linked to the hexokinase gene are different. In some cases, the promoter polynucleotide functionally linked to the glucose permease gene and the promoter polynucleotide functionally linked to the hexokinase gene are identical. In some cases, the library is used in a method of producing a biomolecule comprising introducing a glucose permease gene from the library into a host cell and culturing the host cell under conditions suitable for producing the biomolecule. In some cases, the biomolecule is an amino acid, a nucleotide, an organic acid, or an alcohol. In some cases, the amino acid is tyrosine, phenylalanine, tryptophan, aspartic acid, asparagine, threonine, isoleucine, methionine, or lysine. In some cases, the organic acid is succinate, lactate or pyruvate. In some cases, the alcohol is ethanol or isobutanol. In some cases, the host cell belongs to the genus *Corynebacterium*. In some cases, the host cell is *Corynebacterium glutamicum*. In some cases, the introducing is performed by transformation, transduction or electroporation.

In another aspect, provided herein is an isolated, synthetic or recombinant polynucleotide comprising a codon optimized polynucleotide selected from SEQ ID NO: 23, SEQ ID NO: 20, SEQ ID NO: 21, SEQ ID NO: 22, SEQ ID NO: 19 and SEQ ID NO: 24, wherein the polynucleotide is codon optimized for expression in a host cell. In some cases, the host cell is *E. coli* and/or *C. glutamicum*.

In a further aspect, provided herein is an isolated, synthetic or recombinant polynucleotide comprising a codon optimized polynucleotide selected from SEQ ID NO: 25 and SEQ ID NO: 26, wherein the polynucleotide is codon optimized for expression in a host cell. In some cases, the host cell is *E. coli* and/or *C. glutamicum*.

In yet another aspect, provided herein is an isolated, synthetic or recombinant polynucleotide comprising a first codon optimized polynucleotide and a second codon optimized polynucleotide, wherein the first polynucleotide and the second polynucleotide are each codon optimized for expression in a host cell, and wherein the first codon optimized polynucleotide encodes a polypeptide with glucose permease activity and the second codon optimized polynucleotide encodes a polypeptide with glucokinase activity. In some cases, the first codon optimized polynucleotide is selected from SEQ ID NO: 23, SEQ ID NO: 20, SEQ ID NO: 21, SEQ ID NO: 22, SEQ ID NO: 19 and SEQ ID NO: 24. In some cases, the second codon optimized polynucleotide is selected from SEQ ID NO: 25 and SEQ ID NO: 26. In some cases, the polypeptide with glucose permease activity comprises a sequence selected from SEQ ID NO: 13, SEQ ID NO: 10, SEQ ID NO: 11, SEQ ID NO: 12, SEQ ID NO: 9 and SEQ ID NO: 14. In some cases, the polypeptide with glucokinase activity comprises a sequence selected from SEQ ID NO: 15 and SEQ ID NO: 16. In some cases, the host cell is *E. coli* and/or *C. glutamicum*.

BRIEF DESCRIPTION OF THE FIGURES

FIG. 3 illustrates assembly of transformation plasmids of the present disclosure, and their integration into host organisms. The insert sequence insert DNA is generated by combining one or more synthesized oligonucleotides in an assembly reaction. DNA inserts contain desired promoter sequence flanked by direct repeat region (i.e., homology arms) designed for looping out DNA in subsequent steps. Assembled plasmids contain the insert DNA (permease gene and/or glucokinase gene functionally linked to promoters provided herein), and optionally, one or more selection markers.

FIG. 4 illustrates a procedure for looping-out selected regions of DNA from host strains. Direct repeat (DR) regions of the inserted DNA form a loop with corresponding sequences in the host strain's genome. Cells counter selected for selection marker exhibit DNA deletion of loop DNA.

DETAILED DESCRIPTION

Definitions

Figure 1:
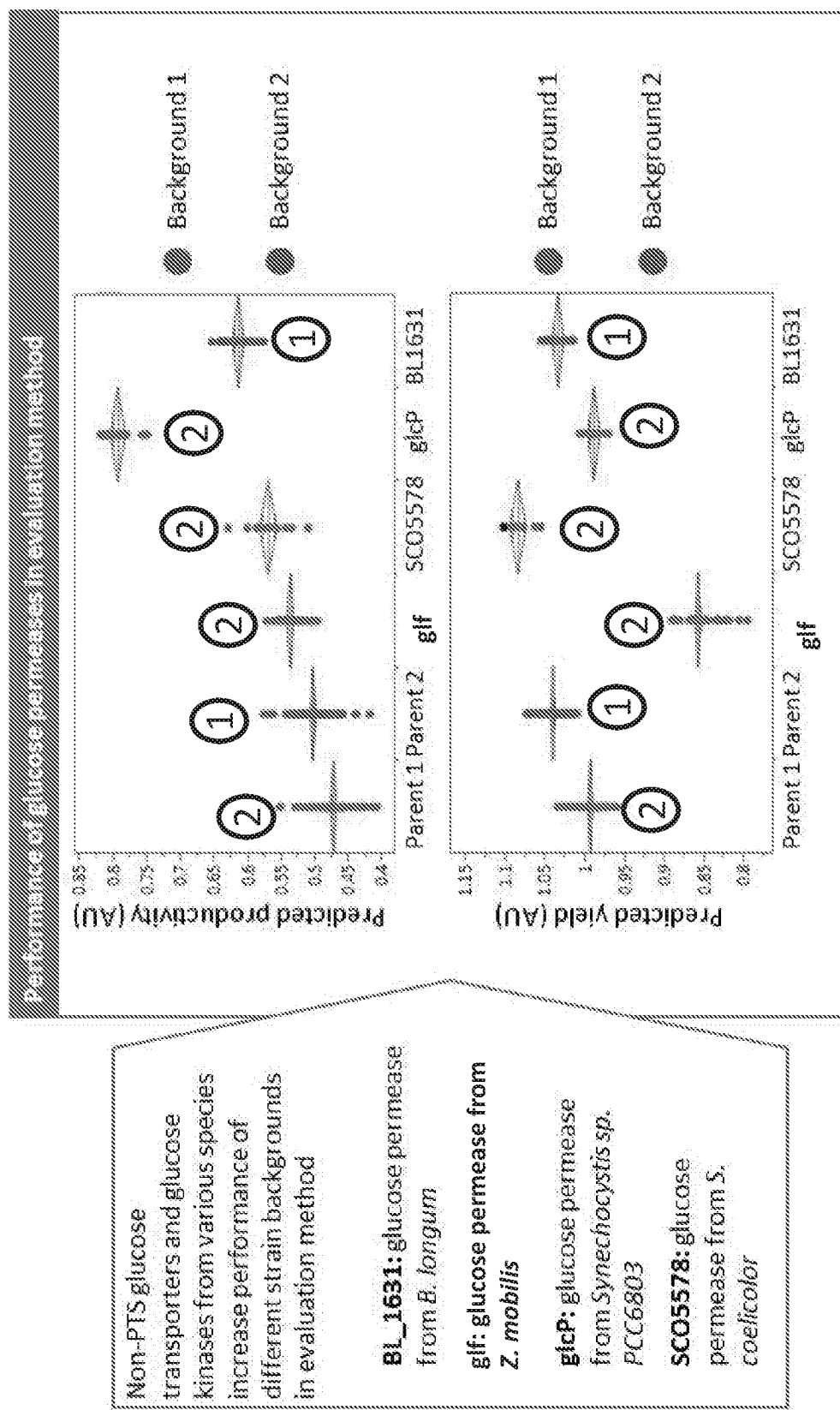
FIG. 1 illustrates performance of glucose permeases in evaluation method as described in Example 1.

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Unless the context requires otherwise, throughout the present specification and claims, the word "comprise" and variations thereof, such as, "comprises" and "comprising" are to be construed in an open, inclusive sense that is as "including, but not limited to".

Reference throughout this specification to "one embodiment" or "an embodiment" means that a particular feature, structure or characteristic described in connection with the embodiment may be included in at least one embodiment of the present disclosure. Thus, the appearances of the phrases "in one embodiment" or "in an embodiment" in various places throughout this specification may not necessarily all refer to the same embodiment. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

As used herein the terms "cellular organism" "microorganism" or "microbe" should be taken broadly. These terms can be used interchangeably and include, but may not be limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified microorganism," "recombinant microorganism," "recombinant host cell," and "recombinant strain" can be used interchangeably herein and can refer to microorganisms that have been genetically modified. Thus, the terms include a microorganism (e.g., bacteria, yeast cell, fungal cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring microorganism from which it was derived. It is understood that the terms refer not only to the particular recombinant microorganism in question, but also to the progeny or potential progeny of such a microorganism.

The term "wild-type microorganism" can describe a cell that occurs in nature, i.e. a cell that has not been genetically modified.

The term "genetically engineered" may refer to any manipulation of a microorganism's genome (e.g. by insertion or deletion of nucleic acids).

As used herein, the term "allele(s)" can mean any of one or more alternative forms of a gene, all of which alleles relate to at least one trait or characteristic. In a diploid cell, the two alleles of a given gene can occupy corresponding loci on a pair of homologous chromosomes. Since the present disclosure, in embodiments, relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype".

As used herein, the term "locus" (loci plural) can mean a specific place or places or a site on a chromosome where for example a gene or genetic marker is found.

As used herein, the term "genetically linked" can refer to two or more traits that are co-inherited at a high rate during breeding such that they are difficult to separate through crossing.

A "recombination" or "recombination event" as used herein can refer to a chromosomal crossing over or independent assortment. The term "recombinant" can refer to an organism having a new genetic makeup arising as a result of a recombination event.

As used herein, the term "phenotype" can refer to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence can refer to a nucleic acid, or a protein sequence, that links at least two heterologous polynucleotides, or two heterologous polypeptides, into a single macromolecule, or that can re-arrange one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" can be a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" can refer to a polymeric form of nucleotides of any length, either ribonucleotides or deoxyribonucleotides, or analogs thereof. This term can refer to the primary structure of the molecule, and thus includes double- and single-stranded DNA, as well as double- and single-stranded RNA. It can also include modified nucleic acids such as methylated and/or capped nucleic acids, nucleic acids containing modified bases, backbone modifications, and the like. The terms "nucleic acid" and "nucleotide sequence" can be used interchangeably.

As used herein, the term "gene" can refer to any segment of DNA associated with a biological function. Thus, genes can include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and can refer to related sequences that share a common ancestor or family member and are determined based on the degree of sequence identity. The terms "homology," "homologous," "substantially similar" and "corresponding substantially" can be used interchangeably herein. They can refer to nucleic acid fragments wherein changes in one or more nucleotide bases do not affect the ability of the nucleic acid fragment to mediate gene expression or produce a certain phenotype. These terms can also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure can encompass more than the specific exemplary sequences. These terms can describe the relationship between a gene found in one species, subspecies, variety, cultivar or strain and the corresponding or equivalent gene in another species, subspecies, variety, cultivar or strain. For purposes of this disclosure homologous sequences can be compared. "Homologous sequences" or "homologues" or "orthologs" can be thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "nucleotide change" can refer to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" can refer to, e.g., amino acid substitution, amino acid modification, deletion, and/or insertion, as is well understood in the art.

As used herein, the term "at least a portion" or "fragment" of a nucleic acid or polypeptide can mean a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used can depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide can generally be longer than 4 amino acids.

Variant polynucleotides also encompass sequences that can be derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual ($3^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR can include, but are not limited to, methods using paired primers, nested primers, single specific primers, degenerate primers, gene-specific primers, vector-specific primers, partially-mismatched primers, and the like.

The term "primer" as used herein can refer to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" can refer to hybridization conditions that affect the stability of hybrids, e.g., temperature, salt concentration, pH, formamide concentration and the like. These conditions can be empirically optimized to maximize specific binding and minimize non-specific binding of primer or probe to its target nucleic acid sequence. The terms as used can include reference to conditions under which a probe or primer will hybridize to its target sequence, to a detectably greater degree than other sequences (e.g. at least 2-fold over background). Stringent conditions can be sequence dependent and will be different in different circumstances. Longer sequences can hybridize specifically at higher temperatures. Generally, stringent conditions can be selected to be about 5° C. lower than the thermal melting point (Tm) for the specific sequence at a defined ionic strength and pH. The Tm can be the temperature (under defined ionic strength and pH) at which 50% of a complementary target sequence hybridizes to a perfectly matched probe or primer. Typically, stringent conditions may be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" can include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" or "promoter polynucleotide" can refer to a DNA sequence capable of controlling the expression of a coding sequence or functional RNA. The promoter sequence consists of proximal and more distal upstream elements, the latter elements can often be referred to as enhancers. Accordingly, an "enhancer" can be a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" can be used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. In some cases, a chimeric construct can be a recombinant construct comprising a plurality of regulatory (e.g., promoter) and coding sequences (e.g., glucose permease gene and hexokinase gene (glucokinase gene)). Each coding sequence in a chimeric construct comprising a plurality of coding sequences can be controlled by or functionally linked to a separate regulatory sequence. Such constructs described herein may be used by itself or may be used in conjunction with a vector. If a vector is used then the choice of vector can be dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" or "functionally linked" can mean in this context the sequential arrangement of the promoter polynucleotide according to the disclosure with a further oligo- or polynucleotide (e.g., glucose permease gene and/or glucokinase gene), resulting in transcription of said further polynucleotide (e.g., glucose permease gene and/or glucokinase gene). In other words, "operably linked" or "functionally linked" can mean the promoter controls the transcription of the gene (e.g. glucose permease gene and/or glucokinase gene) adjacent or downstream or 3' to said promoter.

The term "carbon source" generally can refer to a substance suitable to be used as a source of carbon for cell growth. Carbon sources can include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These can include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" can be defined as a raw material or mixture of raw materials supplied to a microorganism or fermentation process from which other products can be made. For example, a carbon source, such as biomass or the carbon compounds derived from biomass can be a feedstock for a microorganism that produces a product of interest (e.g. small molecule, peptide, synthetic compound, fuel, alcohol, etc.) in a fermentation process. However, a feedstock may contain nutrients other than a carbon source.

The term "volumetric productivity" or "production rate" can be defined as the amount of product formed per volume of medium per unit of time. Volumetric productivity can be reported in gram per liter per hour (g/L/h).

The term "specific productivity" can defined as the rate of formation of the product. To describe productivity as an inherent parameter of the microorganism and not of the fermentation process, productivity can herein further be defined as the specific productivity in gram product per gram of cell dry weight (CDW) per hour (g/g CDW/h). Using the relation of CDW to $OD_{600}$ for the given microorganism specific productivity can also be expressed as gram product per liter culture medium per optical density of the culture broth at 600 nm (OD) per hour (g/L/h/OD)

The term "yield" can be defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product.

The term "titre" or "titer" can be defined as the strength of a solution or the concentration of a substance in solution. For example, the titre of a product of interest (e.g. small molecule, peptide, synthetic compound, fuel, alcohol, etc.) in a fermentation broth can be described as g of product of interest in solution per liter of fermentation broth (g/L).

The term "total titer" can be defined as the sum of all product of interest produced in a process, including but not limited to the product of interest in solution, the product of interest in gas phase if applicable, and any product of interest removed from the process and recovered relative to the initial volume in the process or the operating volume in the process.

As used herein, the term "glucose permease" can refer to any transporter (e.g., myo-inositol transporter and/or glucose permease) that exhibits an affinity for glucose and subsequently facilitates its transport across the cell membrane of a host cell. The glucose permease can be a transmembrane protein. The transport can be passive transport whereby glucose diffuses in or out of the host cell as facilitated by the glucose permease. The glucose permease can be derived from a prokaryotic cell (i.e., Bacteria or Archaea) or a eukaryotic cell (e.g., a fungal cell). The prokaryotic glucose permease protein can be from any genus and species of bacteria or Archaea known in the art. The eukaryotic glucose permease protein can be, for example, from any genus and species of fungus known in the art. The term "bacterial glucose permease" as used herein can refer to a glucose permease as described herein derived from a bacteria.

As used herein, the term "glucose permease gene" can refer to any nucleic acid (e.g., genomic DNA, cDNA and/or mRNA) that when transcribed and/or translated encodes a glucose permease protein as described herein. The term "bacterial glucose permease gene" as used herein can refer to a bacterial glucose permease protein as described herein derived from a bacteria.

As used herein, the term "hexokinase" can refer to any protein derived from a prokaryotic cell (i.e., Bacteria or Archaea) or a eukaryotic cell (e.g., a fungal cell) that is an enzyme that can facilitate the phosphorylation of a hexose (six-carbon sugar). As provided herein, a hexokinase can be a glucokinase. As used herein, the term "glucokinase" can refer to any protein derived from a prokaryotic cell (i.e., Bacteria or Archaea) or a eukaryotic cell (e.g., a fungal cell) that is an enzyme that can facilitate the phosphorylation of glucose to glucose-6-phosphate. The prokaryotic hexokinase or glucokinase protein can be from any genus and species of bacteria or Archaea known in the art. The eukaryotic hexokinase or glucokinase protein can be, for example, from any genus and species of fungus known in the art. The term "bacterial hexokinase" as used herein can refer to a hexokinase as described herein derived from a bacteria. The term "bacterial glucokinase" as used herein can refer to a glucokinase as described herein derived from a bacteria.

As used herein, the "hexokinase gene" can refer to any nucleic acid (e.g., genomic DNA, cDNA and/or mRNA) that when transcribed and/or translated encodes a hexokinase protein as described herein. As used herein, the "glucokinase gene" can refer to any nucleic acid (e.g., genomic DNA, cDNA and/or mRNA) that when transcribed and/or translated encodes a glucokinase protein as described herein. The term "bacterial hexokinase gene" as used herein can refer to a bacterial hexokinase protein as described herein derived from a bacteria. The term "bacterial glucokinase gene" as used herein can refer to a bacterial glucokinase protein as described herein derived from a bacteria.

The term "product of interest" or "biomolecule" as used herein refers to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as: a microbial enzyme, including: catalase, amylase, protease, pectinase, glucose isomerase, cellulase, hemicellulase, lipase, lactase, streptokinase, and many others. The intracellular component may also include recombinant proteins, such as: insulin, hepatitis B vaccine, interferon, granulocyte colony-stimulating factor, streptokinase and others.

Overview

The present disclosure provides a microbial genomic engineering method that does not suffer from the myriad of problems associated with traditional microbial strain improvement programs.

One aspect provided herein is a method for generating a microorganism (e.g., bacteria) that is capable of increased production of a biomolecule or product of interest. In general, the methods for generating a microorganism for use in producing any biomolecule as provided herein can entail genetically modifying a host microorganism by introducing a member of a library of target genes into said host microorganism to generate a genomically engineered strain of said microorganism, culturing said engineered strain under conditions suitable to produce the biomolecule or product of interest, and selecting said engineered strain if said engineered strain produces an increased amount of the biomolecule or product of interest. The increased amount can be as compared to a wild-type strain of the host microorganism. The increased amount can be as compared to a strain of the host microorganism that does not contain a member of the library of target genes. The library of target genes can comprise a plurality of vectors, wherein each vector in the library comprises a chimeric construct comprising at least one promoter polynucleotide functionally linked or coupled to a target gene.

An exemplary workflow of one of the embodiments of the invention entails selecting a target gene, acquiring or synthesizing nucleic acid (e.g., DNA) for the target gene, and cloning said acquired or synthesized target gene into a suitable vector. Any method known in the art and/or provided herein can be used to assemble or clone the target gene or target genes into a suitable vector. The vector can be any vector known in the art and/or provided herein that is compatible with the host microorganism to be utilized. Once the vector comprising the target gene(s) is assembled, it can be introduced into the host microorganism. The introduction of the vector can be using any method known in the art and/or provided herein. The host microorganism can be any host microorganism provided herein. Once introduced into the host microorganism, genetically modified hosts can be selected and the insertion of the target gene(s) can be evaluated. The target gene(s) can be engineered to be inserted into specific locations of the host microorganism's genome. In some cases, the target gene(s) is inserted into a neutral site of the genome that facilitates expression of the target gene(s) without perturbing unintended pathways/processes within the host microorganism. In some cases, the target gene(s) replace specific gene(s) within the host microorganism. The specific gene can be the homologous target gene normally present in the host microorganism. The integration site, such as, for example, the neutral integration site can be determined empirically such that various sites can tested and a site that permits expression of the integrated target gene(s) without being detrimental to the host cell can be chosen. Integration into a desired site (e.g., neutral site) can be facilitated by cloning the target gene(s) into a vector comprising portions of sequence homologous to the desired integration site (i.e., homologous arms) and subsequently performing a recombination event in the host cell. The target gene(s) can be inserted between the portions of homologous sequence. In one embodiment, the vector comprises about 2 kb of sequence homologous to the desired integration site. The sequence homologous to the desired site can flank a glucose permease gene insert and/or glucose permease-glucokinase gene insert such that a first portion of the sequence is upstream (i.e., 5') of the gene insert and a second portion of the sequence is downstream (i.e., 3') of the gene insert. In another embodiment, the vector comprises about 4 kb of sequence homologous to the desired integration site. In this embodiment, the vector comprises about 2 kb of sequence homologous to the desired integration site upstream (i.e., 5') to a glucose permease gene insert and/or glucose permease-glucokinase gene insert and about 2 kb of sequence homologous to the desired integration site downstream (i.e., 3') to a glucose permease gene insert and/or glucose permease-glucokinase gene insert. In one embodiment, integration is performed by a single-cross-over integration and subsequent loop out of the plasmid backbone facilitated by counter-selection on a marker present in the vector backbone. In one embodiment, the target gene is any bacterial glucose permease gene known in the art and/or provided herein. In one embodiment, the target gene is any bacterial glucokinase gene known in the art and/or provided herein. In one embodiment, target genes are any bacterial glucose permease gene known in the art and/or provided herein and any bacterial glucokinase gene known in the art and/or provided herein.

Evaluation of the insertion can be performed using any method know in the art such as, for example, amplifying and/or sequencing of the genetically modified microorganism's genome or portions thereof. In some cases, the methods provided herein also entail the removal or looping out of selection markers through counter selection as described herein. The looping out can be performed using any of the methods provided herein.

Following the evaluation of the insertion of the target gene(s) and, optional, removal of selection markers, the genetically modified strain can be evaluated for its ability to produce a biomolecule or product of interest. Prior to evaluation an optional step can be expanding the strain. Expansion can entail culturing the genetically modified strain on plates or in wells in a multi-well plate in growth media suitable for expansion. The evaluation step can entail culturing the genetically modified strain on plates or in wells in a multi-well plate comprising growth media/conditions designed to mimic actual conditions for producing a biomolecule or product of interest. In some cases, the growth media in this step is suitable for the production of biomolecules or products of interest derived from the metabolic processing of glucose. If the genetically modified strain possesses or is predicted to produce a desired or threshold rate of production or yield of the biomolecule or product of interest as determined from the evaluation step, the strain can be selected and placed in cold storage. The prediction can be based on measuring the amount of product of interest and biomass formed at various time points during culturing of the strain and using said measurements to predict how said strain will perform under expanded or larger scale conditions (e.g., fermentation conditions). In one embodiment, the prediction is based on a linear regression analysis of the performance of the strain during the evaluation method.

In some cases, a genetically modified strain possessing or predicted to produce a desired or threshold rate of production or yield of the biomolecule or product of interest is transferred to or grown in a larger culture under conditions for producing the biomolecule or product of interest (e.g., fermentation conditions). This step can be used in order to determine if the selected strain can perform as predicted under actual conditions for the production of the biomolecule or product of interest. In some cases, the steps provided herein for the introduction and evaluation of each target gene from a library of target genes such as those provided herein are repeated for each target gene from the library in order to select one or more strains of genetically modified microorganisms that produce a desired or threshold yield and/or productivity rate of a biomolecule or product of interest.

In one embodiment, the biomolecule or product of interest is derived from glucose and the metabolic processing thereof by the microorganism such that the methods provided herein entail the generation of a strain or strains of microorganisms that produce an increased amount of a biomolecule or product of interest derived from the metabolic processing of glucose by the strain or strains. In one embodiment, the methods provided herein entail the introduction of one or more target genes involved in glucose transport and/or metabolism. In one embodiment, the one or more target genes are utilized in a phosphotransferase system (PTS). In one embodiment, the target gene is a glucose permease gene such that a glucose permease gene is introduced into the host microorganism in the methods provided herein. The glucose permease gene can be a heterologous gene in the host microorganism. In one embodiment, the target gene is a hexokinase gene such that a hexokinase gene is introduced into the host microorganism in the methods provided herein. In one embodiment, both a glucose permease gene and a hexokinase gene are introduced into the host microorganism in the methods provided herein. In one embodiment, the introduction of a glucose permease gene and/or hexokinase gene into the host microorganism produces a non-PTS recombinant glucose uptake system in the host microorganism. The recombinant glucose uptake system can serve to uncouple glucose transport from phosphoenolpyruvate (PEP) utilization, thereby producing more PEP for the synthesis of biomolecules or products of interest. The biomolecules or products of interest produced by the methods provided herein can be any commercial product produced from glucose. In some cases, the biomolecule or product of interest is a small molecule, an amino acid, an organic acid, or an alcohol. The amino acid can be tyrosine, phenylalanine, tryptophan, aspartic acid, asparagine, threonine, isoleucine, methionine, or lysine. The organic acid can be succinate, lactate or pyruvate. The alcohol can be ethanol or isobutanol.

In one embodiment, the disclosed microbial genomic engineering method utilizes a library of glucose permease genes and/or hexokinase genes. A glucose permease gene can be selected based on the glucose permeases affinity for glucose and/or glucose transport rate. In some cases, the microbes are engineered utilizing a glucose permease library, a hexokinase (e.g., glucokinase) library or a combination of glucose permease and hexokinase (e.g., glucokinase) libraries. In one embodiment, the library contains a plurality of chimeric construct inserts such that each insert in the library comprises a glucose permease gene and a hexokinase (e.g., glucokinase) gene. Following engineering, the microbes can be efficiently screened or evaluated for resultant outcome, e.g. production of a product from glucose as provided herein. This process of utilizing the libraries provided herein to define particular genomic alterations and then testing/screening host microbial genomes harboring the alterations can be implemented in an efficient and iterative manner and can be used to identify specific combinations of glucose permease/hexokinase genes (e.g., glucokinase genes) whose expression in a host cell produces a desired or threshold level of a biomolecule or product of interest form glucose.

In one embodiment, each glucose permease gene or hexokinase gene (glucokinase gene) as provided herein for use in the methods provided herein is under the control of or functionally linked to a native promoter or any of the promoter polynucleotides provided herein. A "promoter polynucleotide" or a "promoter" or a "polynucleotide having promoter activity" can mean a polynucleotide, preferably deoxyribopolynucleotide, or a nucleic acid, preferably deoxyribonucleic acid (DNA), which when functionally linked to a polynucleotide to be transcribed determines the point and frequency of initiation of transcription of the coding polynucleotide (e.g., glucose permease gene or glucokinase gene), thereby enabling the strength of expression of the controlled polynucleotide to be influenced. In one embodiment, each glucose permease gene and/or hexokinase gene (e.g., glucokinase gene) in a library comprising glucose permease genes and/or hexokinase genes (e.g., glucokinase genes) is under the control of the same or an identical promoter. In one embodiment, each glucose permease gene and/or hexokinase gene (e.g., glucokinase gene) in a library comprising glucose permease genes and/or hexokinase genes (e.g., glucokinase genes) is under the control of separate or different promoter. In yet another embodiment, each target gene in a chimeric construct in a library of chimeric constructs comprising the target genes are under the control of the same or an identical promoter. In a further embodiment, each target gene in a chimeric construct in a library of chimeric constructs comprising the target genes are under the control of a separate or different promoter.

In one embodiment, provided herein is a promoter ladder for use in generating a library of glucose permease genes or hexokinase genes or glucokinase genes. The term "promoter ladder" as used herein refers to a plurality of promoters with incrementally increasing levels of promoter activity. The term "promoter activity" as used herein refers to the ability of the promoter to initiate transcription of a polynucleotide sequence into mRNA. Methods of assessing promoter activity are well known to those of skill in the art and can include, for example the methods described in Example 2 of U.S. 62/264,232, filed on Dec. 7, 2015 and PCT/US16/65464 (i.e., PCT Publication No. WO2017/100376), each of which is herein incorporated by references in its entirety. The term "constitutive promoter" as used herein can refer to a promoter that directs the transcription of its associated genes at a constant rate regardless of the internal or external cellular conditions.

Promoters

In some embodiments, the present disclosure teaches methods of selecting promoters with optimal expression properties to modulate RNA degradation function and produce beneficial effects on overall-host strain productivity.

Promoters regulate the rate at which genes are transcribed and can influence transcription in a variety of ways. Constitutive promoters, for example, direct the transcription of their associated genes at a constant rate regardless of the internal or external cellular conditions, while regulatable promoters increase or decrease the rate at which a gene is transcribed depending on the internal and/or the external cellular conditions, e.g. growth rate, temperature, responses to specific environmental chemicals, and the like. Promoters can be isolated from their normal cellular contexts and engineered to regulate the expression of virtually any gene, enabling the effective modification of cellular growth, product yield and/or other phenotypes of interest.

In some embodiments, the present disclosure teaches methods of identifying one or more promoters and/or generating variants of one or more promoters within a host cell, which exhibit a range of expression strengths (e.g. promoter ladders discussed infra), or superior regulatory properties (i.e., tighter regulatory control for selected genes). A particular combination of these identified and/or generated promoters can be grouped together as a promoter ladder for use in the RNA degradation perturbation experiments explained in more detail below.

In some embodiments, promoter ladders are created by identifying natural, native, or wild-type promoters associated with a target gene of interest that have a range of expression strengths. These identified promoters can be grouped together as a promoter ladder.

In some embodiments, promoter ladders are created by: identifying natural, native, or wild-type promoters associated with a target gene of interest and then mutating said promoter to derive multiple mutated promoter sequences. Each of these mutated promoters is tested for effect on target gene expression. In some embodiments, the edited promoters are tested for expression activity across a variety of conditions, such that each promoter variant's activity is documented/characterized/annotated and stored in a database. The resulting edited promoter variants are subsequently organized into promoter ladders arranged based on the strength of their expression (e.g., with highly expressing variants near the top, and attenuated expression near the bottom, therefore leading to the term "ladder").

In some embodiments, the present disclosure teaches promoter ladders that are a combination of identified naturally occurring promoters and mutated variant promoters.

In some embodiments, the present disclosure teaches methods of identifying natural, native, or wild-type promoters that satisfied both of the following criteria: 1) represented a ladder of constitutive promoters; and 2) could be encoded by short DNA sequences, ideally less than 100 base pairs. In some embodiments, constitutive promoters of the present disclosure exhibit constant gene expression across two selected growth conditions (typically compared among conditions experienced during industrial cultivation). In some embodiments, the promoters of the present disclosure will consist of a ~60 base pair core promoter, and a 5' UTR between 26- and 40 base pairs in length.

In some embodiments, one or more of the aforementioned identified naturally occurring promoter sequences are chosen for gene editing. In some embodiments, the natural promoters are edited via any known genetic mutation methods. In other embodiments, the promoters of the present disclosure are edited by synthesizing new promoter variants with the desired sequence.

The entire disclosures of U.S. Patent Application No. 62/264,232, filed on Dec. 7, 2015, and PCT/US16/65464 (PCT Publication No. WO2017/100376), filed Dec. 7, 2016 are each hereby incorporated by reference in its entirety for all purposes.

A non-exhaustive list of the promoters of the present disclosure is provided in Table 1 below. Each of the promoter sequences in Table 1 can be referred to as a heterologous promoter or heterologous promoter polynucleotide.

TABLE 1

Selected promoter sequences of the present disclosure.

| SEQ ID No. | Promoter Short Name |
|---|---|
| 1 | P1 |
| 2 | P2 |
| 3 | P3 |
| 4 | P4 |
| 5 | P5 |
| 6 | P6 |
| 7 | P7 |
| 8 | P8 |

In some embodiments, the promoters of the present invention exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a promoter sequences from Table 1.

Glucose Permeases

Provided herein is a library of glucose permease genes for use in the methods provided herein. The library of glucose permease genes can comprise one or more glucose permease genes. Each glucose permease gene in the library can be a native form of the glucose permease gene or a mutated form. The mutated form can comprise one or more mutations selected from an insertion, deletion, single nucleotide polymorphism (SNP), or translocation. Each glucose permease gene in the library can be a bacterial glucose permease gene. The glucose permease gene can be any glucose permease gene from a prokaryotic cell (i.e., Bacteria and/or Archaea) known in the art. The glucose permease gene can be any glucose permease gene from a eukaryotic cell (e.g., fungal) known in the art. A glucose permease can be considered any protein comprising glucose permease activity. For example, a glucose permease for use herein can be any transporter (e.g., myo-inositol transporter) that exhibits an affinity for glucose and subsequently facilitates its transport across the cell membrane of a host cell. The host cell can be any host cell provided herein. In one embodiment, the library of glucose permease genes comprises glucose permease genes from any strain/species/sub-species of *Mycobacterium* (e.g., *Mycobacterium smegmatis*), *Streptomyces* (e.g., *Streptomyces coelicolor*), *Zymomonas* (e.g., *Zymomonas mobilis*), *Synechocystis* (e.g., *Synechocystis* sp. PCC6803), *Bifidobacterium* (e.g., *Bifidobacterium longum*), *Escherichia* (e.g., *Escherichia coli*), *Bacillus* (e.g., *Bacillus subtilis*), *Corynebacterium* (e.g., *Corynebacterium glutamicum*), *Saccharomyces* (e.g., *S. cerevisiae*) or a combination thereof. In one embodiment, the library of glucose permease genes comprises glucose permease genes that encode polypeptide sequences selected from SEQ ID NO: 9, SEQ ID NO: 10, SEQ ID NO: 11, SEQ ID NO: 12, SEQ ID NO: 13, SEQ ID NO: 14 or a combination thereof.

In some embodiments, the permeases of the present invention exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a permease provided herein.

In one embodiment, the library of glucose permease genes comprises glucose permease genes selected from SEQ ID NO: 19, SEQ ID NO: 20, SEQ ID NO: 21, SEQ ID NO: 22, SEQ ID NO: 23, SEQ ID NO: 24 or a combination thereof.

In some embodiments, the permease genes of the present invention exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a permease gene provided herein.

Each glucose permease in the library can be functionally linked or under the control of its native promoter or a mutated form of its native promoter. Each glucose permease gene in the library can be functionally linked to or controlled by any promoter provided herein. Each glucose permease gene in the library can be controlled by a promoter polynucleotide sequence that comprises a sequence selected from SEQ ID NO: 1, SEQ ID NO: 2, SEQ ID NO: 3, SEQ ID NO: 4, SEQ ID NO: 5, SEQ ID NO: 7, and SEQ ID NO: 8. Each glucose permease gene in the library can be controlled by a promoter polynucleotide sequence that contains a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In one embodiment, each glucose permease gene in the library is present as a set of glucose permease genes, wherein each set has one glucose permease gene functionally linked to SEQ ID NO. 1, one glucose permease gene functionally linked to SEQ ID NO. 2, one glucose permease gene functionally linked to SEQ ID NO. 3, one glucose permease gene functionally linked to SEQ ID NO. 4, one glucose permease gene functionally linked to SEQ ID NO. 5, one glucose permease gene functionally linked to SEQ ID NO. 6, one glucose permease gene functionally linked to SEQ ID NO. 7 and one glucose permease gene functionally linked to SEQ ID NO. 8 or a combination thereof. Each glucose permease gene in a library of glucose permease genes can be present in a chimeric construct such that the gene can be flanked by one or more regulatory sequences and/or sequence homologous to sequence present in the genome of a host cell. The sequence homologous to sequence present in the host cell can facilitate integration of the glucose permease gene into a site or locus of the host cell genome that comprises complementary sequence. Integration can be via a recombination event. The regulatory sequence can be any regulatory sequence known in the art or provided herein such as, for example, a promoter, start, stop, signal, secretion and/or termination sequence used by the genetic machinery of the host cell.

Hexokinases

Provided herein is a library of hexokinase genes for use in the methods provided herein. The library of hexokinase genes can comprise one or more hexokinase genes. Each hexokinase gene in the library can be a native form or a mutated form of the gene. The mutated form can comprise one or more mutations selected from an insertion, deletion, single nucleotide polymorphism (SNP), or translocation. Each hexokinase gene can be a glucokinase gene. Each glucokinase gene in the library can be a bacterial glucokinase gene. The glucokinase gene can be any glucokinase gene from a prokaryotic cell (i.e., Bacteria and/or Archaea) known in the art. The glucokinase gene can be any glucokinase gene from a eukaryotic cell (e.g., fungal) known in the art. A glucokinase can be considered any kinase known in the art that can utilize glucose as a substrate and phosphorylate glucose to produce glucose-6-phosphate. In one embodiment, the library of glucokinase genes comprises glucokinase genes from any strain/species/sub-species of *Corynebactium* (e.g., *C. glutamicum*), *Zymomonas* (e.g., *Zymomonas mobilis*), *Staphylococcus* (e.g., *S. aureus* glkA), *Enterococcus* (e.g., *E. faecalis*), *Escherichia* (e.g., *E. coli*), *Clostridium* (e.g., *C. difficile*), *Streptococcus* (e.g., *S. pneumonia*), *Bacillus* (e.g., *B. anthracis*), *Renibacterium* (e.g., *R. salmoninarium*), *Saccharomyces* (e.g., *S. cerevisiae*) or a combination thereof. In one embodiment, the library of glucokinase genes comprises glucokinase genes that encode polypeptide sequences selected from SEQ ID NO: 15 and/or SEQ ID NO: 16.

In some embodiments, the hexokinases (e.g., glucokinases) of the present invention exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a hexokinase (e.g., glucokinase) provided herein.

In one embodiment, the library of glucokinase genes comprises glucokinase genes selected from SEQ ID NO: 25 and/or SEQ ID NO: 26.

In some embodiments, the hexokinase genes (e.g., glucokinase genes) of the present invention exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a hexokinase gene (e.g., glucokinase gene) provided herein.

Each hexokinase gene (e.g., glucokinase gene) in the library can be functionally linked or under the control of its native promoter or a mutated form of its native promoter. Each hexokinase gene (e.g., glucokinase gene) in the library can be functionally linked to or controlled by any promoter provided herein. Each hexokinase gene (e.g., glucokinase gene) in the library can be controlled by a promoter polynucleotide sequence that comprises a sequence selected from SEQ ID NO: 1, SEQ ID NO: 2, SEQ ID NO: 3, SEQ ID NO: 4, SEQ ID NO: 5, SEQ ID NO: 7, and SEQ ID NO: 8. Each hexokinase gene (e.g., glucokinase gene) in the library can be controlled by a promoter polynucleotide sequence that contains a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In one embodiment, each hexokinase gene (e.g., glucokinase gene) in the library is present as a set of hexokinase genes (e.g., glucokinase genes), wherein each set has one hexokinase gene (e.g., glucokinase gene) functionally linked to SEQ ID NO. 1, one hexokinase gene (e.g., glucokinase gene) functionally linked to SEQ ID NO. 2, one hexokinase gene (e.g., glucokinase gene) functionally linked to SEQ ID NO. 3, one hexokinase gene (e.g., glucokinase gene) functionally linked to SEQ ID NO. 4, one hexokinase gene (e.g., glucokinase gene) functionally linked to SEQ ID NO. 5, one hexokinase gene (e.g., glucokinase gene) functionally linked to SEQ ID NO. 6, one hexokinase gene (e.g., glucokinase gene) functionally linked to SEQ ID NO. 7 and one hexokinase gene (e.g., glucokinase gene) functionally linked to SEQ ID NO. 8 or a combination thereof. Each hexokinase gene in a library of hexokinase genes can be present in a chimeric construct such that the gene can be flanked by one or more regulatory sequences and/or sequence homologous to sequence present in the genome of a host cell. The sequence homologous to sequence present in the host cell can facilitate integration of the hexokinase gene into a site or locus of the host cell genome that comprises complementary sequence. Integration can be via a recombination event. The regulatory sequence can be any regulatory sequence known in the art or provided herein such as, for example, a promoter, start, stop, signal, secretion and/or termination sequence used by the genetic machinery of the host cell.

Provided herein is a library comprising glucose permease genes and hexokinase genes for use in the methods provided herein. In one embodiment, the glucose permease genes and the hexokinase genes are present in a single chimeric insert. Each glucose permease gene or hexokinase gene (e.g., glucokinase gene) in a chimeric construct in the library can be a native form or a mutated form of either gene. A mutated form of either gene can comprise one or more mutations selected from an insertion, deletion, single nucleotide polymorphism (SNP), or translocation. The glucose permease gene can be a bacterial glucose permease gene. The glucose permease gene can be any bacterial glucose permease gene known in the art. In one embodiment, a glucose permease gene in a chimeric construct comprises a glucose permease gene from any strain/species/sub-species of *Mycobacterium* (e.g., *Mycobacterium smegmatis*), *Streptomyces* (e.g., *Streptomyces coelicolor*), *Zymomonas* (e.g., *Zymomonas mobilis*), *Synechocystis* (e.g., *Synechocystis* sp. PCC6803), or *Bifidobacterium* (e.g., *Bifidobacterium longum*) *Escherichia* (e.g., *Escherichia coli*), *Bacillus* (e.g., *Bacillus subtilis*) or *Corynebacterium* (e.g., *Corynebacterium glutamicum*). In one embodiment, the glucose permease gene in a chimeric construct is a gene that encodes a polypeptide sequence selected from SEQ ID NO: 9, SEQ ID NO: 10, SEQ ID NO: 11, SEQ ID NO: 12, SEQ ID NO: 13 or SEQ ID NO: 14. In one embodiment, the glucose permease gene in a chimeric construct is selected from SEQ ID NO: 19, SEQ ID NO: 20, SEQ ID NO: 21, SEQ ID NO: 22, SEQ ID NO: 23, SEQ ID NO: 24 or a combination thereof. The hexokinase gene in each chimeric construct can be a glucokinase gene. Each glucokinase gene in each chimeric construct can be a bacterial glucokinase gene. The glucokinase gene can be any bacterial glucokinase gene known in the art. In one embodiment, a glucokinase gene in a chimeric construct comprises a glucokinase gene from any strain/species/sub-species of *Corynebactium* (e.g., *C. glutamicum*), *Zymomonas* (e.g., *Zymomonas mobilis*), *Staphylococcus* (e.g., *S. aureus* glkA), *Enterococcus* (e.g., *E. faecalis*), *Escherichia* (e.g., *E. coli*), *Clostridium* (e.g., *C. difficile*), *Streptococcus* (e.g., *S. pneumonia*), *Bacillus* (e.g., *B. anthracis*) or *Renibacterium* (e.g., *R. salmoninarium*). In one embodiment, the glucokinase gene in the chimeric construct comprises a glucokinase gene that encodes a polypeptide sequence selected from SEQ ID NO: 15 and/or SEQ ID NO: 16. In one embodiment, the glucokinase gene in the chimeric construct is selected from SEQ ID NO: 25 and/or SEQ ID NO: 26. In the chimeric construct as provided herein the glucose permease gene can be any glucose permease gene provided herein, while the glucokinase gene can be any glucokinase gene provided herein. In one embodiment, a library comprising chimeric glucose permease gene and glucokinase gene constructs comprises a plurality of constructs, whereby the plurality comprises each possible combination of glucose permease genes and glucokinase genes provided herein.

Each glucose permease gene and/or hexokinase gene (e.g., glucokinase gene) in a chimeric construct as provided herein can be functionally linked or under the control of its native promoter or a mutated form of its native promoter. Each glucose permease gene and/or hexokinase gene (e.g., glucokinase gene) in a chimeric construct as provided herein can be functionally linked to or controlled by any promoter provided herein. Each glucose permease genes in a chimeric construct as provided herein can be controlled by a promoter polynucleotide sequence that comprises or contains a sequence selected from SEQ ID NO: 1, SEQ ID NO: 2, SEQ ID NO: 3, SEQ ID NO: 4, SEQ ID NO: 5, SEQ ID NO: 7, and SEQ ID NO: 8. Each hexokinase gene (e.g., glucokinase gene) in a chimeric construct as provided herein can be controlled by a promoter polynucleotide sequence that comprises or contains a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. The glucose permease gene and the hexokinase gene (e.g., glucokinase gene) in a chimeric construct as provided herein can each be functionally linked to a promoter that comprises or contains the same sequence. The glucose permease gene and the hexokinase gene (e.g., glucokinase gene) in a chimeric construct as provided herein can each be functionally linked to a promoter that comprises or contains different sequence.

Generating Mutated Forms of Glucose Permease and/or Hexokinase Genes

As provided herein, a glucose permease gene and/or a hexokinase gene (e.g., glucokinase gene) for use in the methods provided herein can be a mutated form of the gene from which it is derived. The mutated gene can be mutated in any way known in the art or provided herein.

In some embodiments, the present disclosure teaches mutating cell populations by introducing, deleting, or replacing selected portions of genomic DNA. Thus, in some embodiments, the present disclosure teaches methods for targeting mutations to a specific locus (e.g., glucose permease or glucokinase). In other embodiments, the present disclosure teaches the use of gene editing technologies such as ZFNs, TALENS, or CRISPR, to selectively edit target DNA regions. Following mutation of the cell populations, the targeted mutations can be isolated from the cells and subsequently used for generating a library of glucose permease and/or hexokinase genes as described herein.

In some embodiments, the present disclosure teaches mutating selected DNA regions (e.g., glucose permease genes or glucokinase genes) outside of the host organism. For example, in some embodiments, the present disclosure teaches mutating native glucose permease genes or hexokinase genes (e.g., glucokinase gene).

In some embodiments, the selected regions of DNA are produced in vitro via gene shuffling of natural variants, or shuffling with synthetic oligos, plasmid-plasmid recombination, virus plasmid recombination, or virus-virus recombination. In other embodiments, the genomic regions are produced via error-prone PCR or site-directed mutagenesis.

In some embodiments, generating mutations in selected genetic regions containing a glucose permease or hexokinase gene is accomplished by "reassembly PCR." Briefly, oligonucleotide primers (oligos) are synthesized for PCR amplification of segments of a nucleic acid sequence of interest (e.g., glucose permease gene or glucokinase gene), such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols. In brief, in an assembly protocol, the PCR products are first purified away from the primers, by, for example, gel electrophoresis or size exclusion chromatography. Purified products are mixed together and subjected to about 1-10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes.

In some embodiments of the disclosure, mutated permease or hexokinase DNA regions, such as those discussed above, are enriched for mutant sequences so that the multiple mutant spectrum, i.e. possible combinations of mutations, is more efficiently sampled. In some embodiments, mutated sequences are identified via a mutS protein affinity matrix (Wagner et al., Nucleic Acids Res. 23(19):3944-3948 (1995); Su et al., Proc. Natl. Acad. Sci. (U.S.A.), 83:5057-5061 (1986)) with a preferred step of amplifying the affinity-purified material in vitro prior to an assembly reaction. This amplified material is then put into an assembly or reassembly PCR reaction.

Generation of Libraries Comprising Glucose Permease and/or Hexokinase Genes

In some embodiments, the present disclosure teaches inserting and/or replacing and/or deleting a DNA segment comprising a glucose permease and/or glucokinase gene of the host organism (e.g.,). In some aspects, the methods taught herein involve building an oligonucleotide of interest (i.e. a glucose permease or glucose permease-hexokinase segment), which can be incorporated into the genome of a host organism. In some embodiments, the glucose permease or glucose permease-hexokinase DNA segments of the present disclosure can be obtained via any method known in the art, including, copying or cutting from a known template, mutation, or DNA synthesis. In some embodiments, the present disclosure is compatible with commercially available gene synthesis products for producing DNA sequences (e.g., GeneArt™ GeneMaker™, GenScript™, Anagen™, Blue Heron™, Entelechon™, GeNOsys, Inc., or Qiagen™).

In some embodiments, the glucose permease or glucose permease-hexokinase DNA segment is designed to incorporate the glucose permease or glucose permease-hexokinase DNA segment into a selected DNA region of the host organism (e.g., adding a beneficial non-PTS glucose transport system). The selected DNA region can be a neutral integration site. In other embodiments, the glucose permease or glucose permease-hexokinase DNA segment is designed to remove the native permease and/or hexokinase gene from the DNA of the host organisms (e.g., removing a native PTS glucose transport system).

In some embodiments, the glucose permease gene, hexokinase gene or glucose permease-hexokinase genes used in the inventive methods can be synthesized in stages as oligonucleotides using any of the methods of enzymatic or chemical synthesis known in the art. The oligonucleotides may be synthesized on solid supports such as controlled pore glass (CPG), polystyrene beads, or membranes composed of thermoplastic polymers that may contain CPG. Oligonucleotides can also be synthesized on arrays, on a parallel microscale using microfluidics (Tian et al., Mol. BioSyst., 5, 714-722 (2009)), or known technologies that offer combinations of both (see Jacobsen et al., U.S. Pat. App. No. 2011/0172127).

Synthesis on arrays or through microfluidics offers an advantage over conventional solid support synthesis by reducing costs through lower reagent use. The scale required for gene synthesis is low, so the scale of oligonucleotide product synthesized from arrays or through microfluidics is acceptable. However, the synthesized oligonucleotides are of lesser quality than when using solid support synthesis (See Tian infra.; see also Staehler et al., U.S. Pat. App. No. 2010/0216648).

A great number of advances have been achieved in the traditional four-step phosphoramidite chemistry since it was first described in the 1980's (see for example, Sierzchala, et al. J. Am. Chem. Soc., 125, 13427-13441 (2003) using peroxy anion deprotection; Hayakawa et al., U.S. Pat. No. 6,040,439 for alternative protecting groups; Azhayev et al, *Tetrahedron* 57, 4977-4986 (2001) for universal supports; Kozlov et al., *Nucleosides, Nucleotides, and Nucleic Acids,* 24 (5-7), 1037-1041 (2005) for improved synthesis of longer oligonucleotides through the use of large-pore CPG; and Damha et al., *NAR,* 18, 3813-3821 (1990) for improved derivatization).

Regardless of the type of synthesis, the resulting oligonucleotides may then form the smaller building blocks for longer polynucleotides (i.e., glucose permease gene, hexokinase gene or glucose permease-hexokinase genes). In some embodiments, smaller oligonucleotides can be joined together using protocols known in the art, such as polymerase chain assembly (PCA), ligase chain reaction (LCR), and thermodynamically balanced inside-out synthesis (TBIO) (see Czar et al. Trends in Biotechnology, 27, 63-71 (2009)). In PCA, oligonucleotides spanning the entire length of the desired longer product are annealed and extended in multiple cycles (typically about 55 cycles) to eventually achieve full-length product. LCR uses ligase enzyme to join two oligonucleotides that are both annealed to a third oligonucleotide. TBIO synthesis starts at the center of the desired product and is progressively extended in both directions by using overlapping oligonucleotides that are homologous to the forward strand at the 5' end of the gene and against the reverse strand at the 3' end of the gene.

Another method of synthesizing a larger double stranded DNA fragment is to combine smaller oligonucleotides through top-strand PCR (TSP). In this method, a plurality of oligonucleotides spans the entire length of a desired product and contain overlapping regions to the adjacent oligonucleotide(s). Amplification can be performed with universal forward and reverse primers, and through multiple cycles of amplification a full-length double stranded DNA product is formed. This product can then undergo optional error correction and further amplification that results in the desired double stranded DNA fragment end product.

In one method of TSP, the set of smaller oligonucleotides that will be combined to form the full-length desired product are between 40-200 bases long and overlap each other by at least about 15-20 bases. For practical purposes, the overlap region should be at a minimum long enough to ensure specific annealing of oligonucleotides and have a high enough melting temperature (Tm) to anneal at the reaction temperature employed. The overlap can extend to the point where a given oligonucleotide is completely overlapped by adjacent oligonucleotides. The amount of overlap does not seem to have any effect on the quality of the final product. The first and last oligonucleotide building block in the assembly should contain binding sites for forward and reverse amplification primers. In one embodiment, the terminal end sequence of the first and last oligonucleotide contain the same sequence of complementarity to allow for the use of universal primers.

Assembling/Cloning Plasmids

In some embodiments, the present disclosure teaches methods for constructing vectors capable of inserting desired glucose permease genes and/or glucokinase genes DNA sections into the genome of host organisms. In some embodiments, the present disclosure teaches methods of cloning vectors comprising the insert DNA (e.g., glucose permease gene and/or glucokinase gene), homology arms, and at least one selection marker. (see FIG. 3).

In some embodiments, the present disclosure is compatible with any vector suited for transformation into the host organism. In some embodiments, the present disclosure teaches use of shuttle vectors compatible with a host cell. In one embodiment, a shuttle vector for use in the methods provided herein is a shuttle vector compatible with an *E. coli* and/or *Corynebacterium* host cell. Shuttle vectors for use in the methods provided herein can comprise markers for selection and/or counter-selection as described herein. The markers can be any markers known in the art and/or provided herein. The shuffle vectors can further comprise any regulatory sequence(s) and/or sequences useful in the assembly of said shuttle vectors as known in the art. The shuttle vectors can further comprise any origins of replication that may be needed for propagation in a host cell as provided herein such as, for example, *E. coli* or *C. glutamicum*. The regulatory sequence can be any regulatory sequence known in the art or provided herein such as, for example, a promoter, start, stop, signal, secretion and/or termination sequence used by the genetic machinery of the host cell. The termination sequence can be SEQ ID NO: 17 or 18. In certain instances, the target DNA can be inserted into vectors, constructs or plasmids obtainable from any repository or catalogue product, such as a commercial vector (see e.g., DNA2.0 custom or GATEWAY® vectors).

In some embodiments, the assembly/cloning methods of the present disclosure may employ at least one of the following assembly strategies: 1) type II conventional cloning, ii) type II S-mediated or "Golden Gate" cloning (see, e.g., Engler, C., R. Kandzia, and S. Marillonnet. 2008 "A one pot, one step, precision cloning method with high throughput capability". PLos One 3:e3647; Kotera, I., and T. Nagai. 2008 "A high-throughput and single-tube recombination of crude PCR products using a DNA polymerase inhibitor and type IIS restriction enzyme." J Biotechnol 137:1-7; Weber, E., R. Gruetzner, S. Werner, C. Engler, and S. Marillonnet. 2011 Assembly of Designer TAL Effectors by Golden Gate Cloning. PloS One 6:e19722), iii) GATEWAY® recombination, iv) TOPO® cloning, exonuclease-mediated assembly (Aslanidis and de Jong 1990. "Ligation-independent cloning of PCR products (LIC-PCR)." Nucleic Acids Research, Vol. 18, No. 20 6069), v) homologous recombination, vi) non-homologous end joining, or a combination thereof. Modular type IIS based assembly strategies are disclosed in PCT Publication WO 2011/154147, the disclosure of which is included herein by reference.

In some embodiments, the present disclosure teaches cloning vectors with at least one selection marker. Various selection marker genes are known in the art often encoding antibiotic resistance function for selection in prokaryotic (e.g., against ampicillin, kanamycin, tetracycline, chloramphenycol, zeocin, spectinomycin/streptomycin) or eukaryotic cells (e.g. geneticin, neomycin, hygromycin, puromycin, blasticidin, zeocin) under selective pressure. Other marker systems allow for screening and identification of wanted or unwanted cells such as the well-known blue/white screening system used in bacteria to select positive clones in the presence of X-gal or fluorescent reporters such as green or red fluorescent proteins expressed in successfully transduced host cells. Another class of selection markers most of which are only functional in prokaryotic systems relates to counter selectable marker genes often also referred to as "death genes" which express toxic gene products that kill producer cells. Examples of such genes include sacB, rpsL (strA), tetAR, pheS, thyA, gata-1, or ccdB, the function of which is described in (Reyrat et al. 1998 "Counterselectable Markers: Untapped Tools for Bacterial Genetics and Pathogenesis." Infect Immun. 66(9): 4011-4017).

In one embodiment, the vector into which the target DNA segment is cloned into comprises a promoter polynucleotide from a promoter ladder or library as provided herein. In one embodiment, provided herein is promoter ladder comprising or containing a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

In one embodiment, the vector comprises a first promoter polynucleotide and a second promoter polynucleotide. The first and/or second promoter polynucleotide can comprise or contain a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. The promoter polynucleotide can be used in each case for over-expressing or under-expressing a glucose permease and/or hexokinase in a host microorganism.

In some embodiments, each generated strain comprising a heterologous glucose permease gene or glucose permease gene-glucokinase gene is cultured and analyzed under one or more criteria of the present disclosure (e.g., productivity of a biomolecule or product of interest). Data from each of the analyzed host strains is associated/correlated with a particular glucose permease gene or glucose permease gene/glucokinase gene combination, and is recorded for future use. Thus, the present disclosure enables the creation of large and highly annotated genetic diversity libraries/depositories that identify the effect of a glucose permease gene or combination of glucose permease gene/glucokinase gene on any number of microbial genetic or phenotypic traits of interest.

In some embodiments, the present disclosure teaches the use of vectors for cloning the glucose permease gene and/or hexokinase gene with start and/or stop codon variants such that the cloned gene utilizes the start and/or stop codon variant. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218).

In one embodiment, the methods of the provided disclosure comprise codon optimizing one or more genes expressed by the host organism. Methods for optimizing codons to improve expression in various hosts are known in the art and are described in the literature (see U.S. Pat. App. Pub. No. 2007/0292918, incorporated herein by reference in its entirety). Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence.

In some embodiments, a glucose permease gene or polynucleotide provided herein comprises a molecule codon optimized for translation in a host cell provided herein, such as, for example, *E. coli* and/or *C. glutamicum*. The gene or polynucleotide can be an isolated, synthetic or recombinant nucleic acid. The codon optimized glucose permease gene or polynucleotide can be selected from SEQ ID NO: 19, SEQ ID NO: 20, SEQ ID NO: 21, SEQ ID NO: 22, SEQ ID NO: 23, SEQ ID NO: 24. In some cases, provided herein is a permease gene or polynucleotide that is codon optimized to encode a polypeptide sequence selected from SEQ ID NO: 9, SEQ ID NO: 10, SEQ ID NO: 11, SEQ ID NO: 12, SEQ ID NO: 13 or SEQ ID NO: 14. The codon optimized glucose permease gene or polynucleotide provided herein can be generated using a method known in the art for generating codon optimized polynucleotides such as, for example, GenScript's OptimumGene™ gene design system or DNA2.0 GeneGPS® Expression Optimization technology.

In some embodiments, a hexokinase (e.g., glucokinase) gene or polynucleotide provided herein comprises a molecule codon optimized for translation in a host cell provided herein, such as, for example, *E. coli* and/or *C. glutamicum*. The gene or polynucleotide can be an isolated, synthetic or recombinant nucleic acid. The codon optimized hexokinase gene (e.g., glucokinase gene) can be selected from SEQ ID NO: 25 or SEQ ID NO: 26. In some cases, provided herein is a hexokinase (e.g., glucokinase) gene or polynucleotide that is codon optimized to encode a polypeptide sequence selected from SEQ ID NO: 15 or SEQ ID NO: 16. The codon optimized hexokinase (e.g., glucokinase) gene or polynucleotide provided herein can be generated using a method known in the art for generating codon optimized polynucleotides such as, for example, GenScript's OptimumGene™ gene design system or DNA2.0 GeneGPS® Expression Optimization technology.

Protein expression is governed by a host of factors including those that affect transcription, mRNA processing, and stability and initiation of translation. Optimization can thus address any of a number of sequence features of any particular gene. As a specific example, a rare codon induced translational pause can result in reduced protein expression. A rare codon induced translational pause includes the presence of codons in the polynucleotide of interest that are rarely used in the host organism may have a negative effect on protein translation due to their scarcity in the available tRNA pool.

Alternate translational initiation also can result in reduced heterologous protein expression. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes eliminating putative internal RBS sequences from an optimized polynucleotide sequence.

Repeat-induced polymerase slippage can result in reduced heterologous protein expression. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Interfering secondary structures also can result in reduced heterologous protein expression. Secondary structures can sequester the RBS sequence or initiation codon and have been correlated to a reduction in protein expression. Stem-loop structures can also be involved in transcriptional pausing and attenuation. An optimized polynucleotide sequence can contain minimal secondary structures in the RBS and gene coding regions of the nucleotide sequence to allow for improved transcription and translation.

For example, the optimization process can begin by identifying the desired amino acid sequence to be expressed by the host. From the amino acid sequence a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures.

Transformation of Host Cells

In some embodiments, the vectors of the present disclosure may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., 1986 "Basic Methods in Molecular Biology"). Other methods of transformation include for example, lithium acetate transformation and electroporation See, e.g., Gietz et al., Nucleic Acids Res. 27:69-74 (1992); Ito et al., J. Bacterol. 153:163-168 (1983); and Becker and Guarente, Methods in Enzymology 194:182-187 (1991). In some embodiments, transformed host cells are referred to as recombinant host strains.

In some embodiments, the present disclosure teaches high throughput transformation of cells using 96-well plate robotics platform and liquid handling machines known in the art.

In some embodiments, the present disclosure teaches screening transformed cells with one or more selection markers. In one such embodiment, cells transformed with a vector comprising a kanamycin resistance marker (KanR) are plated on media containing effective amounts of the kanamycin antibiotic. Colony forming units visible on kanamycin-laced media are presumed to have incorporated the vector cassette into their genome. Insertion of the desired sequences can be confirmed via PCR, restriction enzyme analysis, and/or sequencing of the relevant insertion site.

Looping Out of Selected Sequences

In some embodiments, the present disclosure teaches methods of looping out selected regions of DNA from the host organisms. The looping out method can be as described in Nakashima et al. 2014 "Bacterial Cellular Engineering by Genome Editing and Gene Silencing." Int. J. Mol. Sci. 15(2), 2773-2793. In some embodiments, the present disclosure teaches looping out selection markers from positive transformants. Looping out deletion techniques are known in the art, and are described in (Tear et al. 2014 "Excision of Unstable Artificial Gene-Specific inverted Repeats Mediates Scar-Free Gene Deletions in *Escherichia coli*." Appl. Biochem. Biotech. 175:1858-1867). The looping out methods used in the methods provided herein can be performed using single-crossover homologous recombination or double-crossover homologous recombination. In one embodiment, looping out of selected regions as described herein can entail using single-crossover homologous recombination as described herein.

First, loop out vectors are inserted into selected target regions within the genome of the host organism (e.g., via homologous recombination, CRISPR, or other gene editing technique). In one embodiment, single-crossover homologous recombination is used between a circular plasmid or vector and the host cell genome in order to loop-in the circular plasmid or vector such as depicted in FIG. 3. The inserted vector can be designed with a sequence which is a direct repeat of an existing or introduced nearby host sequence, such that the direct repeats flank the region of DNA slated for looping and deletion. Once inserted, cells containing the loop out plasmid or vector can be counter selected for deletion of the selection region (e.g., see FIG. 4; lack of resistance to the selection gene).

Host Microorganisms

The genomic engineering methods provided herein are exemplified with industrial microbial cell cultures, but can be applicable to any organism where desired traits can be identified in a population of genetic mutants.

Thus, as used herein, the term "microorganism" should be taken broadly. It includes, but is not limited to, the two prokaryotic domains, Bacteria and Archaea, as well as certain eukaryotic fungi and protists. However, in certain aspects, "higher" eukaryotic organisms such as insects, plants, and animals can be utilized in the methods taught herein.

Suitable host cells include, but are not limited to: bacterial cells, algal cells, plant cells, fungal cells, insect cells, and mammalian cells. In one illustrative embodiment, suitable host cells include *E. coli* (e.g., SHuffle™ competent *E. coli* available from New England BioLabs in Ipswich, Mass.).

Other suitable host organisms of the present disclosure include microorganisms of the genus *Corynebacterium*. In some embodiments, preferred *Corynebacterium* strains/species include: *C. efficiens*, with the deposited type strain being DSM44549, *C. glutamicum*, with the deposited type strain being ATCC13032, and *C. ammoniagenes*, with the deposited type strain being ATCC6871. In some embodiments, the preferred host of the present disclosure is *C. glutamicum*.

Suitable host strains of the genus *Corynebacterium*, in particular of the species *Corynebacterium glutamicum*, are in particular the known wild-type strains: *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium flavum* ATCC14067, *Brevibacterium lactofermentum* ATCC13869, and *Brevibacterium divaricatum* ATCC14020; and L-amino acid-producing mutants, or strains, prepared therefrom, such as, for example, the L-lysine-producing strains: *Corynebacterium glutamicum* FERM-P 1709, *Brevibacterium flavum* FERM-P 1708, *Brevibacterium lactofermentum* FERM-P 1712, *Corynebacterium glutamicum* FERM-P 6463, *Corynebacterium glutamicum* FERM-P 6464, *Corynebacterium glutamicum* DM58-1, *Corynebacterium glutamicum* DG52-5, *Corynebacterium glutamicum* DSM5714, and *Corynebacterium glutamicum* DSM12866.

The term "*Micrococcus glutamicus*" has also been in use for *C. glutamicum*. Some representatives of the species *C. efficiens* have also been referred to as *C. thermoaminogenes* in the prior art, such as the strain FERM BP-1539, for example.

In some embodiments, the host cell of the present disclosure is a eukaryotic cell. Suitable eukaryotic host cells include, but are not limited to: fungal cells, algal cells, insect cells, animal cells, and plant cells. Suitable fungal host cells include, but are not limited to: *Ascomycota, Basidiomycota, Deuteromycota, Zygomycota, Fungi imperfecti*. Certain preferred fungal host cells include yeast cells and filamentous fungal cells. Suitable filamentous fungi host cells include, for example, any filamentous forms of the subdivision *Eumycotina* and *Oomycota*. (see, e.g., Hawksworth et al., In Ainsworth and Bisby's Dictionary of The Fungi, 8$^{th}$ edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungi host cells are morphologically distinct from yeast.

In certain illustrative, but non-limiting embodiments, the filamentous fungal host cell may be a cell of a species of: *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella*, or teleomorphs, or anamorphs, and synonyms or taxonomic equivalents thereof.

Suitable yeast host cells include, but are not limited to: *Candida, Hansenula, Saccharomyces, Schizosaccharomyces, Pichia, Kluyveromyces*, and *Yarrowia*. In some embodiments, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia hpolytica*.

In certain embodiments, the host cell is an algal such as, *Chlamydomonas* (e.g., *C. Reinhardtii*) and *Phormidium* (*P.* sp. ATCC29409).

In other embodiments, the host cell is a prokaryotic cell. Suitable prokaryotic cells include gram positive, gram negative, and gram-variable bacterial cells. The host cell may be a species of, but not limited to: *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia*, and *Zymomonas*. In some embodiments, the host cell is *Corynebacterium glutamicum*.

In some embodiments, the bacterial host strain is an industrial strain. Numerous bacterial industrial strains are known and suitable in the methods and compositions described herein.

In some embodiments, the bacterial host cell is of the *Agrobacterium* species (e.g., *A. radiobacter, A. rhizogenes, A. rubi*), the *Arthrobacter*species (e.g., *A. aurescens, A. citreus, A. globformis, A. hydrocarboglutamicus, A. mysorens, A. nicotianae, A. paraffineus, A. protophonniae, A. roseoparaffinus, A. sulfureus, A. ureafaciens*), the *Bacillus* species (e.g., *B. thuringiensis, B. anthracis, B. megaterium, B. subtilis, B. lentus, B. circulars, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. In some embodiments, the host cell will be an industrial *Clostridium* species (e.g., *C. acetobutylicum, C. tetani* E88, *C. lituseburense, C. saccharobutylicum, C. perfringens, C. beijerinckii*). In some embodiments, the host cell will be an industrial *Corynebacterium* species (e.g., *C. glutamicum, C. acetoacidophilum*). In some embodiments, the host cell will be an industrial *Escherichia* species (e.g., *E. coli*). In some embodiments, the host cell will be an industrial *Erwinia* species (e.g., *E. uredovora, E. carotovora, E. ananas, E. herbicola, E. punctata, E. terreus*). In some embodiments, the host cell will be an industrial *Pantoea* species (e.g., *P. citrea, P. agglomerans*). In some embodiments, the host cell will be an industrial *Pseudomonas* species, (e.g., *P. putida, P. aeruginosa, P. mevalonii*). In some embodiments, the host cell will be an industrial *Streptococcus* species (e.g., *S. equisimiles, S. pyogenes, S. uberis*). In some embodiments, the host cell will be an industrial *Streptomyces* species (e.g., *S. ambofaciens, S. achromogenes, S. avermitilis, S. coelicolor, S. aureofaciens, S. aureus, S. fungicidicus, S. griseus, S. lividans*). In some embodiments, the host cell will be an industrial *Zymomonas* species (e.g., *Z. mobilis, Z. hpolytica*), and the like.

In various embodiments, strains that may be used in the practice of the disclosure including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In some embodiments, the methods of the present disclosure are also applicable to multi-cellular organisms. For example, the platform could be used for improving the performance of crops. The organisms can comprise a plurality of plants such as Gramineae, Fetucoideae, Poacoideae, *Agrostis, Phleum, Dactylis, Sorgum, Setaria, Zea, Oryza, Triticum, Secale, Avena, Hordeum, Saccharum, Poa, Festuca, Stenotaphrum, Cynodon, Coix*, Olyreae, Phareae, Compositae or Leguminosae. For example, the plants can be corn, rice, soybean, cotton, wheat, rye, oats, barley, pea, beans, lentil, peanut, yam bean, cowpeas, velvet beans, clover, alfalfa, lupine, vetch, lotus, sweet clover, wisteria, sweet pea, sorghum, millet, sunflower, canola or the like. Similarly, the organisms can include a plurality of animals such as non-human mammals, fish, insects, or the like.

Cell Fermentation and Culture

Microorganisms of the present disclosure including those genetically engineered as described herein can be cultured in conventional nutrient media modified as appropriate for any desired biosynthetic reactions or selections. In some embodiments, the present disclosure teaches culture in inducing media for activating promoters. In some embodiments, the present disclosure teaches media with selection agents, including selection agents of transformants (e.g., antibiotics), or selection of organisms suited to grow under inhibiting conditions (e.g., high ethanol conditions). In some embodiments, the present disclosure teaches growing cell cultures in media optimized for cell growth. In other embodiments, the present disclosure teaches growing cell cultures in media optimized for product yield such as, for example, products or biomolecules of interest derived from metabolic processing of glucose. In some embodiments, the present disclosure teaches growing cultures in media capable of inducing cell growth and also contains the necessary precursors for final product production (e.g., high levels of sugars for ethanol production). The biomolecules or products of interest produced by the methods provided herein can be any commercial product produced from glucose. In some cases, the biomolecule or product of interest is a small molecule, an amino acid, an organic acid, or an alcohol. The amino acid can be tyrosine, phenylalanine, tryptophan, aspartic acid, asparagine, threonine, isoleucine, methionine, or lysine. The organic acid can be succinate, lactate or pyruvate. The alcohol can be ethanol or isobutanol.

Culture conditions, such as temperature, pH and the like, are those suitable for use with the host cell selected for expression, and will be apparent to those skilled in the art. As noted, many references are available for the culture and production of many cells, including cells of bacterial, plant, animal (including mammalian) and archebacterial origin. See e.g., Sambrook, Ausubel (all supra), as well as Berger, *Guide to Molecular Cloning Techniques, Methods in Enzymology* volume 152 Academic Press, Inc., San Diego, Calif.; and Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelle et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* from Sigma-Aldrich, Inc (St Louis, Mo.) ("Sigma-LSRCCC") and, for example, *The Plant Culture Catalogue* and supplement also from Sigma-Aldrich, Inc (St Louis, Mo.) ("Sigma-PCCS"), all of which are incorporated herein by reference.

The culture medium or fermentation medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981). The terms culture medium and fermentation medium are interchangeable.

In some embodiments, the present disclosure teaches that the microorganisms produced may be cultured continuously—as described, for example, in WO 05/021772—or discontinuously in a batch process (batch cultivation) or in a fed-batch or repeated fed-batch process for the purpose of producing the desired organic-chemical compound. A summary of a general nature about known cultivation methods is available in the textbook by Chmiel (Bioprozeβtechnik. 1: Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

In some embodiments, the cells of the present disclosure are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present disclosure. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is a system where a defined fermentation medium is added continuously to a bioreactor and an equal amount of conditioned medium is removed simultaneously for processing and harvesting of desired proteins. In some embodiments, continuous fermentation generally maintains the cultures at a constant high density where cells are primarily in log phase growth. In some embodiments, continuous fermentation generally maintains the cultures at a stationary or late log/stationary, phase growth. Continuous fermentation systems strive to maintain steady state growth conditions.

Methods for modulating nutrients and growth factors for continuous fermentation processes as well as techniques for maximizing the rate of product formation are well known in the art of industrial microbiology.

For example, a non-limiting list of carbon sources for the cultures of the present disclosure include, sugars and carbohydrates such as, for example, glucose, sucrose, lactose, fructose, maltose, molasses, sucrose-containing solutions from sugar beet or sugar cane processing, starch, starch hydrolysate, and cellulose; oils and fats such as, for example, soybean oil, sunflower oil, groundnut oil and coconut fat; fatty acids such as, for example, palmitic acid, stearic acid, and linoleic acid; alcohols such as, for example, glycerol, methanol, and ethanol; and organic acids such as, for example, acetic acid or lactic acid.

A non-limiting list of the nitrogen sources for the cultures of the present disclosure include, organic nitrogen-containing compounds such as peptones, yeast extract, meat extract, malt extract, corn steep liquor, soybean flour, and urea; or inorganic compounds such as ammonium sulfate, ammonium chloride, ammonium phosphate, ammonium carbonate, and ammonium nitrate. The nitrogen sources can be used individually or as a mixture.

A non-limiting list of the possible phosphorus sources for the cultures of the present disclosure include, phosphoric acid, potassium dihydrogen phosphate or dipotassium hydrogen phosphate or the corresponding sodium-containing salts. The culture medium may additionally comprise salts, for example in the form of chlorides or sulfates of metals such as, for example, sodium, potassium, magnesium, calcium and iron, such as, for example, magnesium sulfate or iron sulfate, which are necessary for growth. Finally, essential growth factors such as amino acids, for example homoserine and vitamins, for example thiamine, biotin or pantothenic acid, may be employed in addition to the abovementioned substances.

In some embodiments, the pH of the culture can be controlled by any acid or base, or buffer salt, including, but not limited to sodium hydroxide, potassium hydroxide, ammonia, or aqueous ammonia; or acidic compounds such as phosphoric acid or sulfuric acid in a suitable manner. In some embodiments, the pH is generally adjusted to a value of from 6.0 to 8.5, preferably 6.5 to 8.

In some embodiments, the cultures of the present disclosure may include an anti-foaming agent such as, for example, fatty acid polyglycol esters. In some embodiments the cultures of the present disclosure are modified to stabilize the plasmids of the cultures by adding suitable selective substances such as, for example, antibiotics.

In some embodiments, the culture is carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch or fed-batch processes, the cultivation is preferably continued until an amount of the desired organic-chemical compound sufficient for being recovered has formed. In some embodiments, the culture is carried out under anaerobic conditions.

Product Recovery and Quantification

Methods for screening for the production of products of interest are known to those of skill in the art and are discussed throughout the present specification. Such methods may be employed when screening the strains of the disclosure. The biomolecules or products of interest produced by the methods provided herein can be any commercial product produced from glucose. In some cases, the biomolecule or product of interest is an amino acid, an organic acid, or an alcohol. The amino acid can be tyrosine, phenylalanine, tryptophan, aspartic acid, asparagine, threonine, isoleucine, methionine, or lysine. The organic acid can be succinate, lactate or pyruvate. The alcohol can be ethanol or isobutanol.

In some embodiments, the present disclosure teaches methods of improving strains designed to produce non-secreted intracellular products. For example, the present disclosure teaches methods of improving the robustness, yield, efficiency, or overall desirability of cell cultures producing intracellular enzymes, oils, pharmaceuticals, or other valuable small molecules or peptides. The recovery or isolation of non-secreted intracellular products can be achieved by lysis and recovery techniques that are well known in the art, including those described herein.

For example, in some embodiments, cells of the present disclosure can be harvested by centrifugation, filtration, settling, or other method. Harvested cells are then disrupted by any convenient method, including freeze-thaw cycling, sonication, mechanical disruption, or use of cell lysing agents, or other methods, which are well known to those skilled in the art.

The resulting product of interest, e.g. a polypeptide, may be recovered/isolated and optionally purified by any of a number of methods known in the art. For example, a product polypeptide may be isolated from the nutrient medium by conventional procedures including, but not limited to: centrifugation, filtration, extraction, spray-drying, evaporation, chromatography (e.g., ion exchange, affinity, hydrophobic interaction, chromatofocusing, and size exclusion), or precipitation. Finally, high performance liquid chromatography (HPLC) can be employed in the final purification steps. (See for example Purification of intracellular protein as described in Parry et al., 2001, *Biochem. J.* 353:117, and Hong et al., 2007, *Appl. Microbiol. Biotechnol.* 73:1331, both incorporated herein by reference).

In addition to the references noted supra, a variety of purification methods are well known in the art, including, for example, those set forth in: Sandana (1997) *Bioseparation of Proteins*, Academic Press, Inc.; Bollag et al. (1996) *Protein Methods*, $2^{nd}$ Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* $3^{rd}$ Edition, Springer Verlag, NY; Janson and Ryden (1998) *Protein Purification: Principles, High Resolution Methods and Applications*, Second Edition, Wiley-VCH, NY; and Walker (1998) Protein Protocols on CD-ROM, Humana Press, NJ, all of which are incorporated herein by reference.

In some embodiments, the present disclosure teaches the methods of improving strains designed to produce secreted products. For example, the present disclosure teaches methods of improving the robustness, yield, efficiency, or overall desirability of cell cultures producing valuable small molecules or peptides.

In some embodiments, immunological methods may be used to detect and/or purify secreted or non-secreted products produced by the cells of the present disclosure. In one example approach, antibody raised against a product molecule (e.g., against an insulin polypeptide or an immunogenic fragment thereof) using conventional methods is immobilized on beads, mixed with cell culture media under conditions in which the endoglucanase is bound, and precipitated. In some embodiments, the present disclosure teaches the use of enzyme-linked immunosorbent assays (ELISA).

In other related embodiments, immunochromatography is used, as disclosed in U.S. Pat. Nos. 5,591,645, 4,855,240, 4,435,504, 4,980,298, and Se-Hwan Paek, et al., "Development of rapid One-Step Immunochromatographic assay, Methods", 22, 53-60, 2000), each of which are incorporated by reference herein. A general immunochromatography detects a specimen by using two antibodies. A first antibody exists in a test solution or at a portion at an end of a test piece in an approximately rectangular shape made from a porous membrane, where the test solution is dropped. This antibody is labeled with latex particles or gold colloidal particles (this antibody will be called as a labeled antibody hereinafter). When the dropped test solution includes a specimen to be detected, the labeled antibody recognizes the specimen so as to be bonded with the specimen. A complex of the specimen and labeled antibody flows by capillarity toward an absorber, which is made from a filter paper and attached to an end opposite to the end having included the labeled antibody. During the flow, the complex of the specimen and labeled antibody is recognized and caught by a second antibody (it will be called as a tapping antibody hereinafter) existing at the middle of the porous membrane and, as a result of this, the complex appears at a detection part on the porous membrane as a visible signal and is detected.

In some embodiments, the screening methods of the present disclosure are based on photometric detection techniques (absorption, fluorescence). For example, in some embodiments, detection may be based on the presence of a fluorophore detector such as GFP bound to an antibody. In other embodiments, the photometric detection may be based on the accumulation on the desired product from the cell culture. In some embodiments, the product may be detectable via UV of the culture or extracts from said culture.

In some embodiments, the product recovery methods allow for the quantitative determination of the effect on performance of each candidate glucose permease gene and/or glucokinase gene. In some embodiments, the product recovery methods allow for the quantitative determination of the effect on performance of each candidate glucose permease gene/glucokinase gene combination, allowing for comparison of each and selection for the optimal combination.

Selection Criteria and Goals

The selection of a particular strain of host cell expressing a heterologous glucose permease or glucose permease and glucokinase can be based on specific goals. For example, in some embodiments, the program goal may be to maximize single batch yields of reactions with no immediate time limits. In other embodiments, the program goal may be to rebalance biosynthetic yields to produce a specific product, or to produce a particular ratio of products. In some embodiments, the program goal may be to improve performance characteristics such as yield, titer, productivity, by-product elimination, tolerance to process excursions, optimal growth temperature and growth rate. In some embodiments, the program goal is improved host performance as measured by volumetric productivity, specific productivity, yield or titre, of a product of interest produced by a microbe.

In other embodiments, the program goal may be to optimize synthesis efficiency of a commercial strain in terms of final product yield per quantity of inputs (e.g., total amount of ethanol produced per pound of sucrose). In other embodiments, the program goal may be to optimize synthesis speed, as measured for example in terms of batch completion rates, or yield rates in continuous culturing systems. In one embodiment, the program goal is to optimize final product yield and/or production rate of a biomolecule or product of interest. The biomolecules or products of interest produced by the methods provided herein can be any commercial product produced from glucose. In some cases, the biomolecule or product of interest is a small molecule, an amino acid, an organic acid, or an alcohol. The amino acid can be tyrosine, phenylalanine, tryptophan, aspartic acid, asparagine, threonine, isoleucine, methionine, or lysine. The organic acid can be succinate, lactate or pyruvate. The alcohol can be ethanol or isobutanol.

Persons having ordinary skill in the art will recognize how to tailor strain selection criteria to meet the particular project goal. For example, selections of a strain's single batch max yield at reaction saturation may be appropriate for identifying strains with high single batch yields. Selection based on consistency in yield across a range of temperatures and conditions may be appropriate for identifying strains with increased robustness and reliability.

In some embodiments, the selection criteria for the initial phase and the tank-based validation will be identical. In other embodiments, tank-based selection may operate under additional and/or different selection criteria.

EXAMPLES

The present invention is further illustrated by reference to the following Examples. However, it should be noted that these Examples, like the embodiments described above, is illustrative and is not to be construed as restricting the scope of the invention in any way.

Example 1: Transformation of *Corynebacterium* with Glucose Permease and Glucokinase Library Generation of Glucose Permease Libraries A number of glucose permeases from various bacteria were selected for generation of a glucose permease library based on their affinity and transport rates for glucose as reported in the literature. The glucose permease selected for inclusion in the library were the glucose permease genes from *Mycobacterium smegmatis* that encodes SEQ ID NO: 9; from *Bifidobacterium longum* (BL_1631 in FIG. 1) that encodes SEQ ID NO: 11; from *Zymomonas mobilis* (glf in FIG. 1) that encodes SEQ ID NO: 13; from *Synechocystis* sp. PCC6803 (glcP in FIG. 1) that encodes SEQ ID NO: 12; from *Streptomyces coelicolor* (SC05578 in FIG. 1) that encodes SEQ ID NO: 10; and the myo-inositol transporter gene from *Corynebacterium glutamicum* that encodes SEQ ID NO: 14. Additionally, two glucokinases were selected for use in the generation of the glucose permease library based on their compatibility with the host cell. The glucokinases chosen were the ppgK glucokinase gene from *Corynebacterium glutamicum* that encodes SEQ ID NO: 16 and the glk kinase gene from *Z. mobilis* that encodes SEQ ID NO: 15.

For generation of the glucose permease library, each glucose permease described above was paired with a glucokinase described above such that each gene was cloned into a single *C. glutamicum/Escherichia coli* compatible expression vector using type IIs restriction and ligation cloning techniques. More specifically, genes that encode the *M. smegmatis* glucose permease (SEQ ID NO: 9), the *B. longum* glucose permease (BL_1631; SEQ ID NO: 11), the *Synechocystis* sp. PCC6803 glucose permease (glcP; SEQ ID NO: 12), the *C. glutamicum* myo-inositol transporter (iolT1; SEQ ID NO: 14) and the *S. coelicolor* glucose permease (SC05578; SEQ ID NO: 10) were all individually paired with the gene that encodes *C. glutamicum* ppgK glucokinase (SEQ ID NO: 16), while the gene that encodes the *Z. mobilis* glucose permease (glf; SEQ ID NO: 10) was paired with the gene that encodes the *Z. mobilis* glk kinase (SEQ ID NO: 15) and separately paired with the gene that encodes *C. glutamicum* ppgK glucokinase (SEQ ID NO: 16). In addition, within each glucose permease-glucokinase construct, a P1 promoter (SEQ ID NO: 1) was cloned in front of the respective glucose permease gene, while a P2 promoter (SEQ ID NO: 2) was cloned in front of the respective glucokinase gene such that each respective permease or glucokinase gene was functionally linked to the preceding or upstream promoter. Finally, each permease gene in a construct ended with a T1 termination sequence (SEQ ID NO: 17), while each glucokinase gene in a construct ended with a T2 termination sequence (SEQ ID NO: 18).

Transformation of Assembled Clones into *E. coli*

Vectors containing the glucose permease-glucokinase genes were each individually transformed into *E. coli* in order to identify correctly assembled clones, and to amplify vector DNA for *Corynebacterium* transformation. Amplified DNA was validated via PCR. Positive clones were saved at −20° C. fridge for future use.

Transformation of Assembled Clones into *Corynebacterium*

Validated clones were then individually transformed into *Corynebacterium glutamicum* host cells via electroporation. In order to test the effect of strain background on construct performance, two different strain backgrounds (i.e., Parent 1/background 2 and parent 2/background 1 in FIGS. 1 and 2) of C. glutamicum were used with each construct being transformed into each background. Each vector was designed to integrate into a neutral integration site within the C. glutamicum genome that was empirically determined to permit expression of the heterologous glucose permease and glucokinase genes but not be detrimental to the host cell. To facilitate integration, the expression vector further comprised about 2 kb of sequence homologous (i.e., homology arms) to the desired integration site whereby each glucose permease-glucokinase gene cassette described above was inserted between. Integration into the genome occurred by single-crossover integration and then loop-out of the plasmid backbone facilitated by counter-selection on a second marker included in the plasmid backbone.

Transformed bacteria were then tested for assembly success (correct integration into the genome). Colonies from each *Corynebacterium* transformation plate were cultured and tested for correct integration via PCR. This process was repeated for each of the transformations conducted for each glucose permease-glucokinase construct. Genomic integration of each transformation was also analyzed with respect to the targeted genome location for each plasmid.

Evaluation of Individual Glucose Permease-Glukokinase Constructs in *Corynebacterium*

The phenotype of each transformant was then tested in an evaluation method designed to mimic or simulate a specific fermentation process for producing a desired fermentation end product in order to determine the effects the expression of each construct in each host cell background had on the desired phenotype (i.e., improved ability to produce a desired fermentation end product). Briefly, the evaluation method was an experiment where the transformants were cultured in a 96 well plate format under conditions that were meant to mimic fermentation conditions. The amount of product and biomass formed at various time points was measured and used to predict how each strain would perform under fermentation conditions. This prediction was a linear regression generated from testing strains with various fermentation performance in the evaluation method and determining the correlation of measurements to performance.

The rate of production and yield of the desired fermentation end product was determined for each permease-glucokinase transformant, some examples of which are shown in FIG. 1. As shown in FIG. 1, for the specific permease-glucokinase inserts shown, the productivity (top) in a fermentation process was predicted to increase in each host background for each permease-glucokinase insert shown vs. the respective control host cell, while the yield (bottom) was predicted to be similar (glcP; BL1631), increased (SCO5578), or decreased (glf) vs. the respective control host cell. Please note that the AU units in FIG. 1 are the output of a linear regression that takes as inputs various measurements made on cultures at small scale and predicts the performance of strains under fermentation conditions.

Assessment of Individual Glucose-Permease-Glucokinase Constructs Under Fermentation Conditions Following evaluation as described above, transformants with heterologous glucose permease-glucokinase genes with predicted increased performance (i.e., increased predicted productivity and/or predicted yield) were selected and subsequently grown in medium containing glucose under conditions designed to facilitate fermentation and the production of desired fermentation end products. Following growth of each transformant for a predetermined length of time under fermentation conditions designed to produce a desired end-product, the yield and volumetric productivity of the end-product for each transformant was then determined. Briefly, high-performance liquid chromatography (HPLC) was used to determine the amount of product (i.e., avg yield) produced for a certain amount of substrate fed. Productivity (i.e., avg productivity) was similarly determined with the addition of time and volume data.

Figure 2:
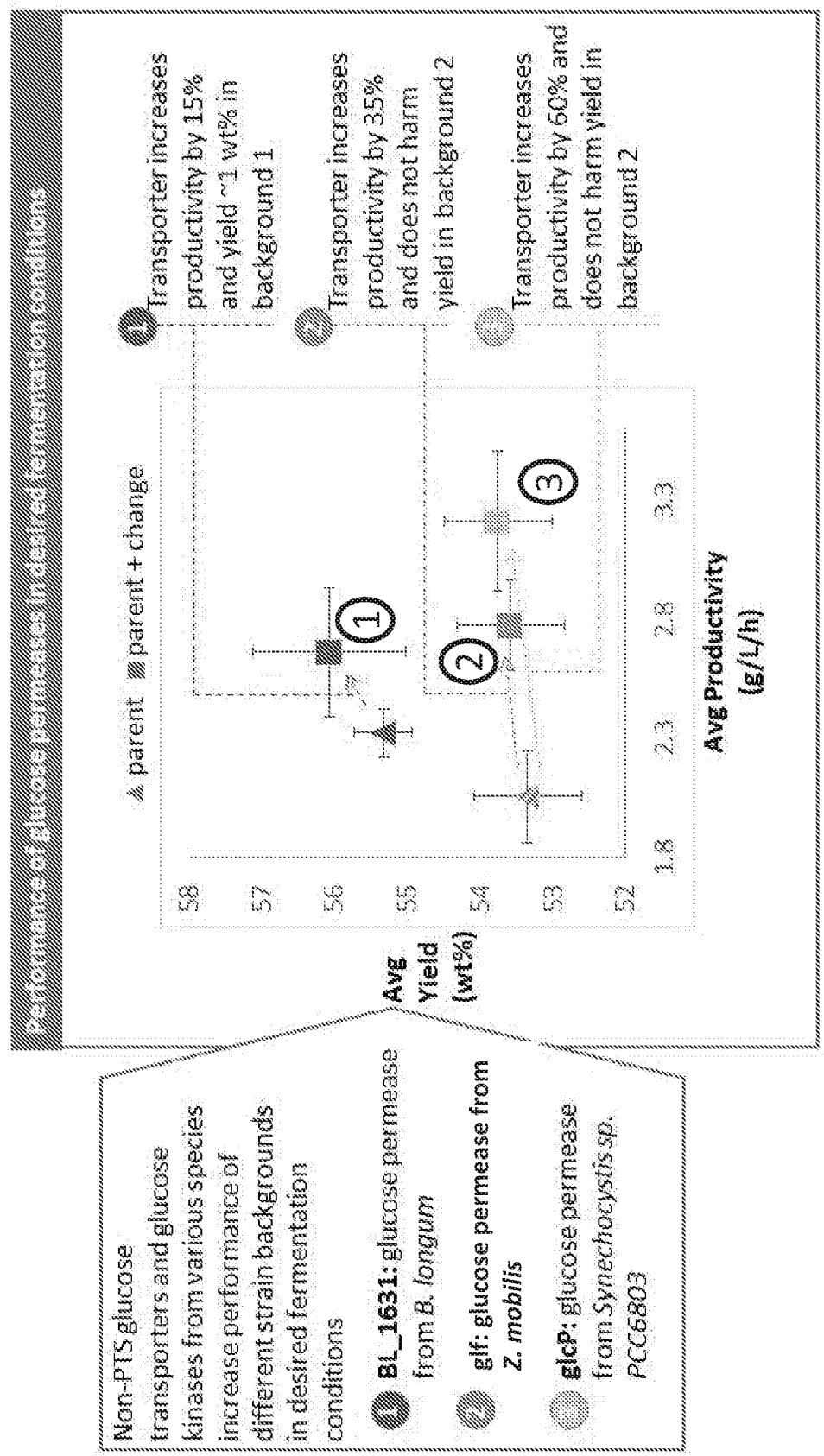
FIG. 2 illustrates performance of glucose permeases in desired fermentation conditions as described in Example 1.

As shown in FIG. 2, the BL_1631 glucose permease-C. glutamicum ppgK kinase construct increased productivity of the host cell with background 1 by 15% as well as increased the yield by about 1%. In addition, in host cell with background 2, both the glk permease-glk kinase construct and the glcP permease—C. glutamicum ppgK kinase construct increased productivity by more than 30%, but did not affect yield. Accordingly, this example shows that the methods provided herein can be used to increase the performance of microbial strains in terms of producing fermentation end products.

INCORPORATION BY REFERENCE

The following applications are hereby incorporated by reference in their entirety, including all descriptions, references, figures, and claims for all purposes: U.S. application Ser. No. 15/396,230, filed on Dec. 30, 2016; International Application No. PCT/US2016/065465, filed on Dec. 7, 2016; U.S. application Ser. No. 15/140,296, filed on Apr. 27, 2016; U.S. Provisional Application No. 62/368,786, filed on Jul. 29, 2016; and U.S. Provisional Application No. 62/264,232, filed on Dec. 7, 2015.

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A host cell comprising a heterologous glucose permease gene functionally linked to a first promoter polynucleotide, wherein the first promoter polynucleotide comprises a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

2. The host cell of claim 1, wherein the glucose permease gene is a gene that encodes a polypeptide with an amino acid sequence selected from SEQ ID NO: 13, SEQ ID NO: 10, SEQ ID NO: 11, SEQ ID NO: 12, SEQ ID NO: 9 and SEQ ID NO: 14.

3. The host cell of claim 1, wherein the glucose permease gene is a gene with a nucleotide sequence selected from SEQ ID NO: 23, SEQ ID NO: 20, SEQ ID NO: 21, SEQ ID NO: 22, SEQ ID NO: 19 and SEQ ID NO: 24.

4. The host cell of claim 1, further comprising a hexokinase gene functionally linked to a second promoter polynucleotide, wherein the second promoter polynucleotide comprises a nucleotide sequence selected from SEQ ID NO: 2, SEQ ID NO: 1, SEQ ID NO: 3, SEQ ID NO: 4, SEQ ID NO: 5, SEQ ID NO: 6, SEQ ID NO: 7, and SEQ ID NO: 8.

5. The host cell of claim 4, wherein the hexokinase gene is a gene that encodes a polypeptide sequence selected from SEQ ID NO: 15 and SEQ ID NO: 16.

6. The host cell of claim 4, wherein the hexokinase gene is a gene with a nucleotide sequence selected from SEQ ID NO: 25 and SEQ ID NO: 26.

7. A method for generating a microorganism capable of increased production of a biomolecule from glucose, the method comprising:
a) genetically modifying a host microorganism, wherein the modifying comprises introducing a glucose permease gene from a library of glucose permease genes into the genome of the host microorganism, wherein each glucose permease gene from the library of glucose permease genes is functionally linked to a promoter comprising a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 and wherein the modification generates a strain of the host microorganism expressing the glucose permease gene;
b) repeating step a) for a plurality of rounds until a plurality of strains of the host microorganism are generated, wherein each strain of the plurality of strains of the host microorganism expresses a separate glucose permease gene from the library of glucose permease genes;
c) contacting each strain of the plurality of strains of the host microorganism with a carbon source comprising glucose under fermentative conditions; and
d) selecting each strain of the host microorganism that produces an increased amount of a biomolecule from glucose as compared to the amount of the biomolecule produce from glucose from a control microorganism, wherein the control microorganism does not express a glucose permease gene from the library of glucose permease genes.

8. The method of claim 7, wherein the library of glucose permease genes comprises genes that encode polypeptide sequences of SEQ ID NO: 13, SEQ ID NO: 10, SEQ ID NO: 11, SEQ ID NO: 12, SEQ ID NO: 9, SEQ ID NO: 14 or a combination thereof.

9. The method of claim 7, wherein the library of glucose permease genes comprises genes with a nucleotide sequence of SEQ ID NO: 23, SEQ ID NO: 20, SEQ ID NO: 21, SEQ ID NO: 22, SEQ ID NO: 19, SEQ ID NO: 24 or a combination thereof.

10. The method of claim 7, further comprising introducing a hexokinase gene from a library of hexokinase genes, wherein each hexokinase gene from the library of hexokinase genes is functionally linked to a promoter polynucleotide, wherein the promoter polynucleotide comprises a sequence selected from SEQ ID NO: 2, SEQ ID NO: 1, SEQ ID NO: 3, SEQ ID NO: 4, SEQ ID NO: 5, SEQ ID NO: 6, SEQ ID NO: 7, and SEQ ID NO: 8.

11. The method of claim 10, wherein the library of hexokinase genes comprises genes that encode polypeptide sequences of SEQ ID NO: 15 and/or SEQ ID NO: 16.

12. The method of claim 10, wherein the library of hexokinase genes comprises genes with nucleotide sequences of SEQ ID NO: 25 and/or SEQ ID NO: 26.

13. A library of glucose permease genes, wherein each glucose permease gene in the library of glucose permease genes is functionally linked to a promoter comprising a nucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

14. The library of claim 13, wherein the library of glucose permease genes comprises genes that encode polypeptide sequences of SEQ ID NO: 13, SEQ ID NO: 10, SEQ ID NO: 11, SEQ ID NO: 12, SEQ ID NO: 9, SEQ ID NO: 14 or a combination thereof.

15. The library of claim 13, wherein the library of glucose permease genes comprises genes with nucleotide sequences of SEQ ID NO: 23, SEQ ID NO: 20, SEQ ID NO: 21, SEQ ID NO: 22, SEQ ID NO: 19, SEQ ID NO: 24 or a combination thereof.

16. The library of claim 13, wherein each glucose permease gene in the library of glucose permease genes is a first portion of a chimeric construct, wherein the chimeric construct comprises a second portion, wherein the second portion is a hexokinase gene.

17. The library of claim 16, wherein the hexokinase gene is functionally linked to a promoter polynucleotide, wherein the promoter polynucleotide comprises a sequence selected from SEQ ID NO: 2, SEQ ID NO: 1, SEQ ID NO: 3, SEQ ID NO: 4, SEQ ID NO: 5, SEQ ID NO: 6, SEQ ID NO: 7, and SEQ ID NO: 8.

18. The library of claim 17, wherein the library of hexokinase genes comprises genes that encode polypeptide sequences of SEQ ID NO: 15 and or SEQ ID NO: 16.

19. The library of claim 17, wherein the library of hexokinase genes comprises genes with nucleotide sequences of SEQ ID NO: 25 and/or SEQ ID NO: 26.

20. A method of producing a biomolecule comprising introducing a glucose permease gene from the library of claim 13, into a host cell and culturing the host cell under conditions suitable for producing the biomolecule.

* * * * *

SEQUENCE LISTING

```
<160> NUMBER OF SEQ ID NOS: 26

<210> SEQ ID NO 1
<211> LENGTH: 97
<212> TYPE: DNA
<213> ORGANISM: Corynebacterium glutamicum
<220> FEATURE:
<221> NAME/KEY: misc_feature
<222> LOCATION: (1)..(97)
<223> OTHER INFORMATION: Pcg0007_39
```

-continued

```
<400> SEQUENCE: 1
tgccgtttct cgcgttgtgt gtggtactac gtggggacct aagcgtgtat tatggaaacg        60
tctgtatcgg ataagtagcg aggagtgttc gttaaaa                                 97

<210> SEQ ID NO 2
<211> LENGTH: 97
<212> TYPE: DNA
<213> ORGANISM: Corynebacterium glutamicum
<220> FEATURE:
<221> NAME/KEY: misc_feature
<222> LOCATION: (1)..(97)
<223> OTHER INFORMATION: Pcg0007

<400> SEQUENCE: 2
tgccgtttct cgcgttgtgt gtggtactac gtggggacct aagcgtgtaa gatggaaacg        60
tctgtatcgg ataagtagcg aggagtgttc gttaaaa                                 97

<210> SEQ ID NO 3
<211> LENGTH: 93
<212> TYPE: DNA
<213> ORGANISM: Corynebacterium glutamicum
<220> FEATURE:
<221> NAME/KEY: misc_feature
<222> LOCATION: (1)..(93)
<223> OTHER INFORMATION: Pcg1860

<400> SEQUENCE: 3
cttagctttg acctgcacaa atagttgcaa attgtcccac atacacataa agtagcttgc        60
gtatttaaaa ttatgaacct aaggggttta gca                                     93

<210> SEQ ID NO 4
<211> LENGTH: 98
<212> TYPE: DNA
<213> ORGANISM: Corynebacterium glutamicum
<220> FEATURE:
<221> NAME/KEY: misc_feature
<222> LOCATION: (1)..(98)
<223> OTHER INFORMATION: Pcg0755

<400> SEQUENCE: 4
aataaattta taccacacag tctattgcaa tagaccaagc tgttcagtag ggtgcatggg        60
agaagaattt cctaataaaa actcttaagg acctccaa                                98

<210> SEQ ID NO 5
<211> LENGTH: 97
<212> TYPE: DNA
<213> ORGANISM: Corynebacterium glutamicum
<220> FEATURE:
<221> NAME/KEY: misc_feature
<222> LOCATION: (1)..(97)
<223> OTHER INFORMATION: Pcg0007_265

<400> SEQUENCE: 5
tgccgtttct cgcgttgtgt gtggtactac gtggggacct aagcgtgtac gctggaaacg        60
tctgtatcgg ataagtagcg aggagtgttc gttaaaa                                 97

<210> SEQ ID NO 6
<211> LENGTH: 86
<212> TYPE: DNA
<213> ORGANISM: Corynebacterium glutamicum
<220> FEATURE:
<221> NAME/KEY: misc_feature
<222> LOCATION: (1)..(86)
<223> OTHER INFORMATION: Pcg3381
```

<400> SEQUENCE: 6

```
cgccggataa atgaattgat tattttaggc tcccagggat taagtctagg gtggaatgca      60
gaaatatttc ctacggaagg tccgtt                                          86
```

<210> SEQ ID NO 7
<211> LENGTH: 97
<212> TYPE: DNA
<213> ORGANISM: Corynebacterium glutamicum
<220> FEATURE:
<221> NAME/KEY: misc_feature
<222> LOCATION: (1)..(97)
<223> OTHER INFORMATION: Pcg0007_119

<400> SEQUENCE: 7

```
tgccgtttct cgcgttgtgt gtggtactac gtggggacct aagcgtgttg catggaaacg      60
tctgtatcgg ataagtagcg aggagtgttc gttaaaa                              97
```

<210> SEQ ID NO 8
<211> LENGTH: 87
<212> TYPE: DNA
<213> ORGANISM: Corynebacterium glutamicum
<220> FEATURE:
<221> NAME/KEY: misc_feature
<222> LOCATION: (1)..(87)
<223> OTHER INFORMATION: Pcg3121

<400> SEQUENCE: 8

```
gtggctaaaa cttttggaaa cttaagttac ctttaatcgg aaacttattg aattcgggtg      60
aggcaactgc aactctggac ttaaagc                                         87
```

<210> SEQ ID NO 9
<211> LENGTH: 485
<212> TYPE: PRT
<213> ORGANISM: Mycobacterium smegmatis
<220> FEATURE:
<221> NAME/KEY: MISC_FEATURE
<222> LOCATION: (1)..(485)
<223> OTHER INFORMATION: MSMEG_4187

<400> SEQUENCE: 9

Met Arg Gln Thr Gly Ser Leu Arg Pro Ile Leu Val Pro Val Trp Ile
1               5                   10                  15

Leu Val Leu Val Ala Ala Leu Ala Gly Cys Ala Thr Arg Thr Asp Asp
                20                  25                  30

Gln Pro Thr Glu Ser Ala Pro Pro Ala Gln Gln Ala Pro Pro Thr
        35                  40                  45

Pro Ala Glu Ile Arg Ala Ile Ala Lys Asp Ala Tyr Ile Trp Gly Phe
    50                  55                  60

Pro Leu Val Asp Asn Tyr Arg Val Gln Tyr Ser Tyr Phe Val Asp Lys
65                  70                  75                  80

Thr Asp Pro Glu Tyr Lys Gly Gly Phe Asn Glu Val His Asn Thr Ala
                85                  90                  95

Arg Leu Tyr Thr Pro Ala Asp Lys Ala Ile Gln Thr Pro Asn Ala Asp
                100                 105                 110

Thr Pro Tyr Ser Phe Val Gly Ala Asp Leu Arg Thr Glu Pro Leu Val
        115                 120                 125

Phe Thr Val Pro Pro Ile Glu Gln Asn Arg Tyr Phe Ser Leu Gln Phe
    130                 135                 140

Val Asp Gly Tyr Thr Tyr Asn Val Ala Tyr Val Gly Ser Arg Thr Thr

```
            145                 150                 155                 160
        Gly Asn Gly Gly Gly Arg Tyr Leu Leu Ala Gly Pro Gly Trp Glu Gly
                        165                 170                 175

Glu Lys Pro Glu Gly Val Asp Glu Ile Ile Arg Ser Asp Thr Asp Leu
                    180                 185                 190

Ala Phe Val Leu Tyr Arg Thr Gln Leu Phe Gly Pro Arg Asp Leu Asp
                    195                 200                 205

Asn Ile Lys Lys Ile Gln Ala Gly Tyr Gln Val Ala Pro Leu Ser Val
                210                 215                 220

Tyr Leu Lys Gln Pro Ser Pro Pro Ala Pro Ile Asp Phe Thr
        225                 230                 235                 240

Pro Pro Leu Thr Pro Glu Ala Gln Lys Thr Ser Pro Gln Phe Phe Glu
                        245                 250                 255

Ile Leu Asn Ala Ala Leu Arg Tyr Ala Pro Val Lys Pro Glu Glu Gln
                        260                 265                 270

Glu Met Arg Glu Arg Phe Ala Arg Ile Gly Ile Gly Pro Asp Gly Asp
                    275                 280                 285

Phe Asp Ala Asp Lys Leu Ser Pro Glu Thr Arg Glu Ala Ile Glu Asp
        290                 295                 300

Gly Met Ala Asn Ala Trp Val Glu Phe Asp Arg Phe Lys Gln Asp Lys
        305                 310                 315                 320

Val Asp Thr Gly Glu Val Gly Ser Ala Gln Leu Phe Gly Thr Ala Asp
                        325                 330                 335

Asp Leu Lys Gly Asn Tyr Leu Tyr Arg Met Ala Gly Ala Val Leu Gly
                    340                 345                 350

Ile Tyr Gly Asn Thr Ala Ala Glu Ala Leu Tyr Pro Ser Ala Met Leu
                    355                 360                 365

Asp Ala Asp Gly Gln Pro Leu Thr Gly Thr Asn Ser Tyr Thr Tyr Arg
                370                 375                 380

Phe Ala Pro Asp Gln Leu Pro Pro Val Asn Ala Phe Trp Ser Leu Thr
        385                 390                 395                 400

Ile Tyr Glu Leu Pro Ser Ser Gln Leu Val Asp Asn Pro Ile Asp Arg
                        405                 410                 415

Tyr Leu Ile Asn Ser Glu Met Leu Pro Ser Leu Val Pro Asp Pro Asp
                        420                 425                 430

Gly Ala Tyr Thr Leu Arg Ile Gln Asn Thr Gln Pro Pro Glu Asn Glu
                    435                 440                 445

Ala Asn Trp Leu Pro Ala Pro Lys Gly Pro Phe Thr Leu Val Leu Arg
            450                 455                 460

Leu Tyr Trp Pro Lys Pro Asp Ala Leu Asn Gly Thr Trp Gln Ala Pro
        465                 470                 475                 480

Lys Pro Glu Lys Ile
                    485

<210> SEQ ID NO 10
<211> LENGTH: 471
<212> TYPE: PRT
<213> ORGANISM: Streptomyces coelicolor
<220> FEATURE:
<221> NAME/KEY: MISC_FEATURE
<222> LOCATION: (1)..(471)
<223> OTHER INFORMATION: SCO5578

<400> SEQUENCE: 10

Met Ala Ser Thr Ser Gln Ala Pro Ser Pro Gly Ala Gly Thr Ala His
1               5                   10                  15
```

```
Pro Asp His Leu Gly His Val Ile Phe Ile Ala Ala Ala Ala Met
            20              25              30

Gly Gly Phe Leu Phe Gly Tyr Asp Ser Ser Val Ile Asn Gly Ala Val
            35              40              45

Glu Ala Ile Arg Asp Arg Tyr Asp Val Gly Ser Ala Val Leu Ala Gln
 50              55              60

Val Ile Ala Val Ala Leu Ile Gly Cys Ala Ile Gly Ala Ala Thr Ala
 65              70              75              80

Gly Arg Ile Ala Asp Arg Ile Gly Arg Ile Arg Cys Met Gln Ile Ala
                85              90              95

Ala Val Leu Phe Thr Val Ser Ala Val Gly Ser Ala Leu Pro Phe Ala
            100             105             110

Leu Trp Asp Leu Ala Met Trp Arg Ile Ile Gly Gly Phe Ala Ile Gly
            115             120             125

Met Ala Ser Val Ile Gly Pro Ala Tyr Ile Ala Glu Val Ser Pro Pro
 130             135             140

Ala Tyr Arg Gly Arg Leu Gly Ser Phe Gln Gln Ala Ala Ile Val Ile
145             150             155             160

Gly Ile Ala Val Ser Gln Leu Val Asn Trp Gly Leu Leu Asn Ala Ala
                165             170             175

Gly Gly Asp Gln Arg Gly Glu Leu Met Gly Leu Glu Ala Trp Gln Val
            180             185             190

Met Leu Gly Val Met Val Ile Pro Ala Val Leu Tyr Gly Leu Leu Ser
            195             200             205

Phe Ala Ile Pro Glu Ser Pro Arg Phe Leu Ile Ser Val Gly Lys Arg
            210             215             220

Glu Arg Ala Lys Lys Ile Leu Glu Glu Val Glu Gly Lys Asp Val Asp
225             230             235             240

Phe Asp Ala Arg Val Thr Glu Ile Glu His Ala Met His Arg Glu Glu
            245             250             255

Lys Ser Ser Phe Lys Asp Leu Leu Gly Gly Ser Phe Phe Lys Pro
            260             265             270

Ile Val Trp Ile Gly Ile Gly Leu Ser Val Phe Gln Gln Phe Gly Ile
            275             280             285

Asn Val Ala Phe Tyr Tyr Ser Ser Thr Leu Trp Gln Ser Val Gly Val
290             295             300

Asp Pro Ala Asp Ser Phe Phe Tyr Ser Phe Thr Thr Ser Ile Ile Asn
305             310             315             320

Ile Val Gly Thr Val Ile Ala Met Ile Phe Val Asp Arg Val Gly Arg
                325             330             335

Lys Pro Leu Ala Leu Ile Gly Ser Val Gly Met Val Ile Gly Leu Ala
            340             345             350

Leu Glu Ala Trp Ala Phe Ser Phe Asp Leu Val Asp Gly Lys Leu Pro
            355             360             365

Ala Thr Gln Gly Trp Val Ala Leu Ile Ala Ala His Val Phe Val Leu
            370             375             380

Phe Phe Ala Leu Ser Trp Gly Val Val Trp Val Phe Leu Gly Glu
385             390             395             400

Met Phe Pro Asn Arg Ile Arg Ala Ala Leu Gly Val Ala Ala Ser
            405             410             415

Ala Gln Trp Ile Ala Asn Trp Ala Ile Thr Ala Ser Phe Pro Ser Leu
            420             425             430
```

```
Ala Asp Trp Asn Leu Ser Gly Thr Tyr Val Ile Tyr Thr Ile Phe Ala
            435                 440                 445

Ala Leu Ser Ile Pro Phe Val Leu Lys Phe Val Lys Glu Thr Lys Gly
        450                 455                 460

Lys Ala Leu Glu Glu Met Gly
465                 470

<210> SEQ ID NO 11
<211> LENGTH: 517
<212> TYPE: PRT
<213> ORGANISM: Bifidobacterium longum
<220> FEATURE:
<221> NAME/KEY: MISC_FEATURE
<222> LOCATION: (1)..(517)
<223> OTHER INFORMATION: BL1631

<400> SEQUENCE: 11

Met Thr Thr Thr Thr Ala Ser Pro Val Ser Lys Gln Thr Ala Ser Ala
1               5                   10                  15

Ala Gln Glu Thr Ser Ala Thr Gly Ala Ala Thr Ala Ile Glu Thr
            20                  25                  30

Ile Glu Thr Gly Val Ala Gly Val Ala Gly Ala Ala Thr Asn Ala Ala
            35                  40                  45

Ala Asn Ala Ile Glu Asp Leu Glu Ala Ala Glu Ser His Gly Phe Ser
        50                  55                  60

Thr Arg Phe Pro Leu Asn Ser Ala Phe Ile Phe Thr Phe Gly Ala Leu
65                  70                  75                  80

Gly Gly Met Leu Phe Gly Phe Asp Thr Gly Ile Ile Ser Gly Ala Ser
                85                  90                  95

Pro Leu Ile Glu Ser Asp Phe Gly Leu Ser Val Ser Gln Thr Gly Phe
            100                 105                 110

Ile Thr Ser Ser Val Leu Ile Gly Ser Cys Ala Gly Ala Leu Ser Ile
        115                 120                 125

Gly Ala Leu Ser Asp Arg Phe Gly Arg Lys Lys Leu Leu Ile Val Ser
    130                 135                 140

Ala Leu Leu Phe Leu Leu Gly Ser Gly Leu Cys Ala Ser Ser Thr Gly
145                 150                 155                 160

Phe Ala Met Met Val Cys Ala Arg Ile Ile Leu Gly Leu Ala Val Gly
                165                 170                 175

Ala Ala Ser Ala Leu Thr Pro Ala Tyr Leu Ala Glu Leu Ala Pro Lys
            180                 185                 190

Glu Arg Arg Gly Ser Leu Ser Thr Leu Phe Gln Leu Met Val Thr Phe
        195                 200                 205

Gly Ile Leu Leu Ala Tyr Ala Ser Asn Leu Gly Phe Leu Asn His Asn
    210                 215                 220

Leu Phe Gly Ile Arg Asp Trp Arg Trp Met Leu Gly Ser Ala Leu Val
225                 230                 235                 240

Pro Ala Ala Leu Leu Leu Gly Gly Leu Leu Pro Glu Ser Pro
                245                 250                 255

Arg Tyr Leu Val Asn Lys Gly Asp Thr Arg Asn Ala Phe Lys Val Leu
            260                 265                 270

Thr Leu Ile Arg Lys Asp Val Asp Gln Thr Gln Val Gln Ile Glu Leu
        275                 280                 285

Asp Glu Ile Lys Ala Val Ala Ala Gln Asp Thr Lys Gly Gly Val Arg
    290                 295                 300

Glu Leu Phe Arg Ile Ala Arg Pro Ala Leu Val Ala Ala Ile Gly Ile
```

```
                    305                 310                 315                 320

Met Leu Phe Gln Gln Leu Val Gly Ile Asn Ser Val Ile Tyr Phe Leu
                        325                 330                 335

Pro Gln Val Phe Ile Lys Gly Phe Gly Phe Pro Glu Gly Asp Ala Ile
                        340                 345                 350

Trp Val Ser Val Gly Ile Gly Val Asn Phe Val Ser Thr Ile Val
                        355                 360                 365

Ala Thr Leu Ile Met Asp Arg Phe Pro Arg Lys Gly Met Leu Ile Phe
                        370                 375                 380

Gly Ser Ile Val Met Thr Val Ser Leu Ala Val Leu Ala Val Met Asn
        385                 390                 395                 400

Phe Val Gly Asp Val Ala Val Leu Ala Val Pro Thr Met Ile Leu Ile
                            405                 410                 415

Ala Phe Tyr Ile Leu Gly Phe Ala Val Ser Trp Gly Pro Ile Ala Trp
                        420                 425                 430

Val Leu Ile Gly Glu Ile Phe Pro Leu Ser Val Arg Gly Ile Gly Ser
                        435                 440                 445

Ser Phe Gly Ser Ala Ala Asn Trp Leu Gly Asn Phe Ile Val Ser Gln
                        450                 455                 460

Phe Phe Leu Val Leu Leu Asp Ala Phe Gly Asn Asn Val Gly Gly Pro
        465                 470                 475                 480

Phe Ala Ile Phe Gly Val Phe Ser Ala Leu Ser Ile Pro Phe Val Leu
                        485                 490                 495

Arg Leu Val Pro Glu Thr Lys Gly Lys Ser Leu Glu Glu Ile Glu Lys
                        500                 505                 510

Glu Met Thr Lys Arg
                        515

<210> SEQ ID NO 12
<211> LENGTH: 468
<212> TYPE: PRT
<213> ORGANISM: Synechocystis sp. PCC6803
<220> FEATURE:
<221> NAME/KEY: MISC_FEATURE
<222> LOCATION: (1)..(468)
<223> OTHER INFORMATION: glcp (CAA34119.1)

<400> SEQUENCE: 12

Met Asn Pro Ser Ser Pro Ser Gln Ser Thr Ala Asn Val Lys Phe
        1               5                   10                  15

Val Leu Leu Ile Ser Gly Val Ala Ala Leu Gly Gly Phe Leu Phe Gly
                        20                  25                  30

Phe Asp Thr Ala Val Ile Asn Gly Ala Val Ala Ala Leu Gln Lys His
                        35                  40                  45

Phe Gln Thr Asp Ser Leu Leu Thr Gly Leu Ser Val Ser Leu Ala Leu
                50                  55                  60

Leu Gly Ser Ala Leu Gly Ala Phe Gly Ala Gly Pro Ile Ala Asp Arg
        65                  70                  75                  80

His Gly Arg Ile Lys Thr Met Ile Leu Ala Ala Val Leu Phe Thr Leu
                        85                  90                  95

Ser Ser Ile Gly Ser Gly Leu Pro Phe Thr Ile Trp Asp Phe Ile Phe
                        100                 105                 110

Trp Arg Val Leu Gly Gly Ile Gly Val Gly Ala Ala Ser Val Ile Ala
                        115                 120                 125

Pro Ala Tyr Ile Ala Glu Val Ser Pro Ala His Leu Arg Gly Arg Leu
                        130                 135                 140
```

Gly Ser Leu Gln Gln Leu Ala Ile Val Ser Gly Ile Phe Ile Ala Leu
145                 150                 155                 160

Leu Ser Asn Trp Phe Ile Ala Leu Met Ala Gly Gly Ser Ala Gln Asn
            165                 170                 175

Pro Trp Leu Phe Gly Ala Ala Trp Arg Trp Met Phe Trp Thr Glu
        180                 185                 190

Leu Ile Pro Ala Leu Leu Tyr Gly Val Cys Ala Phe Leu Ile Pro Glu
            195                 200                 205

Ser Pro Arg Tyr Leu Val Ala Gln Gly Gln Gly Glu Lys Ala Ala Ala
210                 215                 220

Ile Leu Trp Lys Val Glu Gly Gly Asp Val Pro Ser Arg Ile Glu Glu
225                 230                 235                 240

Ile Gln Ala Thr Val Ser Leu Asp His Lys Pro Arg Phe Ser Asp Leu
            245                 250                 255

Leu Ser Arg Arg Gly Gly Leu Leu Pro Ile Val Trp Ile Gly Met Gly
            260                 265                 270

Leu Ser Ala Leu Gln Gln Phe Val Gly Ile Asn Val Ile Phe Tyr Tyr
            275                 280                 285

Ser Ser Val Leu Trp Arg Ser Val Gly Phe Thr Glu Glu Lys Ser Leu
290                 295                 300

Leu Ile Thr Val Ile Thr Gly Phe Ile Asn Ile Leu Thr Thr Ile Val
305                 310                 315                 320

Ala Ile Ala Phe Val Asp Lys Phe Gly Arg Lys Pro Leu Leu Leu Met
            325                 330                 335

Gly Ser Ile Gly Met Thr Ile Thr Leu Gly Ile Leu Ser Val Val Phe
            340                 345                 350

Gly Gly Ala Thr Val Val Asn Gly Gln Pro Thr Leu Thr Gly Ala Ala
            355                 360                 365

Gly Ile Ile Ala Leu Val Thr Ala Asn Leu Tyr Val Phe Ser Phe Gly
            370                 375                 380

Phe Ser Trp Gly Pro Ile Val Trp Val Leu Leu Gly Glu Met Phe Asn
385                 390                 395                 400

Asn Lys Ile Arg Ala Ala Ala Leu Ser Val Ala Ala Gly Val Gln Trp
            405                 410                 415

Ile Ala Asn Phe Ile Ile Ser Thr Thr Phe Pro Pro Leu Leu Asp Thr
            420                 425                 430

Val Gly Leu Gly Pro Ala Tyr Gly Leu Tyr Ala Thr Ser Ala Ala Ile
            435                 440                 445

Ser Ile Phe Phe Ile Trp Phe Phe Val Lys Glu Thr Lys Gly Lys Thr
            450                 455                 460

Leu Glu Gln Met
465

<210> SEQ ID NO 13
<211> LENGTH: 473
<212> TYPE: PRT
<213> ORGANISM: Zymomonas mobilis
<220> FEATURE:
<221> NAME/KEY: MISC_FEATURE
<222> LOCATION: (1)..(473)
<223> OTHER INFORMATION: glf permease

<400> SEQUENCE: 13

Met Ser Ser Glu Ser Ser Gln Gly Leu Val Thr Arg Leu Ala Leu Ile
1               5                   10                  15

-continued

```
Ala Ala Ile Gly Gly Leu Leu Phe Gly Tyr Asp Ser Ala Val Ile Ala
            20                  25                  30
Ala Ile Gly Thr Pro Val Asp Ile His Phe Ile Ala Pro Arg His Leu
        35                  40                  45
Ser Ala Thr Ala Ala Ala Ser Leu Ser Gly Met Val Val Ala Val
50                  55                  60
Leu Val Gly Cys Val Thr Gly Ser Leu Leu Ser Gly Trp Ile Gly Ile
65                  70                  75                  80
Arg Phe Gly Arg Arg Gly Gly Leu Leu Met Ser Ser Ile Cys Phe Val
                85                  90                  95
Ala Ala Gly Phe Gly Ala Ala Leu Thr Glu Lys Leu Phe Gly Thr Gly
                100                 105                 110
Gly Ser Ala Leu Gln Ile Phe Cys Phe Phe Arg Phe Leu Ala Gly Leu
            115                 120                 125
Gly Ile Gly Val Val Ser Thr Leu Thr Pro Thr Tyr Ile Ala Glu Ile
        130                 135                 140
Ala Pro Pro Asp Lys Arg Gly Gln Met Val Ser Gly Gln Gln Met Ala
145                 150                 155                 160
Ile Val Thr Gly Ala Leu Thr Gly Tyr Ile Phe Thr Trp Leu Leu Ala
                165                 170                 175
His Phe Gly Ser Ile Asp Trp Val Asn Ala Ser Gly Trp Cys Trp Ser
                180                 185                 190
Pro Ala Ser Glu Gly Leu Ile Gly Ile Ala Phe Leu Leu Leu Leu Leu
            195                 200                 205
Thr Ala Pro Asp Thr Pro His Trp Leu Val Met Lys Gly Arg His Ser
        210                 215                 220
Glu Ala Ser Lys Ile Leu Ala Arg Leu Glu Pro Gln Ala Asp Pro Asn
225                 230                 235                 240
Leu Thr Ile Gln Lys Ile Lys Ala Gly Phe Asp Lys Ala Met Asp Lys
                245                 250                 255
Ser Ser Ala Gly Leu Phe Ala Phe Gly Ile Thr Val Val Phe Ala Gly
                260                 265                 270
Val Ser Val Ala Ala Phe Gln Gln Leu Val Gly Ile Asn Ala Val Leu
            275                 280                 285
Tyr Tyr Ala Pro Gln Met Phe Gln Asn Leu Gly Phe Gly Ala Asp Thr
        290                 295                 300
Ala Leu Leu Gln Thr Ile Ser Ile Gly Val Val Asn Phe Ile Phe Thr
305                 310                 315                 320
Met Ile Ala Ser Arg Val Val Asp Arg Phe Gly Arg Lys Pro Leu Leu
                325                 330                 335
Ile Trp Gly Ala Leu Gly Met Ala Ala Met Met Ala Val Leu Gly Cys
                340                 345                 350
Cys Phe Trp Phe Lys Val Gly Val Leu Pro Leu Ala Ser Val Leu
            355                 360                 365
Leu Tyr Ile Ala Val Phe Gly Met Ser Trp Gly Pro Val Cys Trp Val
        370                 375                 380
Val Leu Ser Glu Met Phe Pro Ser Ser Ile Lys Gly Ala Ala Met Pro
385                 390                 395                 400
Ile Ala Val Thr Gly Gln Trp Leu Ala Asn Ile Leu Val Asn Phe Leu
                405                 410                 415
Phe Lys Val Ala Asp Gly Ser Pro Ala Leu Asn Gln Thr Phe Asn His
                420                 425                 430
Gly Phe Ser Tyr Leu Val Phe Ala Ala Leu Ser Ile Leu Gly Gly Leu
```

```
            435                 440                 445
Ile Val Ala Arg Phe Val Pro Glu Thr Lys Gly Arg Ser Leu Asp Glu
    450                 455                 460

Ile Glu Glu Met Trp Arg Ser Gln Lys
465                 470

<210> SEQ ID NO 14
<211> LENGTH: 491
<212> TYPE: PRT
<213> ORGANISM: Corynebacterium glutamicum
<220> FEATURE:
<221> NAME/KEY: MISC_FEATURE
<222> LOCATION: (1)..(491)
<223> OTHER INFORMATION: iolT1

<400> SEQUENCE: 14

Met Ala Ser Thr Phe Ile Gln Ala Asp Ser Pro Glu Lys Ser Lys Lys
1               5                   10                  15

Leu Pro Pro Leu Thr Glu Gly Pro Tyr Arg Lys Arg Leu Phe Tyr Val
            20                  25                  30

Ala Leu Val Ala Thr Phe Gly Gly Leu Leu Phe Gly Tyr Asp Thr Gly
        35                  40                  45

Val Ile Asn Gly Ala Leu Asn Pro Met Thr Arg Glu Leu Gly Leu Thr
    50                  55                  60

Ala Phe Thr Glu Gly Val Val Thr Ser Ser Leu Leu Phe Gly Ala Ala
65                  70                  75                  80

Ala Gly Ala Met Phe Phe Gly Arg Ile Ser Asp Asn Trp Gly Arg Arg
                85                  90                  95

Lys Thr Ile Ile Ser Leu Ala Val Ala Phe Phe Val Gly Thr Met Ile
            100                 105                 110

Cys Val Phe Ala Pro Ser Phe Ala Val Met Val Val Gly Arg Val Leu
        115                 120                 125

Leu Gly Leu Ala Val Gly Gly Ala Ser Thr Val Val Pro Val Tyr Leu
    130                 135                 140

Ala Glu Leu Ala Pro Phe Glu Ile Arg Gly Ser Leu Ala Gly Arg Asn
145                 150                 155                 160

Glu Leu Met Ile Val Val Gly Gln Leu Ala Ala Phe Val Ile Asn Ala
                165                 170                 175

Ile Ile Gly Asn Val Phe Gly His His Asp Gly Val Trp Arg Tyr Met
            180                 185                 190

Leu Ala Ile Ala Ala Ile Pro Ala Ile Ala Leu Phe Phe Gly Met Leu
        195                 200                 205

Arg Val Pro Glu Ser Pro Arg Trp Leu Val Glu Arg Gly Arg Ile Asp
    210                 215                 220

Glu Ala Arg Ala Val Leu Glu Thr Ile Arg Pro Leu Glu Arg Ala His
225                 230                 235                 240

Ala Glu Val Ala Asp Val Glu His Leu Ala Arg Glu Glu His Ala Val
                245                 250                 255

Ser Glu Lys Ser Met Gly Leu Arg Glu Ile Leu Ser Ser Lys Trp Leu
            260                 265                 270

Val Arg Ile Leu Leu Val Gly Ile Gly Leu Gly Val Ala Gln Gln Leu
        275                 280                 285

Thr Gly Ile Asn Ser Ile Met Tyr Tyr Gly Gln Val Val Leu Ile Glu
    290                 295                 300

Ala Gly Phe Ser Glu Asn Ala Ala Leu Ile Ala Asn Val Ala Pro Gly
305                 310                 315                 320
```

```
Val Ile Ala Val Val Gly Ala Phe Ile Ala Leu Trp Met Met Asp Arg
                325                 330                 335

Ile Asn Arg Arg Thr Thr Leu Ile Thr Gly Tyr Ser Leu Thr Thr Ile
                340                 345                 350

Ser His Val Leu Ile Gly Ile Ala Ser Val Ala Phe Pro Val Gly Asp
                355                 360                 365

Pro Leu Arg Pro Tyr Val Ile Leu Thr Leu Val Val Phe Val Gly
            370                 375                 380

Ser Met Gln Thr Phe Leu Asn Val Ala Thr Trp Val Met Leu Ser Glu
385                 390                 395                 400

Leu Phe Pro Leu Ala Met Arg Gly Phe Ala Ile Gly Ile Ser Val Phe
                405                 410                 415

Phe Leu Trp Ile Ala Asn Ala Phe Leu Gly Leu Phe Phe Pro Thr Ile
                420                 425                 430

Met Glu Ala Val Gly Leu Thr Gly Thr Phe Phe Met Phe Ala Gly Ile
                435                 440                 445

Gly Val Val Ala Leu Ile Phe Ile Tyr Thr Gln Val Pro Glu Thr Arg
                450                 455                 460

Gly Arg Thr Leu Glu Glu Ile Asp Glu Asp Val Thr Ser Gly Val Ile
465                 470                 475                 480

Phe Asn Lys Asp Ile Arg Lys Gly Lys Val His
                485                 490

<210> SEQ ID NO 15
<211> LENGTH: 324
<212> TYPE: PRT
<213> ORGANISM: Zymomonas mobilis
<220> FEATURE:
<221> NAME/KEY: MISC_FEATURE
<222> LOCATION: (1)..(324)
<223> OTHER INFORMATION: glk kinase

<400> SEQUENCE: 15

Met Glu Ile Val Ala Ile Asp Ile Gly Gly Thr His Ala Arg Phe Ser
1               5                   10                  15

Ile Ala Glu Val Ser Asn Gly Arg Val Leu Ser Leu Gly Glu Glu Thr
                20                  25                  30

Thr Phe Lys Thr Ala Glu His Ala Ser Leu Gln Leu Ala Trp Glu Arg
            35                  40                  45

Phe Gly Glu Lys Leu Gly Arg Pro Leu Pro Arg Ala Ala Ile Ala
        50                  55                  60

Trp Ala Gly Pro Val His Gly Glu Val Leu Lys Leu Thr Asn Asn Pro
65                  70                  75                  80

Trp Val Leu Arg Pro Ala Thr Leu Asn Glu Lys Leu Asp Ile Asp Thr
                85                  90                  95

His Val Leu Ile Asn Asp Phe Gly Ala Val His Ala Val His
                100                 105                 110

Met Asp Ser Ser Tyr Leu Asp His Ile Cys Gly Pro Asp Glu Ala Leu
            115                 120                 125

Pro Ser Asp Gly Val Ile Thr Ile Leu Gly Pro Gly Thr Gly Leu Gly
        130                 135                 140

Val Ala His Leu Leu Arg Thr Glu Gly Arg Tyr Phe Val Ile Glu Thr
145                 150                 155                 160

Glu Gly Gly His Ile Asp Phe Ala Pro Leu Asp Arg Leu Glu Asp Lys
                165                 170                 175
```

```
Ile Leu Ala Arg Leu Arg Glu Arg Phe Arg Arg Val Ser Ile Glu Arg
                180                 185                 190

Ile Ile Ser Gly Pro Gly Leu Gly Asn Ile Tyr Glu Ala Leu Ala Ala
            195                 200                 205

Ile Glu Gly Val Pro Phe Ser Leu Leu Asp Asp Ile Lys Leu Trp Gln
210                 215                 220

Met Ala Leu Glu Gly Lys Asp Asn Leu Ala Glu Ala Ala Leu Asp Arg
225                 230                 235                 240

Phe Cys Leu Ser Leu Gly Ala Ile Ala Gly Asp Leu Ala Leu Ala Gln
                245                 250                 255

Gly Ala Thr Ser Val Val Ile Gly Gly Val Gly Leu Arg Ile Ala
                260                 265                 270

Ser His Leu Pro Glu Ser Gly Phe Arg Gln Arg Phe Val Ser Lys Gly
                275                 280                 285

Arg Phe Glu Arg Val Met Ser Lys Ile Pro Val Lys Leu Ile Thr Tyr
                290                 295                 300

Pro Gln Pro Gly Leu Leu Gly Ala Ala Ala Tyr Ala Asn Lys Tyr
305                 310                 315                 320

Ser Glu Val Glu

<210> SEQ ID NO 16
<211> LENGTH: 250
<212> TYPE: PRT
<213> ORGANISM: Corynebacterium glutamicum
<220> FEATURE:
<221> NAME/KEY: MISC_FEATURE
<222> LOCATION: (1)..(250)
<223> OTHER INFORMATION: ppgK kinase

<400> SEQUENCE: 16

Met Thr Glu Thr Gly Phe Gly Ile Asp Ile Gly Gly Ser Gly Ile Lys
1               5                   10                  15

Gly Ala Arg Val Asn Leu Lys Thr Gly Glu Phe Ile Asp Glu Arg Ile
                20                  25                  30

Lys Ile Ala Thr Pro Lys Pro Ala Thr Pro Glu Ala Val Ala Glu Val
                35                  40                  45

Val Ala Glu Ile Ile Ser Gln Ala Glu Trp Glu Gly Pro Val Gly Ile
50                  55                  60

Thr Leu Pro Ser Val Val Arg Gly Gln Ile Ala Leu Ser Ala Ala Asn
65                  70                  75                  80

Ile Asp Lys Ser Trp Ile Gly Thr Asp Val His Glu Leu Phe Asp Arg
                85                  90                  95

His Leu Asn Gly Arg Glu Ile Thr Val Leu Asn Asp Ala Asp Ala Ala
                100                 105                 110

Gly Ile Ala Glu Ala Thr Phe Gly Asn Pro Ala Ala Arg Glu Gly Ala
                115                 120                 125

Val Ile Leu Leu Thr Leu Gly Thr Gly Ile Gly Ser Ala Phe Leu Val
                130                 135                 140

Asp Gly Gln Leu Phe Pro Asn Thr Glu Leu Gly His Met Ile Val Asp
145                 150                 155                 160

Gly Glu Glu Ala Glu His Leu Ala Ala Ser Val Lys Glu Asn Glu
                165                 170                 175

Asp Leu Ser Trp Lys Lys Trp Ala Lys His Leu Asn Lys Val Leu Ser
                180                 185                 190

Glu Tyr Glu Lys Leu Phe Ser Pro Ser Val Phe Ile Ile Gly Gly Gly
                195                 200                 205
```

```
Ile Ser Arg Lys His Glu Lys Trp Leu Pro Leu Met Glu Leu Asp Thr
    210                 215                 220

Asp Ile Val Pro Ala Glu Leu Arg Asn Arg Ala Gly Ile Val Gly Ala
225                 230                 235                 240

Ala Met Ala Val Asn Gln His Leu Thr Pro
                245                 250

<210> SEQ ID NO 17
<211> LENGTH: 74
<212> TYPE: DNA
<213> ORGANISM: Corynebacterium glutamicum
<220> FEATURE:
<223> OTHER INFORMATION: T1 termination sequence

<400> SEQUENCE: 17
acaatagtaa aaggaacccct cacgaactgt gagggttcct ttttttgggtt tcgccggagg     60 agacgtcgaa aagc                                                        74

<210> SEQ ID NO 18
<211> LENGTH: 77
<212> TYPE: DNA
<213> ORGANISM: Corynebacterium glutamicum
<220> FEATURE:
<223> OTHER INFORMATION: T2 termination sequence

<400> SEQUENCE: 18
gcatttttag tacgtgcaat aaccactctg gttttttccag ggtggttttt tgatgcccctt     60 tttggagtct tcaactg                                                    77

<210> SEQ ID NO 19
<211> LENGTH: 1419
<212> TYPE: DNA
<213> ORGANISM: Zymomonas mobilis
<220> FEATURE:
<221> NAME/KEY: misc_feature
<222> LOCATION: (1)..(1419)
<223> OTHER INFORMATION: glf permease

<400> SEQUENCE: 19
atgtcctcag aatcttccca aggtctagtt acccgcttgg cgcttattgc tgcaattggt      60
ggacttctat tcggatacga tagtgctgta attgctgcga ttggcactcc agttgacatt     120
catttcattg ctccgcgtca tcttagtgct acagcggcgg cttcacttag tggtatggtt     180
gtagtggctg ttcttgtcgg gtgtgtgact ggttctcttc tctcaggttg gattggcatc     240
cgttttggtc gccggggcgg attgcttatg agtagtattt gtttcgtcgc ggctggattc     300
ggagcggcgt tgaccgagaa actttttcgg actggtggat ctgcacttca gatttttctgt    360 ttcttccgtt tccttgcggg actcggaatt ggtgtcgtta gtacacttac tccgacttac     420
attgctgaaa ttgctcctcc ggataagcgt ggacaaatgg tatccggtca acagatggcg     480
attgttactg gggctcttac tggatatatt ttcacctggt tgcttgcgca tttcggatct     540
atcgactggg tgaatgcgtc tggatggtgt tggtcaccag cttccgaagg gctgatcggt     600
atcgcgtttc tgcttcttct tttgacggcg ccagatacgc cgcattggtt ggtgatgaag     660
ggccggcatt ctgaagcgtc caaaattctg gcacgacttg agcctcaggc tgatccaaat     720
ctcacgattc aaaagattaa agctggcttc gataaagcaa tggataaatc ctctgcagga     780
ctcttcgcat ttggaatcac cgtagttttt gctggtgtta gtgttgcagc atttcaacaa     840
ttggtaggaa tcaatgctgt actgtattat gctccgcaga gtttcagaa tcttggattt     900
```

```
ggtgctgata cggctctgct tcagactatt agtattggcg tagtgaactt tattttcacg      960
atgattgctt cacgtgtggt tgaccgcttc ggtcgcaaac cgcttttgat ctggggtgcg     1020
ctgggtatgg cagcgatgat ggcagttctt ggttgctgtt tctggtttaa agtcggcgga     1080
gtgcttcctt tggcgtctgt tctactttat atcgctgtat ttggtatgtc ctggggtccc     1140
gtgtgttggg tagtactttc tgaaatgttt ccatcttcta tcaaaggtgc agctatgcct     1200
attgcagtga cgggacagtg gttggctaac atccttgtca attttctttt caaagtcgct     1260
gacggctcac cggcgttgaa tcagacgttt aaccatggtt tttcttactt ggtattcgcg     1320 gctcttttcta ttcttggcgg actaattgtt gctcgctttg tcccggaaac aaagggtcgc    1380
tctctcgatg aaattgaaga gatgtggcgt tcacaaaaa                            1419
```

<210> SEQ ID NO 20
<211> LENGTH: 1419
<212> TYPE: DNA
<213> ORGANISM: Streptomyces coelicolor
<220> FEATURE:
<221> NAME/KEY: misc_feature
<222> LOCATION: (1)..(1419)
<223> OTHER INFORMATION: SCO5578

<400> SEQUENCE: 20

```
atggcttcaa cttcacaggc accatcacca ggggcaggaa ccgcgcatcc agatcatcta       60
ggtcatgtca tcttcattgc tgctgctgcg gcgatgggtg gattcctgtt cggatatgat      120
tcctctgtaa tcaatggcgc tgttgaagcg attcgggatc gttatgatgt tggatctgca      180
gttcttgcgc aagtaattgc ggtagctctt attggctgtg caattggcgc tgcgactgcg      240
ggacgcatcg cggaccgcat cggacgcatt cgttgtatgc agattgcagc ggtgcttttt      300
accgtaagtg ctgtaggatc cgcattgcca ttcgctcttt gggatcttgc tatgtggcgt      360
attatcggtg gattcgcgat cggtatggcg agtgtaatcg cccagcttaa cattgctgaa      420
gtgtctcccc cggcgtatcg tggtcgcctt ggttcttttc agcaagctgc aattgtcatt      480
ggtattgcag tatctcagct agtaaactgg ggtcttttga atgctgctgg cggggatcag      540
cgcggtgagc ttatggggct tgaagcttgg caagtaatgc ttggtgtcat ggtaattcct      600
gcagtcttgt acggactgtt gtcctttgct attccagagt ctccgcgttt tctcatttca      660
gttggcaaac gtgagcgagc taaaaagatc cttgaagaag tcgaagggaa agacgtcgat      720
ttcgacgcgc gtgttaccga aattgagcat gctatgcata gaagagaaaa atctagtttt      780
aaagaccttt tgggtggctc ttttttcttc aagccaattg tatggatcgg tatcggactt      840
agtgtttttc agcaattcgt aggcattaat gtcgcgttct attactcctc tactctttgg      900
cagagtgtgg gtgtggatcc ggctgactct ttcttctatt cttttactac aagtattatt      960
aacatcgttg gaacggtcat cgctatgatt ttcgtcgatc gggtgggacg caagccgttg     1020
gcgctcattg gttccgttgg catggttatt ggactggctt tggaagcttg ggcgttctca     1080
ttcgatctag ttgatggcaa acttcctgca acacagggtt gggtggcgct tattgctgct     1140
catgtttttg tgctgttctt tgcgctttct tggggtgttg tggtttgggt gttcttggga     1200
gaaatgtttc cgaatcgtat tcgtgctgct gcattgggag tcgcggcatc cgcacaatgg     1260
attgcgaatt gggctatcac cgcgagtttt ccgagtctag ctgactggaa cctttccggt     1320
acgtatgtaa tctacacgat cttttgctgcg ctttctattc cttttgtgct caaatttgtt    1380
aaagaaacta agggaaaagc gttggaagaa atgggttag                            1419
```

<210> SEQ ID NO 21
<211> LENGTH: 1476
<212> TYPE: DNA
<213> ORGANISM: Corynebacterium glutamicum
<220> FEATURE:
<221> NAME/KEY: misc_feature
<222> LOCATION: (1)..(1476)
<223> OTHER INFORMATION: iolT1

<400> SEQUENCE: 21

| | | | | | |
|---|---|---|---|---|---|
| atggcttcta | cttttattca | agctgattca | cctgaaaagt | caaaaaagct | gccacctcta | 60 |
| actgaaggcc | catatcgtaa | gcgattgttc | tacgttgcgc | ttgttgcgac | ttttggtggc | 120 |
| ttgctttttg | gatatgatac | gggcgtcatt | aatggtgctc | ttaatccaat | gactcgcgag | 180 |
| cttggattga | cggcttttac | tgaaggcgta | gttacttctt | ctctcctatt | cggtgcggct | 240 |
| gctggcgcta | tgttcttcgg | acgcatctct | gataattggg | gacgccgtaa | gactatcatt | 300 |
| tctctggctg | ttgcattttt | cgttggtact | atgatttgtg | tattcgcgcc | atccttcgcg | 360 |
| gttatggtag | ttggaagagt | ccttttggga | ttggctgtgg | ggggagcatc | aactgttgtg | 420 |
| cctgtatatc | tcgcagaact | tgctccgttc | gagatccgtg | gttctttggc | tggtcgtaac | 480 |
| gaactcatga | ttgtcgtagg | ccagttggct | gcgtttgtta | ttaatgcaat | cattggtaac | 540 |
| gtgttcggac | atcatgatgg | tgtctggcgt | tacatgctag | cgattgcagc | gatcccagca | 600 |
| attgcgctgt | ttttcggcat | gttgcgggta | ccggagtccc | cacgctggct | tgtagagcgg | 660 |
| gggcgcattg | acgaagctcg | tgcggtactt | gaaaccattc | gtccgttgga | acgcgcgcat | 720 |
| gctgaagtgg | ctgatgttga | acatcttgcg | cgtgaagaac | atgctgtaag | tgagaaatca | 780 |
| atgggtctgc | gtgaaatctt | gtccagtaaa | tggcttgtgc | gcattcttct | tgtgggaatt | 840 |
| gggcttggag | tagcacagca | acttactggt | atcaatagta | ttatgtatta | tggccaagtc | 900 |
| gttctcattg | aagcgggttt | cagtgaaaac | gcagcgctta | ttgctaatgt | agctcctggt | 960 |
| gtgatcgcag | tggttggtgc | tttcattgct | ctttggatga | tggatcgtat | caatcgacgc | 1020 |
| accacgctta | ttacgggcta | ctcccttacg | accatctctc | atgttctgat | tggtatcgct | 1080 |
| tctgttgcgt | ttccggttgg | tgatccacta | cgtccttatg | tgattcttac | acttgtagtt | 1140 |
| gttttttgtgg | gatctatgca | gacgttttg | aatgtagcta | cgtgggtcat | gctttccgag | 1200 |
| ttgtttccat | ggctatgcg | cggattcgca | atcggaatta | gtgttttctt | tttgtggatt | 1260 |
| gcaaacgcgt | tccttggact | tttctttccg | acaattatgg | aagctgttgg | gcttacggga | 1320 |
| actttcttca | tgttcgcggg | tattggtgtc | gtagcgctga | tttttattta | cactcaggtg | 1380 |
| cccgagactc | ggggacgcac | ccttgaagaa | atcgacgaag | atgttacttc | tggagtcatc | 1440 |
| tttaacaaag | acattcgtaa | aggtaaagtc | cattag | | | 1476 |

<210> SEQ ID NO 22
<211> LENGTH: 1458
<212> TYPE: DNA
<213> ORGANISM: Synechocystis sp. PCC6803
<220> FEATURE:
<221> NAME/KEY: misc_feature
<222> LOCATION: (1)..(1458)
<223> OTHER INFORMATION: glcp (CAA34119.1)

<400> SEQUENCE: 22

| | | | | | |
|---|---|---|---|---|---|
| atgcgtcaaa | ccggttcttt | gcgtcctatt | cttgtccctg | tgtggatcct | tgtacttgta | 60 |
| gcggcacttg | cgggttgtgc | aacacgtact | gatgatcagc | cgactgaatc | cgctccaccc | 120 |
| ccagcgcaac | aagctccacc | aacgccggca | gaaattcgtg | cgatcgctaa | agatgcttat | 180 |

-continued

```
atttggggat tcccgttggt tgataattac cgtgttcagt atagttactt tgtagacaag    240
accgaccccg agtataaggg tggattcaat gaagtacata atactgctcg gctttatact    300
ccggctgata aagctattca gaccectaac gcagatactc cgtattcttt tgtaggcgca    360
gacttgcgta ctgagcctct ggtctttact gtgccgccga ttgagcagaa tcgttacttc    420
tctctgcagt tcgtggatgg ttatacctat aatgtagctt atgttggttc tcgtacgaca    480
ggaaacggcg ggggacgcta cttgctcgct ggtccaggtt gggagggtga aaagcccgag    540
ggtgtagacg aaatcattcg ctcagacacg gaccttgcgt tcgtccttta tcggacgcag    600
ctgtttgggc ctagagattt ggataatatc aagaaaattc aggctggata tcaagttgcg    660
ccgctttccg tttatcttaa acaaccaagt ccacctccgg ctcctccgat tgattttacg    720
cctccactta cgccagaagc gcagaaaacc tctccacaat tcttcgagat tttgaacgca    780
gcgcttcgct atgcgccggt taaaccagaa gaacaagaaa tgcgagagcg ctttgcacgt    840
attggtattg cccctgatgg cgacttcgat gctgataaac tttctcctga gactcgcgaa    900
gcgattgaag atggaatggc gaatgcgtgg gttgaatttg atcgtttcaa acaagataaa    960
gttgacacgg gtgaagtcgg cagtgctcaa ctatttggta ccgcggatga tctaaaggga    1020
aactaccttt accgcatggc tggtgctgtt ctgggcattt atggaaatac tgcggctgaa    1080
gcgctttatc caagtgctat gcttgatgca gacggccagc ctctcactgg aactaactca    1140
tacacgtacc gatttgcgcc agaccaactt ccgccggtga atgctttctg gtcacttacg    1200
atctatgaat tgccttcctc tcaacttgtg gacaatccga ttgatcgcta tttgattaat    1260
agcgaaatgc tcccatcttt ggtcccggat ccagatgggg cttatacact tcgcatccag    1320
aatactcagc cgccagagaa tgaagcaaac tggctgcctg ctccgaaggg accgtttacg    1380
cttgtattgc gcctttactg gccgaaacct gatgcactta atggaacttg gcaggctcca    1440
aaaccagaaa agatttag                                                  1458
```

<210> SEQ ID NO 23
<211> LENGTH: 1458
<212> TYPE: DNA
<213> ORGANISM: Mycobacterium smegmatis
<220> FEATURE:
<221> NAME/KEY: misc_feature
<222> LOCATION: (1)..(1458)
<223> OTHER INFORMATION: MSMEG_4187

<400> SEQUENCE: 23

```
atgcgtcaaa ccggttcttt gcgtcctatt cttgtccctg tgtggatcct tgtacttgta     60
gcggcacttg cgggttgtgc aacacgtact gatgatcagc cgactgaatc cgctccaccc    120
ccagcgcaac aagctccacc aacgccggca gaaattcgtg cgatcgctaa agatgcttat    180
atttggggat tcccgttggt tgataattac cgtgttcagt atagttactt tgtagacaag    240
accgaccccg agtataaggg tggattcaat gaagtacata atactgctcg gctttatact    300
ccggctgata aagctattca gaccectaac gcagatactc cgtattcttt tgtaggcgca    360
gacttgcgta ctgagcctct ggtctttact gtgccgccga ttgagcagaa tcgttacttc    420
tctctgcagt tcgtggatgg ttatacctat aatgtagctt atgttggttc tcgtacgaca    480
ggaaacggcg ggggacgcta cttgctcgct ggtccaggtt gggagggtga aaagcccgag    540
ggtgtagacg aaatcattcg ctcagacacg gaccttgcgt tcgtccttta tcggacgcag    600
ctgtttgggc ctagagattt ggataatatc aagaaaattc aggctggata tcaagttgcg    660
```

```
ccgctttccg tttatcttaa acaaccaagt ccacctccgg ctcctccgat tgattttacg    720
cctccactta cgccagaagc gcagaaaacc tctccacaat tcttcgagat tttgaacgca    780
gcgcttcgct atgcgccggt taaaccagaa gaacaagaaa tgcgagagcg ctttgcacgt    840
attggtattg gccctgatgg cgacttcgat gctgataaac tttctcctga gactcgcgaa    900
gcgattgaag atggaatggc gaatgcgtgg gttgaatttg atcgtttcaa acaagataaa    960
gttgacacgg gtgaagtcgg cagtgctcaa ctatttggta ccgcggatga tctaaaggga   1020
aactaccttt accgcatggc tggtgctgtt ctgggcattt atggaaatac tgcggctgaa   1080
gcgctttatc caagtgctat gcttgatgca gacggccagc ctctcactgg aactaactca   1140
tacacgtacc gatttgcgcc agaccaactt ccgccggtga atgctttctg gtcacttacg   1200
atctatgaat tgccttcctc tcaacttgtg gacaatccga ttgatcgcta tttgattaat   1260
agcgaaatgc tcccatcttt ggtcccggat ccagatgggg cttatacact tcgcatccag   1320
aatactcagc cgccagagaa tgaagcaaac tggctgcctg ctccgaaggg accgtttacg   1380
cttgtattgc gcctttactg gccgaaacct gatgcactta atggaacttg gcaggctcca   1440
aaaccagaaa agatttag                                                 1458
```

<210> SEQ ID NO 24
<211> LENGTH: 1554
<212> TYPE: DNA
<213> ORGANISM: Bifidobacterium longum
<220> FEATURE:
<221> NAME/KEY: misc_feature
<222> LOCATION: (1)..(1554)
<223> OTHER INFORMATION: BL1631

<400> SEQUENCE: 24

```
atgactacaa caacggcttc accagtatca aaacagaccg cttccgctgc tcaggaaact     60
agtgctaccg gtgctgcggc aacggcgatt gaaacgattg agactggtgt tgctggtgtg    120
gctggtgcag cgactaatgc agcggcgaat gctatcgaag atctagaggc agcggaatct    180
catggattta gtacgcgctt tcccctgaac tctgcgttta tcttcacctt cggagcgctt    240
ggcggaatgc tgtttggatt cgatacgggc attatttcag gtgcaagtcc tttgattgag    300
tctgactttg gtttgtctgt atcacagact ggtttcatta cgtctagtgt tctcatcggt    360
tcatgtgctg gcgcttttgtc cattggagca ctctctgatc ggttcggtcg caaaaagcta    420
cttattgtga gtgcgcttct tttcttgctg ggatccggtt tgtgtgcgtc ctctactggt    480
ttcgcgatga tggtctgtgc tcgtatcatt cttgggctcg ctgtcggcgc agcgtctgca    540
cttactccgg cttaccttgc tgaattggcg ccgaaagagc gtcgtggatc tcttttccacc    600 cttttttcagc ttatggttac tttcggaatt ttgctggctt atgcatctaa cctgggattt    660
cttaaccata atcttttcgg tattcgtgat tggcgctgga tgcttggctc tgcgttggtg    720
ccagcggcgc tgctacttct tggtgggttg ttgcttcctg aaagtccgcg gtacctggtc    780
aataaaggtg acactcgcaa tgcttttaag gttcttaccc ttatccgcaa agacgttgat    840
caaacacaag tacagatcga acttgatgaa atcaaagctg tagctgctca agatacgaaa    900
ggcggagtaa gagaactgtt tcgaatcgca cgcccagcgc ttgtggcagc tatcggaatc    960
atgttgttcc agcaacttgt tggaattaac tctgtcatct atttcctacc tcaggtattc   1020
attaaaggct tcggctttcc tgagggtgat gctatttggg tttccgtcgg tattggtgta   1080
gtgaatttcg tttctacaat tgttgcaact cttatcatgg accgttttcc acgcaagggt   1140
atgttgattt ttggtagtat tgtaatgact gtaagtcttg ctgttttggc tgtgatgaat   1200
```

```
tttgtgggtg atgttgctgt acttgcggta ccgactatga ttctgattgc attctatatt    1260
ctaggtttcg ctgtctcctg gggacctatt gcttgggtcc ttattggcga atctttcca    1320 ctttctgtac gtggcattgg atcctccttc ggatctgcgg cgaattggct aggaaacttt    1380
atcgtgagtc aattctttct tgtccttctt gatgcttttg gaataatgt tggcggaccg    1440 tttgcaattt tcggtgtttt tagtgcgttg tcaattccgt tgtcttgcg tcttgtacca    1500 gagactaagg gtaaatccct ggaagaaatc gagaagaaa tgactaaacg ttag          1554
```

```
<210> SEQ ID NO 25
<211> LENGTH: 750
<212> TYPE: DNA
<213> ORGANISM: Corynebacterium glutamicum
<220> FEATURE:
<221> NAME/KEY: misc_feature
<222> LOCATION: (1)..(750)
<223> OTHER INFORMATION: ppgK kinase

<400> SEQUENCE: 25
atgacagaaa ctggtttcgg aattgatatt ggtggcagtg gaattaaggg tgcgcgtgta     60
aatcttaaaa ccggagagtt tatcgatgaa cggatcaaaa ttgcgacgcc aaagccagcg    120
actcccgaag ctgtagctga agttgtagca gaaatcattt ctcaagctga gtgggaaggc    180
cctgtcggaa ttactctgcc atcagttgtt cgcggtcaga ttgcgctttc cgcggctaat    240
atcgataagt cttggattgg tactgacgtc catgaattgt ttgatcgtca tctcaatggt    300
agagagatta cggttcttaa cgacgcggat gctgctggga ttgcagaagc gacgttcggt    360
aatccggcag cacgcgaggg cgctgttatt cttttgaccc tgggtactgg tattggatct    420
gcgttccttg tggatggtca actatttccg aatactgagc ttggacacat gattgtggac    480
ggtgaagagg ctgaacatct ggctgcagct tccgtgaaag aaaatgaaga tctctcttgg    540
aagaaatggg cgaaacatct taacaaagta ttgagtgaat atgaaaaact atttccccct    600
tcagtattca ttatcggggg cggaattagt cgaaaacatg agaaatggct tccgcttatg    660
gaacttgaca ctgatatcgt gccagcggaa cttcgcaatc gtgctggaat cgttggagcg    720
gcgatggctg tcaatcagca tttgacgcct                                    750
```

```
<210> SEQ ID NO 26
<211> LENGTH: 972
<212> TYPE: DNA
<213> ORGANISM: Zymomonas mobilis
<220> FEATURE:
<221> NAME/KEY: misc_feature
<222> LOCATION: (1)..(972)
<223> OTHER INFORMATION: glk kinase

<400> SEQUENCE: 26
atggaaattg tcgctattga tattgggggt acgcatgcac gtttttctat tgctgaagtc     60
tccaacggtc gagtacttag tcttggagaa gagacaacgt ttaaaactgc ggagcatgca    120
agtttgcaac tggcttggga acgttttgga gagaaattgg tcgcccact gccacgtgcg    180 gctgctattg cttgggcggg accagtccat ggtgaagttt tgaagctaac taataatccg    240
tgggtacttc gtccagctac acttaatgaa aaacttgata ttgatacgca tgttttgatt    300
aatgactttg gtgcggtcgc acatgctgtg gctcacatgg attcttctta tcttgaccat    360
atttgtggac ctgacgaagc gctgccctcc gatggtgtga tcaccatttt gggtccggga    420
accggacttg gtgttgcgca tctacttcgc accgaaggcc gctatttcgt cattgagact    480
```

```
gaaggcggac atattgattt cgcgccattg gatcgtcttg aagataagat tcttgcacgc    540
ctgcgcgaac gttttcgtcg ggtgagtatc gagagaatca tctcaggtcc gggattgggt    600
aacatttacg aagcgctggc ggctattgaa ggcgtacctt tctctcttct tgatgacatt    660
aagctttggc agatggcgtt ggaaggcaaa gataatcttg ctgaggctgc actagaccgc    720
ttttgtttgt ccctcgpggc aatcgctggt gatcttgcgc ttgcgcaggg tgcaacttct    780
gtagtgatcg gtgggggcgt tggtttgcgg attgcatccc atcttccgga gtcaggtttt    840
cgtcaacgct tcgtttctaa gggccgtttc gaacgtgtta tgagtaaaat cccggtaaaa    900
cttattactt atcctcagcc aggactcctt ggagcggcag ctgcgtatgc taataaatac    960
tctgaagttg aa                                                        972
```